(12) United States Patent
van Nostrand

(10) Patent No.: US 9,217,013 B2
(45) Date of Patent: Dec. 22, 2015

(54) TREATMENT OF AMYLOIDOSES USING MYELIN BASIC PROTEIN AND FRAGMENTS THEREOF

(71) Applicant: The Research Foundation for the State University of New York, Albany, NY (US)

(72) Inventor: William E. van Nostrand, East Setauket, NY (US)

(73) Assignee: The Research Foundation For the State University of New York, Albany, NY (US)

(*) Notice: Subject to any disclaimer, the term of this patent is extended or adjusted under 35 U.S.C. 154(b) by 24 days.

(21) Appl. No.: 14/265,958

(22) Filed: Apr. 30, 2014

(65) Prior Publication Data

US 2015/0025014 A1 Jan. 22, 2015

Related U.S. Application Data

(62) Division of application No. 13/061,433, filed as application No. PCT/US2009/004907 on Aug. 28, 2009, now Pat. No. 8,815,794.

(60) Provisional application No. 61/190,478, filed on Aug. 28, 2008, provisional application No. 61/190,480, filed on Aug. 28, 2008.

(51) Int. Cl.
*A61K 38/08* (2006.01)
*C07K 7/06* (2006.01)
*A61K 38/17* (2006.01)
*C07K 14/47* (2006.01)
*G01N 33/68* (2006.01)
*A61K 38/00* (2006.01)

(52) U.S. Cl.
CPC ............... *C07K 7/06* (2013.01); *A61K 38/1709* (2013.01); *A61K 38/1716* (2013.01); *C07K 14/4711* (2013.01); *C07K 14/4713* (2013.01); *G01N 33/6896* (2013.01); *A61K 38/00* (2013.01); *G01N 2500/00* (2013.01)

(58) Field of Classification Search
None
See application file for complete search history.

(56) References Cited

FOREIGN PATENT DOCUMENTS

WO    WO 9612737 A2 * 5/1996

* cited by examiner

*Primary Examiner* — Gregory S Emch
(74) *Attorney, Agent, or Firm* — Medlen & Carroll, LLP

(57) ABSTRACT

In its various embodiments, the invention provides myelin basic proteins and fragments of that interfere with the fibrillization of peptides implicated in the amyloidoses, especially the amyloid-b eta peptide associated with Alzheimer's disease ("AD") and cerebral amyloid angiopathy ("CAA"). Some embodiments provide methods of identifying additional interfering fragments. Others provide methods of identifying substances that modulate the interference. Further embodiments provide methods of preventing amyloidoses, especially AD and CAA by administering myelin basic proteins or fragments thereof.

18 Claims, 30 Drawing Sheets

FIGURE 3

| Peptide MBP1 | $^1$ASQKRPSQRHGSKYLATASTMDHARHGFLPRHRDTGILD SIGRFFGGDRGAPKRGSGKDSHHP$^{63}$ | SEQ ID NO: 45 |
|---|---|---|
| Peptide MBP2 | $^{64}$ARTAHYGSLPQKSHGRTQDENPVVHFFKNIVTPRTPPPS$^{102}$ | SEQ ID NO: 46 |
| Peptide MBP3 | $^{103}$QGKGRGLSLSRFSWGAEGQRPGFGYGGRASDYKS$^{136}$ | SEQ ID NO: 47 |
| Peptide MBP4 | $^{137}$AHKGFKGVDAQGTLSKIFKLGGRDSRSGSPMARR$^{170}$ | SEQ ID NO: 48 |

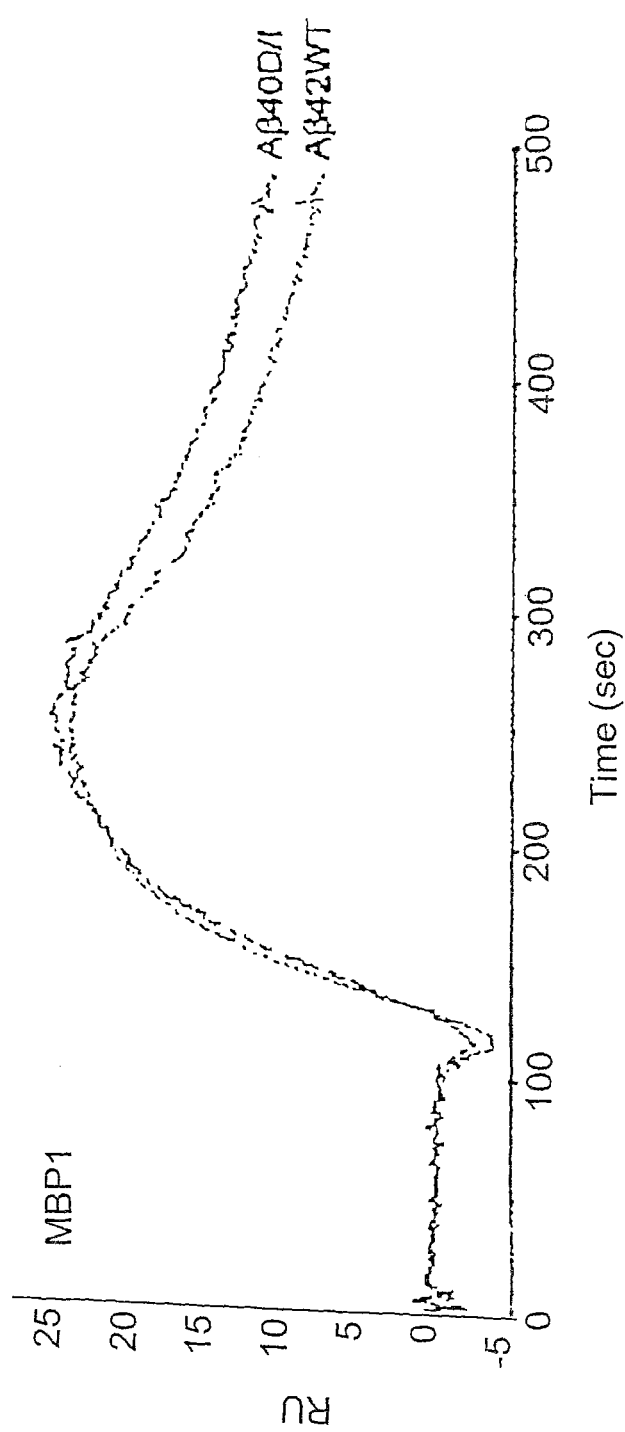

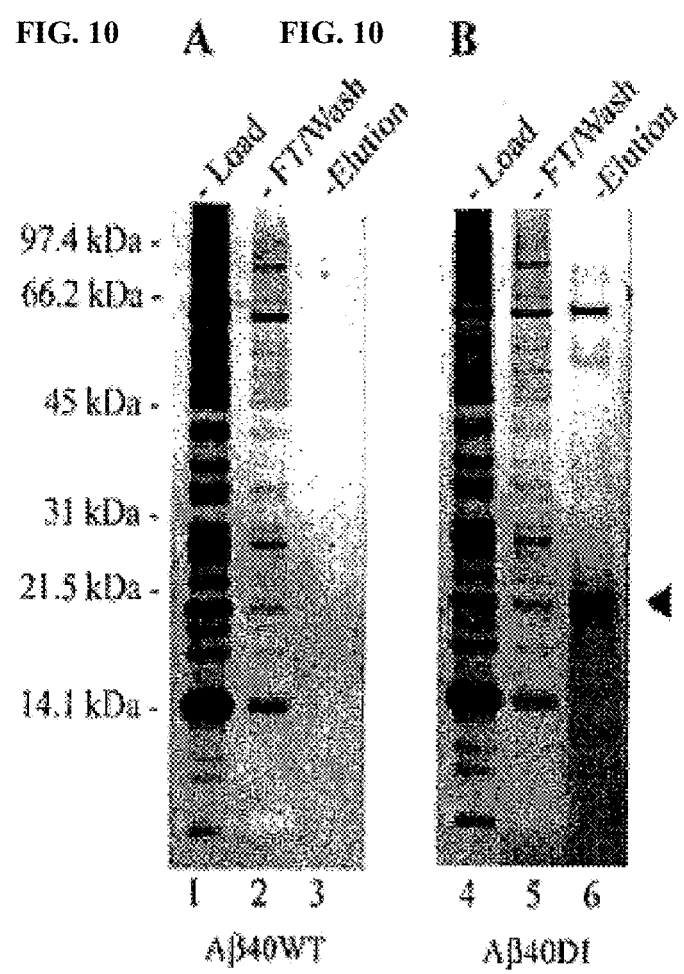

FIG.17A  FIG.17B  FIG.17C
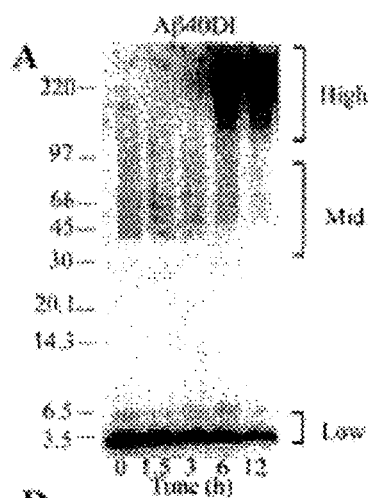 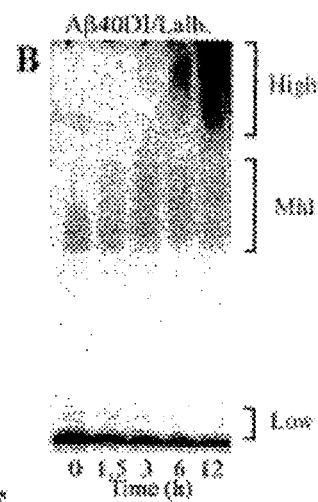 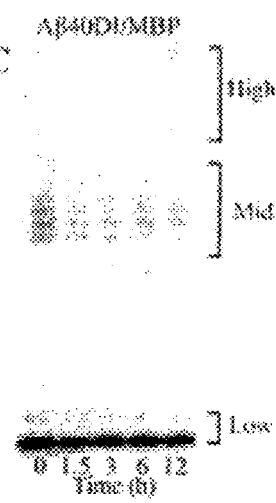
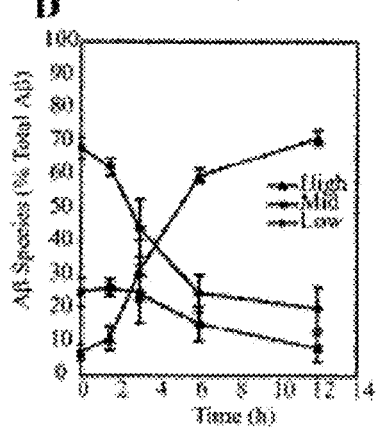 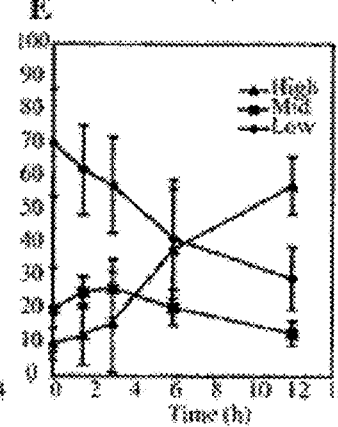 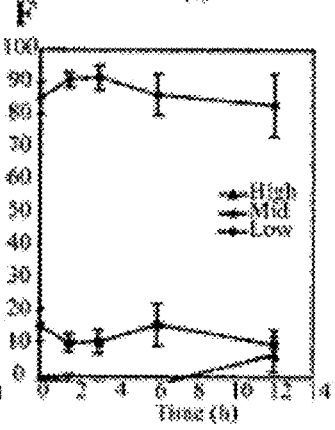
FIG.17D  FIG.17E  FIG.17F

SEQ ID NO: 49  C  1 - MASQKRPSQRHGSKYLATASTMDHARHGFLPRHRDTGILDSIGRFFGGDRGAPKRGSGKDSHHP - 64

SEQ ID NO: 50  D  1 - DAEFRHDSGYEVHHQKLVFFAEDVGSNKGAIIGLMVGGVV - 40

TREATMENT OF AMYLOIDOSES USING MYELIN BASIC PROTEIN AND FRAGMENTS THEREOF

FIELD OF THE INVENTION

The present invention relates to novel uses of myelin basic protein, including its variants, and fragments thereof, to treat or prevent disease. The invention also relates to the identification of substances that modulate the potency of these treatments. In another aspect, the invention relates to methods of delivering such agents, or modulators thereof, or both, to sites where such disease originates or is manifest.

BACKGROUND

Fibrillar deposits of proteinaceous material ("amyloid") accompany a plethora of diseases. So-called amyloid diseases such as Alzheimer's disease, bovine spongiform encephalopathy (BSE), Creutzfeldt-Jakob disease (CJD), laughing death syndrome, and scrapie are all neurodegenerative diseases characterized pathologically by the presence of extracellular amyloid deposits or plaques in brain tissue. So far, at least 23 unrelated proteins are known to either form an insoluble structure known as a β-sheet or to be precursors of peptides that form into β-sheets. These proteins (sometimes referred to herein as "fibrillizing peptides") tend to aggregate into fibrils and then into more complex insoluble deposits associated with diseases, collectively referred to as amyloidoses (Baethge et al., eMedicine.com, 2006, accessible on the world wide web as med/topic 3377).

For example, Aβ peptides (or "amyloid beta peptides," "A-beta peptides" or simply "Aβ") are fibrillizing peptides having 39-43 amino acids. The most common of the wild-types are Aβ-40 and Aβ-42. Aβ-40 is more abundant, but Aβ-42 is more fibrillogenic. They are produced proteolytically from the amyloid β-protein precursor (AβPP), a large, type I integral membrane protein, through sequential proteolysis by β- and γ-secretase activities (Vassar et al., Science 286:735-741, 1999, Beck et al., J. Med. Chem. 46:4625-4630, 2003, DeStrooper et al., Nature 391:387-390, 1998, Wolfe et al., Nature 398:513-517, 1999). Depositions of Aβ in the parenchyma of the brain, which is characteristic of Alzheimer's disease, form readily from soluble molecules, first as soluble oligomers that are toxic in their own right (S. M. Chafekar et al., Biochim. Biophys. Acta 1782:523-31, 2008). It is thought that these oligomers go on to form diffuse plaques which, although insoluble, exhibit little surrounding pathology. However, although not proven, it is widely believed that these diffuse plaques progress to fibrillar forms, thence to fibrillar plaques associated with dystrophic neurons, neurofibrillary tangles, and inflammation (Selkoe, Physiol. Rev. 8:741-766, 2001).

Fibrillar Aβ deposition also occurs within and along primarily small and medium arteries and arterioles of the cerebral cortex and leptomeninges and in the cerebral microvasculature, a condition known as cerebral amyloid angiopathy ("CAA") (Vinters, Stroke 18: 311-324, 1987, Jellinger, J. Neural Transm. 109:813-836, 2002, Vinters and Farag, Adv. Neurol. 92:105-112, 2003). This condition accounts for up to 20% of all spontaneous primary intracerebral hemorrhages and is a key pathological lesion in nearly all patients with Alzheimer's disease and certain related disorders. Familial CAA stems from mutant forms of Aβ, prominently the Dutch- and Iowa-type mutants. These particular mutant forms of the peptide tend not to accumulate in the brain parenchyma, but they are uncommonly aggressive fibrillizers in vitro and in cerebrovascular tissue compared to wild-type Aβ, all the more so when the peptide carries both mutations at once. Fibrillar forms of the mutants in the cerebral vascular have been shown to cause degeneration and cell death of smooth muscle cells and pericytes in affected larger cerebral vessels and cerebral microvessels, respectively (Vinters and Farag, Adv. Neurol. 92:105-112, 2003, Wisniewski et al., Amyloid 1: 8-16, 1994, Kawai et al., Brain Res. 623:142-146, 1993). Recent findings have implicated cerebral microvascular Aβ deposition in promoting neuro-inflammation and dementia in Alzheimer's disease (Bailey et al., Neurol. Res. 26:573-578, 2004; Atterns and Jellinger, Acta Neuropathol. 107:83-90, 2004; *Neuropathology Group of the Medical Research Council Cognitive Function and Ageing Study*, Lancet 357:169-175, 2001; Thal et al., J. Neuropathol. Exp. Neurol. 62:1287-1301, 2003).

Aβ also appears to enhance the accumulation of the alpha-synucleins that comprise the cytoplasmic inclusions found in brain neurons in subjects (mice) with Lewy body dementia (E Masliah, et al., Proc. Natl. Acad. Sci. U.S.A. 98:12245-50, 2001).

Baethge et al. (eMedicine.com, 2006, accessible on the world wide web as med/topic 3377) have assembled a long list of diseases that stem from abnormal accumulations of fibrillizing peptides in cells, tissues and organs of the body. The standard of care for many of the listed maladies is summarized therein. In most cases, care is only palliative. In no case is a treatment curative. The need for more and better ways of preventing the fibrillization of fibrillizing peptides into insoluble deposits is manifest.

SUMMARY

In its various embodiments, the present invention employs myelin basic protein ("MBP") and variants thereof (including isoforms), and certain fragments of MBP, to interfere with fibrillization of a fibrillizing peptide, Aβ in particular. In some embodiments, the invention provides a MBP that digests fibril precursors, thus depriving the fibrillization process of its substrate. In some embodiments, a MBP changes fibril precursors into forms that do not or cannot assemble or fibrillize. In some embodiments, a MBP interferes with fibrillization by disrupting an insoluble fibrillar product of the fibrillization process. In some embodiments, the invention provides a MBP or fragment thereof that interferes with fibrillization, such that fibrillization is slowed or prevented, thus preventing an amyloid disease or at least inhibiting the progression of the disease or reducing the severity of its symptoms.

In one embodiment, the inhibiting of, or interference with, fibrillization comprises contacting a soluble or dissolved fibrillizing peptide with a MBP under conditions wherein the MBP at least partially proteolyzes the peptide.

In one embodiment, the inhibiting of, or interference with, fibrillization comprises disrupting a product of fibrillization by contacting said product with a MBP under conditions wherein a disruption of the product occurs.

In one embodiment, the inhibiting of, or interference with, fibrillization comprises disrupting a product of fibrillization by contacting the product with a MBP under conditions wherein the MBP at least partially proteolyzes a fibrillized peptide comprising the product.

In one embodiment, the inhibiting of, or interference with, fibrillization comprises contacting or mixing a soluble or dissolved fibrillizing peptide with a fragment of a MBP. The interference takes place under conditions such that a fibrillizing interaction between a plurality of said fibrillizing peptides is inhibited. In another embodiment, the inhibiting or interfering comprises contacting a product of fibrillization with said fragment under conditions such that further fibrillization is slowed or prevented.

In various embodiments, the fragment in contact or mixed with the fibrillizing peptide may be any interfering fragment, including variants. In some embodiments, an interfering fragment and a full-length MBP may act in concert. In preferred embodiments, the fragment in contact or mixed with the fibrillizing peptide or a product of fibrillization is a peptide comprising the amino acid residues KRGX$_1$X$_2$X$_3$X$_4$X$_6$X$_6$HP (SEQ ID NO:1) wherein X$_1$-X$_6$ are amino acids selected from the group consisting of G, P, A, V, L, I, M, C, F, Y, W, H, K, R, Q, N, E, D, S and T. In more preferred embodiments, the fragment is a peptide consisting of the amino acid residues KRGSGKDSHHP (SEQ ID NO:2), KRGRKQCKTHP (SEQ ID NO:3) or KRGSGKVPWLK (SEQ ID NO:4). A product of fibrillization may be an oligomer, the formation of which may be slowed or prevented by the presence of an interfering fragment, or the disruption of which may be potentiated or enhanced by the presence of said fragment. The oligomer, as well as other products of fibrillization, may have toxic effects that the fragments reduce or inhibit when they contact a fibrillizing peptide that comprises the product of fibrillization. The inhibition may occur in vitro, in situ or in vivo.

In one embodiment, the invention provides a method of identifying an interfering variant of MBP, the method comprising: a) contacting or mixing a known interfering MBP with a first sample comprising a soluble or dissolved fibrillizing peptide under conditions wherein the known interfering MBP proteolyzes the peptide; b) contacting or mixing a candidate variant with a second sample comprising said soluble or dissolved fibrillizing peptide; c) measuring proteolysis in the first sample and in the second sample, and d) comparing the measurements, thereby identifying the candidate as either interfering or not.

In one embodiment, the invention provides a method of identifying an interfering variant or fragment of MBP, the method comprising: a) contacting or mixing a known interfering MBP or fragment thereof. With a first sample comprising a soluble or dissolved fibrillizing peptide under conditions wherein the known interfering MBP or fragment thereof binds to the peptide; b) contacting or mixing a candidate variant with a second sample comprising said soluble or dissolved fibrillizing peptide; c) measuring binding in the first sample and in the second sample, and d) comparing the measurements, thereby identifying the candidate as either interfering or not.

In one embodiment, the invention provides a method of identifying a disruptive variant of MBP, the method comprising: a) contacting or mixing a known disruptive MBP with a first sample of a fibrillization product, the product comprising a fibrillizing peptide; b) contacting or mixing a candidate variant of MBP with a second sample of the product; c) determining a disruption of the first sample of the product by the known disruptive MBP and a disruption of the second sample by the candidate variant of MBP, and d) comparing the measurements, thereby identifying the candidate as either disruptive or not.

In one embodiment, proteolysis of the fibrillizing peptide in the product is a determinant of disruption.

In some embodiments, an MBP is detected by contacting the MBP with a specific antibody against the MBP under conditions wherein an MBP-antibody complex can be detected.

In one embodiment, an interfering MBP is utilized in a method of identifying a substance that modulates an interference with the formation of a product of fibrillization, the product comprising a fibrillizing peptide. The method comprises a) contacting or mixing an amount of an interfering MBP with a first sample comprising a dissolved fibrillizing peptide under conditions wherein the interfering MBP at least partially proteolyzes the peptide; b) contacting or mixing said amount with a second sample of said dissolved fibrillizing peptide and a candidate modulating substance; c) measuring proteolysis (or the degree of proteolysis) in the first sample substance as a modulating substance or not. In one embodiment, the modulator is an anti-MBP antibody. In one embodiment the antibody is specific for a region of SEQ ID NO:2. In one embodiment, the antibody inhibits said interference.

In one embodiment, an interfering MBP or fragment thereof is utilized in a method of identifying a substance that modulates an interference with the formation of a product of fibrillization, the product comprising a fibrillizing peptide. The method comprises a) contacting or mixing an amount of an interfering MBP or fragment thereof with a first sample comprising a dissolved fibrillizing peptide under conditions wherein the interfering MBP or fragment thereof binds the peptide; b) contacting or mixing said amount with a second sample of said dissolved fibrillizing peptide and a candidate modulating substance; c) measuring binding (or the degree of binding) in the first sample and in the second sample, and d) comparing the measurements, thereby identifying the candidate substance as a modulating substance or not. In one embodiment, the modulator comprises an anti-MBP antibody. In one embodiment the antibody is specific for a region of SEQ ID NO:2. In one embodiment, the antibody inhibits said interference.

In other embodiments, a disruptive MBP is utilized in a method of identifying a substance that modulates a disruption by said disruptive MBP. The method comprises a) contacting or mixing an amount of a disruptive MBP with a first sample of a fibrillization product, the product comprising a fibrillizing peptide, under conditions wherein said amount disrupts the product; b) contacting or mixing a second sample of the product with said amount of disruptive MBP and with a substance that is a candidate for modulating the disruption; measuring a disruption of the first sample of the product and a disruption of the second sample, d) comparing the measurements, thereby identifying the candidate as a modulator or not. In one embodiment, the modulator comprises an anti-MBP antibody. In one embodiment the antibody is specific for a region of SEQ ID NO:2. In one embodiment, the antibody inhibits said disruption.

In some embodiments, a modulating substance is effective because it affects the fibrillizing peptide. In others, it is effective because of its effect on the MBP. In still other embodiments, the modulating substance affects fibrillization only after the MBP has contacted the fibrillizing peptide. Accordingly, embodiments wherein the candidate substance contacts the fibrillizing peptide before the substance contacts the MBP are contemplated, as are embodiments wherein the substance contacts the fibrillizing peptide after the substance contacts the MBP. In some embodiments, the fibrillizing peptide is in a product of fibrillization. In some embodiments the fibrillizing peptide is dissolved.

In one embodiment, the invention provides a method of identifying a fragment of a myelin basic protein that interferes with fibrillization, the method comprising: a) as a control, contacting or mixing a known interfering fragment with a first sample comprising a fibrillizing peptide under a condition wherein the interfering fragment interferes with a fibrillization; b) contacting or mixing a candidate fragment of a myelin basic protein with a second sample comprising said fibrillizing peptide under the condition; c) measuring in the first sample and in the second sample a determinant of fibrillization, and d) comparing the amounts, thereby identifying the candidate as either interfering or not.

In one embodiment, the determinant of fibrillization is selected from the group consisting of an amount of (i) a fibrillizing peptide-fragment complex, (ii) a fibrillizing peptide oligomer, and (iii) a fibrillizing peptide fibril. In one embodiment, an interfering MBP fragment is utilized in a method of identifying a substance that modulates an interference with the formation of a product of fibrillization, the product comprising a fibrillizing peptide. The method comprises a) contacting or mixing an amount of an interfering MBP fragment with a first sample comprising a fibrillizing peptide under a condition wherein the interfering MBP fragment interferes with a fibrillization; b) contacting or mixing an amount of a candidate modulating substance with said amount of said interfering MBP fragment and with a second sample of said fibrillizing peptide; c) measuring in the first sample and in the second sample a determinant of fibrillization, and d) comparing the amounts, thereby identifying the candidate substance as a modulating substance or not.

In alternative embodiments of the invention, the fibrillizing peptide is in an environment selected from the group consisting of in vitro, in situ and in vivo.

In preferred embodiments, the fibrillizing peptide is amyloid-beta peptide.

In a preferred embodiment, proteolysis of the fibrillizing peptide is a determinant of disruption.

In these embodiments, the fibrillizing peptide is in an environment selected from the group consisting of in vitro, in situ and in vivo.

In one embodiment, the proteolytic effect of MBP is exploited to treat a subject having a disease or disorder that is susceptible to treatment by preventing a product of fibrillization from forming, the product comprising a fibrillizing peptide. In one embodiment, an interfering fragment of MBP is exploited. Preferred methods comprise administering to the subject an effective amount of a myelin basic protein ("MBP") or a fragment thereof in a pharmaceutically acceptable vehicle. In various embodiments the vehicle may be as simple as physiological saline, or as elaborate as a liposomal preparation, for example. Optionally, the administering may be adapted to direct the MBP or fragment thereof to a site where a product of fibrillization tends to accumulate. In a preferred embodiment, the fibrillizing peptide is Aβ.

In still other embodiments, the disruptive effect of MBP is exploited to treat a subject having a disease or disorder that is susceptible to treatment by disrupting a product of fibrillization, the product comprising a fibrillizing peptide. Preferred methods comprise administering to the subject an effective amount of a myelin basic protein ("MBP") in a pharmaceutically acceptable vehicle. In various embodiments the vehicle may be as simple as physiological saline, or as elaborate as a liposomal preparation, for example. Optionally, the administering may be adapted to direct the MBP to a site where a fibrillizing peptide tends to accumulate or has accumulated.

In one embodiment, the invention provides a method for treating or preventing a disease in a subject, the disease characterized by a fibrillization of a fibrillizing peptide, the method comprising administering to the subject a vector comprising a nucleic acid encoding an amino acid sequence of MBP or a variant thereof, or a fragment of MBP or a variant of the fragment, operatively associated with a promoter.

In one embodiment, the vector is administered to the brain. In some embodiments, a craniotomized subject is provided and the vector, in a pharmaceutically acceptable vehicle, is injected into the ventricles or the parenchyma of the brain. In some embodiments, the vector is administered to the brain via the vasculature.

In alternative embodiments, the disease or disorder is selected from the group consisting of Alzheimer's disease, Lewy body dementia, and cerebral amyloid angiopathy.

In one embodiment, the invention provides a fragment of MBP having a peptide composition comprising the amino acid sequence KRGX$_1$X$_2$X$_3$X$_4$X$_5$X$_6$HP, wherein X$_1$-X$_6$ are amino acids selected from the group consisting of G, P, A, V, L, I, M, C, F, Y, W, H, K, R, Q, N, E, D, S and T (SEQ ID NO: 1). In one embodiment, the peptide composition is selected from the group consisting of KRGSGKDSH$\underline{H}$P (SEQ ID NO:2), KRGRKQCKTHP (SEQ ID NO:3) and KRGSGKVPWLK (SEQ ID NO:4).

In some embodiments, the invention provides a conjugate composition comprising a fragment of a myelin basic protein that is capable of binding with a fibrillizing peptide. The conjugate further comprises, in linkage with the fragment, an agent selected from the group consisting of a therapeutic agent and a marking agent. In various embodiments of the invention, the conjugate contacts the fibrillizing peptide, thereby binding the agent to the peptide. The agent comprising the conjugate may be a modulating substance.

In one embodiment, the invention provides a method for preventing an amyloid disease, the method comprising: a) providing a subject at risk for an amyloid disease, and b) administering an interfering amount of an interfering fragment of MBP to said subject.

In one embodiment, the fragment is administered into a ventricle or into the parenchyma of the brain of a craniotomized subject.

In one embodiment, the fragment is administered peripherally.

In one embodiment the peripherally administered fragment sequesters a circulating fibrillizing peptide.

In some embodiments, the method for preventing an amyloid disease further comprises administering an interfering amount of an MBP or a fragment thereof contacted or mixed with a modulating substance. In some embodiments, the method comprises administering the modulating substance to the subject. Optionally, the administering may be adapted to direct the MBP or the MBP fragment to or near a site where the fibrillizing peptide is expressed. Optionally, the administering may be adapted to direct the MBP or the MBP fragment to or near a site where a fibrillizing peptide or a product of fibrillization accumulates.

In one embodiment, the invention provides a vector comprising a nucleic acid encoding an amino acid sequence of an interfering fragment of MBP, operatively associated with a promoter. In alternative embodiments, the vector is a viral vector, preferably replication deficient.

In one embodiment, the invention provides a method for preventing an amyloid disease in a subject, the method comprising administering to the subject a vector comprising a nucleic acid encoding an amino acid sequence of an interfering fragment of MBP, operatively associated with a promoter.

In one embodiment, the vector is administered to the brain. In some embodiments, a craniotomized subject is provided and the vector, in a pharmaceutically accepD vehicle, is injected into the ventricles or the parenchyma of the brain. In some embodiments, the vector is administered to the brain via the vasculature.

In some embodiments, the interfering fragment is a peptide wherein the amino acid sequence is selected from the group consisting of SEQ ID NO:2, SEQ ID NO:3, and SEQ ID NO:4

In some embodiments, the fibrillizing peptide is in an environment selected from the group consisting of in vitro, in situ and in vivo.

In preferred embodiments, the fibrillizing peptide is amyloid-beta peptide.

In alternative embodiments, the disease or disorder is selected from the group consisting of Alzheimer's disease, Lewy body dementia, and cerebral amyloid angiopathy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 shows the amino acid sequences in single-letter code (See Table 1) (SEQ ID NOS: 45-48) for recombinantly expressed and purified fragments of MBP.

FIG. 4A-D illustrates the binding of the MBP fragments of FIG. 3 to the Dutch/Iowa CAA Aβ40 mutant and wild-type Aβ2 by surface plasmon resonance. FIG. 4A: MBPI (the only fragment to exhibit binding); FIG. 4B: MBP2; FIG. 4C: MBP3, and FIG. 4D: MBP4.

FIG. 8A shows 6-h time course of Aβ40WT and Aβ40DI fibril formation measured by thioflavin T fluorescence. Data represent the means±S.D. of triplicate samples. FIG. 8B and FIG. 8C show representative TEM images of Aβ40DI and Aβ40WT, respectively, after 6 h of incubation. A.U., arbitrary units.

In FIG. 9A and FIG. 9B, sections were immunostained with anti-Aβ mAb 66.1. In FIG. 9C and FIG. 9D, fibrillar amyloid was detected by staining with thioflavin S. Scale bars=50 μm.

FIGS. 10A&B shows Isolation of human brain proteins that selectively bind to CAA mutant forms of Aβ. Homogenates were prepared from normal human brain frontal cortex and passed through affinity columns prepared from wild-type (FIG. 10A) or Dutch/Iowa CM double mutant (FIG. 10B) Ap40. Aliquots of each fraction from each column were analyzed by SDS-PAGE and silver staining. The arrowhead designates a prominent band of ~20 kDa that was eluted from the Dutch/Iowa Aβ column (lane 6), but not from the wild-type Aβ column (lane 3). A band identified at ~65 kDa also specifically eluted from the CAA mutant Aβ40DI column. Lanes 1 and 4, brain homogenate load; lanes 2 and 5, column flow-through (FT) and wash; lanes 3 and 6, column eluates.

FIG. 12A shows immunoprecipitated samples from left to right: MBP alone, MBP incubated with Aβ40WT, MBP incubated with Aβ40DI, Aβ40WT alone, and Aβ40DI alone. FIG. 12B shows Western blot controls from left to right: Aβ40WT, Aβ40DI, and MBP. FIG. 12C hows representative dot blot analysis of MBP binding to Aβ and control peptides. APP, AβPP. FIG. 12D shows quantitation of MBP binding to peptides by dot blot analysis. Data represent the means±S.D. (n=4 for each peptide). Bar 1, Aβ40DE bar 2, Aβ40WT; bar 3, AβPP-(744-763); bar 4, AβPP-(100-119); bar 5, insulin. A.U., arbitrary units.

FIG. 14A shows Successive scans of Ap42WT incubated at 37° C. taken at 0 h (□), 6 h (□), 12 h (□), 24 h (□), 36 h (□). FIG. 14B shows Absolute values at 215 nm charted from successive scans. Aβ42 (□), MBP (□), Aβ42 with MBP (□). FIG. 14C shows a single scan of Aβ42WT with MBP at 48 h (black) compared to a single scan of mature Aβ42WT fibrils spiked with MBP at 48 h (gray).

FIG. 15A shows IR absorbance in the Amide I band for Aβ42WT alone (black line) or with MBP (gray line) incubated at 37° C. at 24 h.

FIG. 17A-F shows Quantitative immunoblot analysis of MBP inhibition of Aβ40DI fibril assembly in vitro. Aβ40DI (12.5 μM) was incubated in the absence (A and D) or presence (C and F) of 1.56 11M purified MBP. Bovine a-lactalbumin (Lalb. 1.56 μM) was included as a negative control (B and E). Aliquots were removed at specific time points and analyzed by quantitative immunoblot analysis using anti-Aβ mAb 6E10. FIG. 17A shows representative immunoblot of Aβ40DI incubated alone for up to 12 h; FIG. 17B shows representative immunoblot of Aβ40DI incubated with bovine α-lactalbumin for up to 12 h; FIG. 17C shows representative immunoblot of Aβ40DI incubated with MBP for up to 12 h; FIG. 17D-F show relative abundance of low, mid, and high molecular mass species of Aβ40DI as determined by quantitative immunoblot analysis in the absence (FIG. 17D) or presence of bovine a-lactalbumin (FIG. 17E) or MBP (FIG. 17F). Data represent the means±S.D. of three separate experiments.

FIG. 26 FIG. 4.10 1H-15N HSQC of MBP1 interaction with Aβ40WT. A. Uniformly labeled 15N-MBP1 measured with (red) and without (black) Aβ40DI. B. Uniformly labeled Aβ40WT measured with (red) and without (black) MBP1. C. MBP1 sequence with the locations of residues (red) found to shift in the presence of Aβ40DI. D. Sequence of Aβ40WT with the locations of residues (red) found to shift in the presence of MBP1. SEQ ID NOS: 49-50.

FIG. 27 shows mapping of MBP antibodies. Polyclonal goat and monoclonal mouse antibodies were generated against the sequence RGAPKRGSGKDSHHP (SEQ ID NO: 51) corresponding to MBP50-64 a fragment designated MBP1. Alanine mutations of specific residues of MBP50-64 were prepared in the MBP1 fragment. Quantitative ELISA analysis was performed and the amount of antibody binding to each mutant was compared to native wild-type MBP1. This showed that mutagenesis of residues H63 and P64 completely abolished binding of all antibodies while mutagenesis of residues K59 and D60 markedly lowered antibody binding of mAb3B8 and the goat pAb. On the other hand, mAb3B9 appears to be more focused towards the extreme C-terminal end of this MBP sequence. These finding indicate that each of the antibodies is selectively targeted towards the region KDSHHP (SEQ ID NO: 52) of MBP.

DETAILED DESCRIPTION

Figure 1:
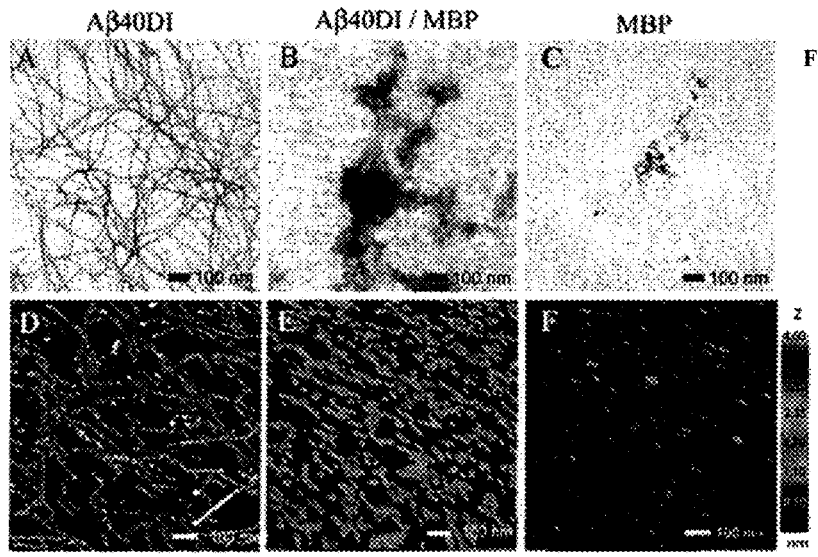
FIG. 1A-F shows the inhibition of fibrillization of Dutch/Iowa CAA mutant Aβ40 (Aβ40DI) as determined by transmission electron microscopy ("TEM") (FIG. 1A, FIG. 1B and, for MBP alone, FIG. 1C) and single-touch atomic force microscopy ("AFM") (FIG. 1D, FIG. 1E and, for MBP alone, FIG. 1F).

In general, the terms used herein comport with their usage by persons of skill in the field of the present invention. To facilitate an understanding of the embodiments of the invention as herein described, a number of terms, set off in quotation marks in this specification, are further explained herein. As used in this specification and its appended claims, terms such as "a", "an" and "the" are not intended to refer to only a singular entity, but include the general class of which a specific example may be used for illustration, unless the context dictates otherwise. The terminology herein is used to describe specific embodiments of the invention, not to limit the scope of the invention.

Embodiments of the present invention use myelin basic proteins ("MBPs"), which will be understood to include genetic variants (mutations) and fragments thereof, to disrupt aggregations of fibrillizing peptides. Other embodiments use MBPs to prevent aggregations from forming. The term "disrupt," however, as used herein, is not intended to exclude "formation" or vice versa, since embodiments of the invention are not limited by any theory as to precisely how aggregates form or what dynamics may then govern their maintenance. In preferred embodiments, the invention employs MBPs to treat amyloidoses, particularly amyloidoses associated with anomalies in the metabolism of Aβ-42 and/or Aβ-40 mutants. An "anomaly in metabolism," as used herein, encompasses any production or accumulation, in any form, of Aβ-42 peptide and/or Aβ-40 mutant peptide in a cell or tissue of a subject, which production or accumulation a person of skill in the healing arts deems to be pathogenic or pathological. The term is intended to include any condition deemed to indicate that the subject has a propensity for such an anomaly.

"Fibrillization," as used herein, refers to a process that drives certain peptides to aggregate, ultimately to form complex, often heterogenous, and typically insoluble structures. Peptides susceptible to this process, often called "amyloid peptides," are also referred to herein as "fibrillizing peptides."

As monomers, fibrillizing peptides are soluble in water and body fluids but tend to aggregate or "assemble," apparently spontaneously by a process known as intennolecular self-assembly. An "aggregation" of a fibrillizing peptide exists in any domain occupied by a plurality of intact peptide monomers that cannot be said to be simply "dissolved" (i.e., homogenously distributed) in that domain. All such aggregations are "products of fibrillization" herein. Some fibrillizing peptide monomers, Aβ in particular, aggregate in the sense that the monomers form relatively stable oligomers (i.e., aggregations wherein monomers are bonded but few in number) that tend, also, to be soluble. The process of oligomerization may be monitored, for example, by a method described by Pray (U.S. Patent Application Publication No. 2008/0113444, incorporated herein in its entirety by reference for all purposes). The toxicity of these monomers may be evaluated, in vitro, by assaying caspase-3 activation, for example (Costa et al., FEBS Letters 582:936-942, 2008) and, in vivo, by any number of indices of neuro-degeneration known in the art. Indeed, as used herein, a "toxic" effect relates to any process or condition that tends toward disease, whether or not symptoms thereof are manifest.

A "diffuse aggregation," or "diffuse plaque," used interchangeably herein, refers to a population of fibrillizing peptide molecules assembled into an insoluble deposit having no discernible secondary structure. Secondary structure develops as the molecules orient themselves (evidently by intramolecular, i.e., "intrapolymer," self-assembly) in strands lying side-by-side and attached by hydrogen bonds to form a so-called "β-sheet" that tends to grow along one axis into a "fibril." Fibrils are insoluble in aqueous solutions. That is, the monomers (and, perhaps, oligomers) that comprise them do not spontaneously return to their solvent as "solute" molecules. The fibrils tend to become entangled with one another to form "fibrillar tangles" and "dense core plaque," a late step in the process of fibrillization. Diffuse and dense core plaque, which may be referred to as "deposits" or "amyloid deposits," are insoluble. As used herein, the term "insoluble" is to be understood as a relative tetra that allows for diffusion of molecules from the solid state and for solids that are in a steady state with molecules in solution.

An "amyloid disease," as used herein, is a disease characterized by a product of fibrillization. It is not intended, however, that the diagnosis of an amyloid disease, or its treatment, or the outcome of such treatment must depend on finding evidence of a product of fibrillization in the subject. Embodiments of the invention may be practiced without having any such evidence in hand.

Intermolecular forces holding fibrillizing peptides together in insoluble deposits or plaques is an aspect of fibrillization as is the intermolecular force that urges soluble monomers to aggregate. With respect to Aβ, a distinction is often drawn between "disruption" of fibrils and plaque and "prevention" of fibril and plaque formation: In the former, the Aβ molecules won't dissolve; in the latter, they are in solution, so fibril formation is preventable. It will be understood that prevention of fibrillization need not be total to constitute a prevention' as used herein. Likewise, it is to be understood that "disruption" need not be complete to constitute a disruption as the term is used herein. The extent to which fibrillization has formed insoluble aggregates (or, interchangeably herein, "aggregations") and, correspondingly, the extent to which disruption has reduced such aggregates, may be evaluated by, for example, measuring in appropriately designed experiments the "thioflavin load" in the brain tissue of experimental animals (Schmidt et al., Am. J. Pathol. 147: 503-515, 1995).

MBP refers herein to a protein involved in the myelination of nerves in mammalian subjects. In mammals, various forms of MBP exist which are produced by the alternative splicing of a single gene; these forms differ by the presence or the absence of short (10 to 20 residues) peptides in various internal locations in the sequence. The major form of MBP is generally a protein of about 18.5 Kd (170 residues). MBP is the target of many post-translational modifications: it is N-terminally acetylated, methylated on an arginine residue, phosphorylated by various serine/threonine protein-kinases, and deamidated on some glutamine residues.

Myelin basic protein is encoded by a member of a large family of developmentally regulated genes called the Golli complex (genes of the oligodendrocyte lineage) (Campagnoni et al., J. Biol. Chem. 268:4930-4938, 1993, Pribyl et al., Proc. Natl. Acad. Sci. U.S.A. 90:10695-10699, 1993, Givogri et al., J. Neurosci. Res. 59:153-159, 2000). Members of this family are involved in the formation and maintenance of myelin sheaths. However, Golli proteins are also found in fetal spinal cord, thymus, spleen, and in cells derived from the immune system (Givogri et al., J. Neurosci. Res. 59:153-159, 2000), as well as in neurons (Tosic et al., Glia 37:219-228, 2002), Pribyl et al., J. Comp. Neurol. 374:342-353, 1996). The Golli locus contains two distinct start sites under independent regulation and consists of 11 exons that can be alternatively spliced to form the various Golli-MBPs. Included are seven exons that encode the proteins (Pribyl et al., Proc. Natl. Acad. Sci. U.S.A. 90:10695-10699, 199). The major species are 21.5, 20.2, 18.5, and 17.2 kDa (Roth et al., J. Neurosci. Res. 17:321-328, 1987). The 21.5-, 20.2-, and 17.2-kDa isoforms are found in fetal and developing brains. In adults, the 18.5- and 17.2-kDa isoforms are predominant (Baumann and Pham-Dinh, Physiol. Rev. 81:871-927, 2001).

The Golli-MBPs exhibit little intrinsic structure, so they are probably unfolded in their native state (Moscarello, Prog. Clin. Biol. Res. 336:25-48, 1990, Smith, J., Neurochem. 59:1589-1608, 1992). At least eight charge isomers have been shown to exist for the 18.5-kDa isoform. These result from deamidation, phosphorylation, C-terminal arginine loss, and the deimination of arginyl residues (Chou et al., J. Biol. Chem. 251:2671-2679, 1976). In many cases, these post-translational modifications are thought to regulate myelin assembly, MBP-ligand interactions, and signaling functions (Zand et al., Biochemistry 37:2441-2449, 1998). MBP interacts with many different ligands, including lipids (Smith, J., Neurochem. 59:1589-1608, 1992, Wood and Moscarello, J. Biol. Chem. 264:5121-5127, 1989), calmodulin (Polyerini et al., J. Struct. Biol. 148:353-369, 2004), divalent cations (Berlet et al., Neurosci. Lett. 179:75-78, 1994), GTP (Chart et al., Biochem. Biophys. Res. Commun. 152:1468-1473, 1988), and cytoskeletal proteins such as tubulin (Pirollet et al., Biochemistry 31:8849-8855, 1992) and actin (Hill and Harauz, Biochem. Biophys. Res. Commun. 329:362-369, 2005). The binding of MBP to tubulin and actin is believed to stabilize their polymerization, which is essential to the formation of myelin sheaths (Richter-Landsberg, J. Neurosci. Res. 59:11-18, 2000).

It is not intended that the invention be limited by any theory that seeks to explain how MBPs disrupt amyloid plaque or its formation from monomers or oligomers of Aβ. Applicant, however, has adduced evidence to support the previously unknown fact that myelin basic protein is a protease, i.e., an enzyme that catalyzes the lysis of another peptide by hydrolytically cleaving a peptide bond within the peptide ("proteolysis"). Accordingly, Applicant believes that when a fibrillizing peptide is contacted with an MBP, the MBP can catalytically cleave the fibrillizing peptide, which disrupts the peptide in such a way that it no longer has the structural requirements to participate in fibrillization.

Myelin basic protein is known essentially as a structural protein, a component of the lipoprotein complex that comprises myelin membranes. Myelin membranes are highly specialized cell membranes elaborated by glial cells. They wrap around the axonal portion of neurons to form a multi-layered sheath that insulates the electrically conductive axon from its immediate environment. It is especially curious, therefore, to find that this "structural" protein of the nervous system is also an enzyme whose substrate, Aβ, is so strongly implicated in the pathology of the central nervous system.

In the case of Aβ in particular, in the view of the inventor, proteolysis by MBP not only prevents or retards fibrillization by removing properly configured monomers from solution, but may also promote disruption of insoluble Aβ fibrils by depriving the fibrils of the structural integrity that a full complement of intact Aβ molecules affords.

Both nature and man employ proteases to dissolve, disaggregate, "digest" or otherwise disrupt proteinaceous materials (e.g., M. J. Anderson et al., Molec. Cell. Biol. 16:4972-4984, 1996) by catalytically breaking down peptide bonds therein through hydrolysis. With the breakage comes a disorganization of the molecular structural arrangement that would otherwise maintain the fibrillized state. Proteases are generally classified as either exopeptidases that cleave amino acids from the ends of a protein, or as endopeptidases that cleave peptide bonds within the protein. Some proteases recognize specific sequences and cleave proteins only once or twice. Others degrade proteins completely into individual amino acids. Some are secreted and cause the destruction of proteins and aggregates thereof in extracellular materials. Others are secreted into specific sites, such as the stomach, where they break down proteins, such as those present in foods, at the relevant site. Still others are involved in regulating physiological processes via biological cascades. Proteases may be expressed intracellularly or extracellularly. They may anchor themselves reversibly to cell membranes or may be integral to the membrane.

Diverse processes within the body rely on proteolysis. Proteases modulate apoptosis (caspases) (Salvesen and Dixon, Cell 91:443-46, 1997), participate in the control of blood pressure (renin, angiotensin-converting enzymes) (van Hooft et al., New Engl. J. Med. 324:1305-11, 1991, and chapters 254 and 359 in Barrett et al., Handbook of Proteolytic Enzymes, Academic Press, San Diego, 1998) play roles in tissue remodeling and tumor invasion (collagenase) (Vu et al., Cell 93:411-22, 1998, Werb, Cell 91:439-442, 1997), protein turnover and cell-cycle regulation (proteosorne) (Bastians et al., Mol. Biol. Cell. 10:3927-41, 1999, Gottesman, et al., Cell 91:435-38, 1997, Larsen et al., Cell, 91:431-34, 1997), inflammation (INF-α convertase) (Black et al., Nature, 385:729-33, 1997), and in protein turnover (Bochtler et al., Annu. Rev. Biophys. Biomol. Struct. 28:295-317, 1999).

Generally, a polypeptide that exhibits "protease activity" or "proteolytic activity" refers to a protein that has the ability to catalyze the hydrolysis of a peptide bond. In general, the catalytic event is effected by a relatively few amino acids in the polypeptide that interact with one another and with the substrate (i.e., the reactant(s) in the chemical reaction that an enzyme catalyzes). These amino acids comprise the "active domain," or "catalytic domain" of the protease. The term "catalytic site" generally refers to one or a few amino acids in a substrate for a protease. These amino acids define the site at which the protease attacks the substrate. The term "catalytic activity" refers to the rate at which a catalytic domain cleaves a substrate. The term "substrate" as used herein refers to a molecule (a polypeptide, protein or other molecule known to one skilled in the art) upon which a catalyst (a protease unless otherwise noted) acts.

MBP's proteolytic effect on Aβ is not intended to rule out the existence of other MBP-related phenomena that may affect fibrillization. Applicant, using a combination of immunoaffinity chromatography, mass spectrometry and surface plasmon resonance techniques, and ultrastructural inspection, has shown that MBP binds to Aβ (Roos et al., Journal of Biological Chemistry 282:9952-9961, 2007). Moreover, MBP does so more avidly with the Dutch/Iowa CAA double mutant form of Aβ than with wild-type Aβ. Interestingly, the mere binding of MBP to CAA mutant Aβ inhibits its assembly into fibrils, suggesting that the portion of the molecule that represents the molecule's binding domain, even apart from the molecule's proteolytic function, would likely have advantages over the full-length molecule, especially for therapeutic applications. Indeed, Applicant has identified several fragments of MBP that disrupt amyloid plaque or its formation from monomers or oligomers of Aβ. Again, without intending to limit embodiments of the invention by any theory as to how they work, Applicant believes that when a fibrillizing peptide binds with an MBP fragment, the bound form of the monomer/oligomer becomes "disfigured" in such a way that it no longer has the structural requirements to participate in fibrillization.

Accordingly, some embodiments of the present invention use fragments of MBP, which will be understood to include genetic variants (i.e., mutations) thereof, to prevent aggregates of fibrillizing peptides from forming or to otherwise disrupt them. As used herein, a "fragment" of a protein encompasses any sequence of amino acids that (1) matches a sequence of amino acids within a given protein and (2) is shorter than the protein by at least one amino acid residue. The term "match," as used herein, encompasses any sequence that does not, in a sequence that otherwise would provide an "interfering fragment" (i.e., a fragment that interferes with a fibrillization of a fibrillizing peptide), contain an amino acid that inhibits the interference. In other words, a "match" need not be an identical match. Homologous sequences that do not erase function in the fragment are treated as matches. Such fragments may be referred to herein, interchangeably, as "interfering fragments" or "functional fragments." A fragment is functional if it inhibits (i.e., "interferes with" or reduces the rate at which an action proceeds) the formation of (1) complexes of fibrillizing peptide bound to the fragment, (2) peptide oligomers, or (3) peptide fibrils. In preferred embodiments, the fragment forms a complex by binding with Aβ. In the most preferred embodiments the fragment comprises the motif $KRGX_1X_2X_3X_4X_5X_6HP$ (SEQ ID NO: 1).

The Aβ B binding properties of the exemplary fragments of MBP described herein were determined in a thioflavin T fluorescence assay as follows: Lyophilized Aβ peptides were first resuspended with Me2SO to 2.5 mM, diluted to 12.5 µM in PBS, and then incubated at 37° C. with rocking either alone or with 1.56 µM MBP or bovine α-lactalbumin. Control samples containing 0.5% Me2SO and 1.56 µM MBP or lactalbumin in PBS were also included. At each time point, 100 µl samples of each reaction were placed in a 96-well microplate in triplicate, and 5 µl of 100 M thioflavin T was added. The plate was mixed and incubated at 22° C. in the dark for 10 min. Fluorescence was measured at 490 nm with an excitation wavelength of 446 nm in a SpectraMax spectrofluorometer (Molecular Devices, Sunnyvale, Calif.) using SoftMax Pro control software. It is apparent that the method enables persons of skill in the art to determine the binding properties of MBP, variants thereof, and fragments thereof for any Aβ-peptide, including mutants thereof.

To evaluate the effects of MBP, variants thereof, fragments thereof, and modulators thereof, on plaque formation in vivo, the artisan may employ an immunochemical method such as those used in the development of embodiments of the instant invention, an example of which follows:

Tg2576 and Tg-SwDI transgenic mice were killed at 24 months, and the brains were removed and bisected through the mid-sagittal plane. Cerebral hemispheres were immersion-fixed with 70% ethanol overnight and subjected to increasing sequential dehydration in ethanol, followed by xylene treatment and embedding in paraffin. Sagittal sections were cut at 10 µm thickness using a microtome, placed in a flotation water bath at 45° C., and then mounted on ColorFrost Plus slides (Fisher). Paraffin was removed from the sections by washing with xylene, and the tissue sections were rehydrated in decreasing concentrations of ethanol. Antigen retrieval was performed by treatment with proteinase K (0.001 mg/ml) for 5 min at 22° C. Immunostaining was performed using anti-AβmAb 66.1 (1:300 dilution). Primary antibody was detected with horseradish peroxidase-conjugated anti-mouse IgG and visualized with a stable diaminobenzidine solution (Invitrogen). Detection of fibrillar amyloid was performed by incubating the sections with 1% thioflavin S in PBS in the dark for 5 min at 22° C., followed by washing three times (3 min each) with 50% ethanol. Images were captured using an Olympus BX60 optical microscope and an Olympus DP10 charge-coupled device camera.

For some embodiments of the invention, it may be advantageous to work with purified isolates of mutant and wild-type forms of Aβ. The affinity chromatography method used in the development of embodiments of the instant invention to obtain such isolates is exemplary: To prepare affinity resins, biotinylated wild-type Aβ40 peptide (Aβ40WT) and Aβ40DI were each redissolved in 20 mM NaHCO$_3$ buffer (pH 8.5) and applied to ImmunoPure immobilized streptavidin beads (Pierce) following the manufacturer's instructions. Immobilized ligands were cross-linked with 2 mM bis(sulfosuccinimidyl) suberate (Pierce) for 30 min with rocking at room temperature in 20 mM NaHCO3 (pH 8.5). Crosslinking reactions were stopped by the addition of 1 M Tris-HCl (pH 7.4) to a final concentration of 20 mM. Homogenates of normal human brain frontal cortex (which may obtained as biopsies) were prepared in Tris-buffered saline (50 mM Tris-HCl and 200 mM NaCl (pH 7.4)) containing complete protease inhibitor cocktail (Roche). Homogenates were centrifuged at 12,000×g for 30 min, and supernatants were loaded onto Tris-buffered saline-equilibrated affinity columns (0.8×4 cm) under gravity flow. After extensive washing, the columns were eluted with 0.2 M glycine and 0.15 M NaCl (pH 2.7) and collected into tubes containing 200 mM Tris-HCl, 50 µM iodoacetate, 50 µM 4-(2-aminoethyl)benzenesulfonyl fluoride, 50 µM EDTA, and 50 µg/ml leupeptin. Fractions were analyzed by SDS-PAGE on 10-20% Tris/glycine gradient gels. All runs were carried out at 4° C. Three separate affinity chromatography runs were carried out for each column ligand.

Protein bands separated by SDS-PAGE as outlined above were excised from the polyacrylamide gels and digested overnight with sequencing-grade trypsin in situ at 37° C. Samples were run on a Voyager-DE STR MALDI-TOF mass spectrometer (Applied Biosystems) operating in the reflector mode. Samples were dissolved in a 50% solution of acetonitrile and 0.1% trifluoroacetic acid containing α-cyano-4-hydroxycinnamic acid (5 mg/ml) and dried on the sample plate. A nitrogen laser operating at 337 nm was used to ionize the sample. The accelerating voltage was set to 20 kV employing a 275-ns delay before introduction of ions into the flight tube of the mass spectrometer. The mass scale (m/z 500-5000) was calibrated with a mixture of peptides (400 fmol/l), and ~100 laser shots were used to produce each spectrum. Peak lists were submitted to the Mascot search engine with no taxonomy limitation and a peptide tolerance set to 100 ppm.

Immunological analyses may also be advantageous. The methods used herein included the following:

Immunoblot Analysis.

Briefly, samples were heated at 90° C. for 5 min in reducing SDS-PAGE loading buffer, loaded onto gels, and electrophoresed. Gels were transferred to Hybond ECL nitrocellulose membranes (Amersham Biosciences) at 50 V overnight at 4° C. Membranes were blocked in PBS containing 5% milk or bovine serum albumin (BSA; used with biotinylated primary antibodies) at room temperature for 1 h and washed 3×10 min with PBS and 0.05% Tween 20. Membranes were incubated with primary antibodies for 1 h and washed as described above. Next, the membranes were incubated with either horseradish peroxidase-conjugated sheep anti-mouse IgG or horseradish peroxidase-conjugated streptavidin (both from Amersham Biosciences) for 1 h and washed. Detection was accomplished using ECL Western blotting substrate (Pierce), and images were captured either on film or using a VersaDoc 3000 imaging system (Bio-Rad) and quantitated with the manufacturer's Quantity One software.

Co-Immunoprecipitation.

AP peptides were resuspended in Me2SO to 2.5 mM and used at 10.8 µM. MBP was used at 1.56 µM. Proteins were combined in 250 µl of incubation buffer (PBS, 0.05% Tween 20, and 1% BSA). Anti-MBP mAb 382 was added to each sample mixture and incubated for 1 h at 4° C. with rocking. After incubation, 20 µl of washed GammaBind protein G-Sepharose beads (Amersham Biosciences) were added to each mixture, followed by incubation for an additional 1 h at 4° C. with rocking. Beads were separated by centrifugation at 8000×g for 2 min. Supernatants were removed, and beads were washed with 1 ml of incubation buffer. Separation and washing were repeated three times. A final wash was performed in PBS and 0.05% Tween 20 to remove excess BSA. Centrifuged beads were combined with 25 µl of reducing SDS-PAGE loading buffer and heated as described above. 10 µl of each sample/loading buffer mixture was loaded onto 10-20% Tricine gels (Invitrogen) and electrophoresed at 125 V for 35 min. Immunoblotting was carried out as described above using either biotinylated anti-MBP mAb 384 or biotinylated anti-Aβ mAb 3D6 as primary antibody. Experiments were performed in triplicate.

Dot Blot Analysis.

Aβ peptides and the AβPP-(744-763) and AβPP-(100-119) peptides (Multiple Peptide Systems, San Diego, Calif.) were diluted to 2 µg/ml in Tris-buffered saline from 10 mg/ml Me2SO stock solutions. Insulin (Sigma) was resuspended to 2 mg/ml in water at pH 2.0 and diluted to 2 µg/ml in Tris-buffered saline. 1 µg of each was immobilized onto Hybond ECL nitrocellulose membranes using a Bio-Dot microfiltration apparatus (Bio-Rad) according to the manufacturer's instructions. Each membrane was removed from the apparatus following immobilization and blocked overnight in 5% BSA and PBS at 4° C. The membrane was then incubated in 1 g/ml MBP in 5% BSA, PBS, and 0.05% Tween 20 for 2 h at room temperature. The membrane was washed 3×10 min with 5% BSA, PBS, and 0.05% Tween 20 and incubated with mAb 384 (1:2000 dilution) for 1 h at room temperature. The membrane was next washed 3×10 min with PBS and 0.05% Tween 20 and incubated with horseradish peroxidase-conjugated sheep antimouse IgG (1:2000 dilution) for 1 h at room temperature. Detection and quantitation were performed as described above.

Several embodiments of the invention turn on measuring the rate of fiber assembly under specified conditions. Surface plasmon resonance provides such a method, and is well-known in the art. Plasmons are electromagnetic waves that exist only on a metal surface. They are not lightwaves but they propagate under the influence of lightwaves and, when a propagating plasmon hits an "irregularity" on the surface, light may be emitted. The technique works because these emissions can be detected by various means and related to the specific structure that gives rise to the irregularities that arrest the propagating plasmons. A plasmon resonance method adaptable for use in embodiments of the instant invention is described in U.S. Pat. No. 5,981,167, incorporated herein by reference in its entirety for all purposes. The protocol used herein is described as an example:

All runs were performed on a Biacore 2000 instrument using 10 mM HEPES (pH 7.4), 150 mM NaCl, 3 mM EDTA, and 0.005% (v/v) Tween 20 as running buffer and diluent. Streptavidiri was conjugated to the surface of three flow cells of a CM5 chip at 10 µl/min using amine coupling chemistry to a final average response level of 1890.2 response units. N-terminally biotinylated Aβ peptides were resuspended in Me2SO to 2.5 mM and serially diluted to 13 nM immediately before application. Biotinylated Aβ40WT and Aβ40DI were bound to individual flow cells at 10 µl/min to achieve an average relative response level of 157.1 response units, leaving flow cell 1 as reference. This chip preparation procedure was found to result in a surface that minimized mass transfer effects for kinetic interaction experiments. The resultant Rmax of these surfaces was ~700 response units with MBP as analyte. Purified MBP was passed over all four flow cells at 5, 10, 25, 50, and 100 nM at a flow rate of 30 µl/min for kinetic measurements. Faster flow rates did not significantly improve the quality of data. Surfaces were regenerated with 0.2 M glycine (pH 2.0) and 150 mM NaCl between runs. The resulting sensorgrams were analyzed by BIAanalysis software. Triplicate concentration series were used for each surface.

Artisans may also make determinations regarding the assembly of Aβ into oligomers and fibrils by means of transmission electron microscopy and atomic force microscopy. Examples are provided:

For electron microscopy, a 20 µl aliquot of the sample mixture was deposited onto a Formvar-coated copper mesh grid. The sample was allowed to stand for 60 s, and excess solution was wicked away. The samples were negatively stained with 2% (w/v) uranyl acetate. The excess stain was wicked away, and the sample was allowed to dry. The samples were viewed with an FEI Tecnai 12 BioTwin transmission electron microscope, and digital images were taken with an Advanced Microscopy Techniques camera.

Atomic force microscopy ("AFM") was carried out using a lifeScan controller (LifeAFM Inc., Port Jefferson, N.Y.) interfaced with a MultiMode microscope (Digital Instruments, Santa Barbara, Calif.) fitted with an E seamier. With this instrument configuration, only a single contact of the AFM probe is made with the sample per pixel. Computer control of the cantilever position and angle during approach allows for detection of the sample height with minimum cantilever deflection, allowing for a minimum compressive force (30-100 piconewtons/nm) applied to the sample. AFM samples were prepared by adsorbing 20 µl of sample mixture to freshly cleaved ruby mica (S & J Trading, Inc., Glen Oaks, N.Y.) for 45 min to 1 h. The samples were rehydrated with ultrapure Milli-Q water (Millipore Corp., Billerica, Mass.) and immediately imaged. Samples were imaged using SuperSharpSilicon probes (SSS-CONT, NANOSENSORS, Neuchatel, Switzerland) that were modified for magnetic retraction by attaching samarium cobalt particles. The effective diameter of the SuperSharpSilicon probes was 4±1 nm at a height of 2 nm. Data analysis and graphics were performed using Interactive Display Language Version 5.0 (Research Systems, Inc., Boulder, Colo.). In the Z-scale bars, numbers in each color square indicate the Z-value at the middle of the range for that color.

The formation of β-sheet fibrils may be evaluated by circular dichroism ("CD") spectroscopy. The technique is based on circularly polarized light. The secondary structure of proteins tends to "distort" the polarization toward the elliptical. The degree and direction of the distortion over a range of wavelengths produces spectra that are characteristic of the protein under examination and its secondary structure. One such method, suitable for use in embodiments of the present invention, is summarized below:

Preferably, purified protein is placed in detergent-free, low-salt buffer in a cuvette having a lightpath length on the order of 1 mm. The optimal concentration of the protein may be determined by standard techniques well-known in the art, and confirmed by comparing the spectrum over a range of concentrations, using an instrument (e.g., JASCO) and cuvette properly calibrated with a standard such as d-10-camphorsulfonic acid in water. To acquire a CD spectrum, the sample is scanned over a wavelength range of about 180-260 nm (spectral width approx. 1 nm). A suitable scan rate is of the order of 100 nm/min for a response time of about 2 seconds. Preferably, however, slower scan speeds (e.g., 5 nm/min, response time around 20 seconds) are used to reduce noise.

Infrared spectroscopy to measure so-called "attenuated total reflection" or "ATR" also provides information about a protein's secondary structure. If light impinges on a surface of a light-refracting material at a sufficiently acute angle, it will be "totally reflected" from that surface. However, some of the energy of the wave does, in fact, pass through the surface. This energy, called an "evanescent wave" is not a lightwave because it cannot self-propagate. Therefore, it attenuates over a short distance, a distance made even shorter if it must pass through a material such as a protein lying in its path. The extent of the attenuation reflects certain physical properties of that protein.

Figure 8A:
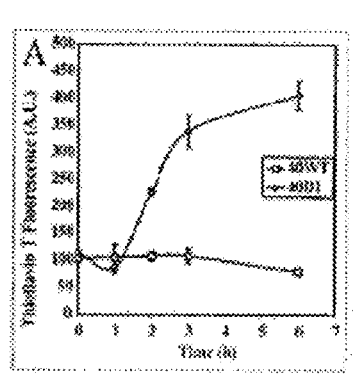
FIG. 8A-C shows rapid fibril assembly of Dutch/Iowa CAA mutant Aβ.
Figure 8B:
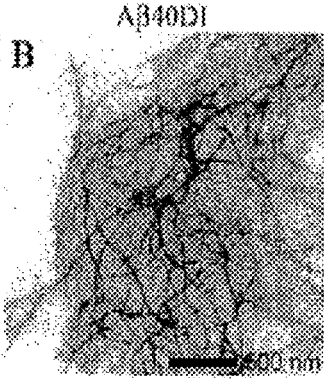
Figure 8C:
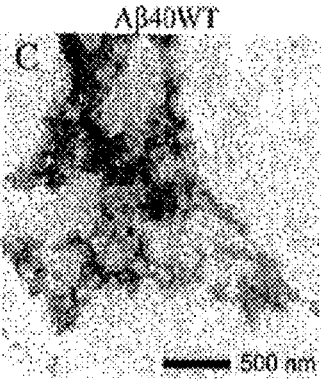
Figure 9A:
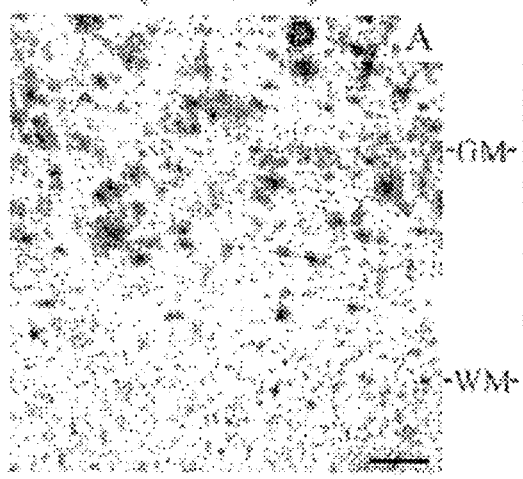
FIG. 9A-D shows Immunohistochemical analysis of Aβ deposition in transgenic mouse brain. Mid-sagittal cross-sections of the brain cortices of Tg2576 (FIG. 9A and FIG. 9C) and Tg-SwDI (FIG. 9B and FIG. 9D) mice at 24 months of age showing both gray matter (GM) and white matter (WM).
Figure 9B:
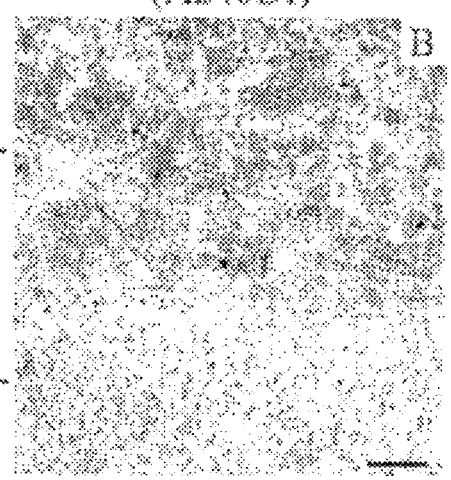
Figure 9C:
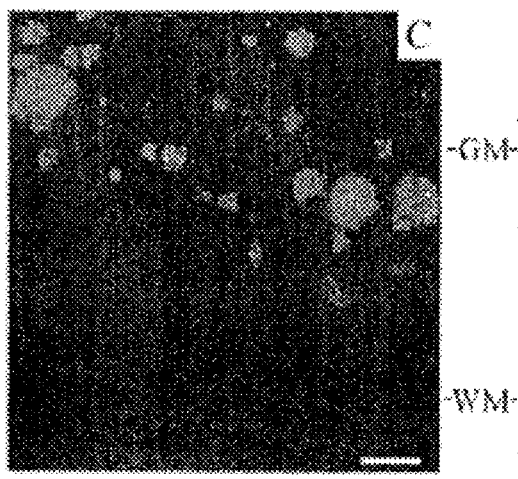
Figure 9D:
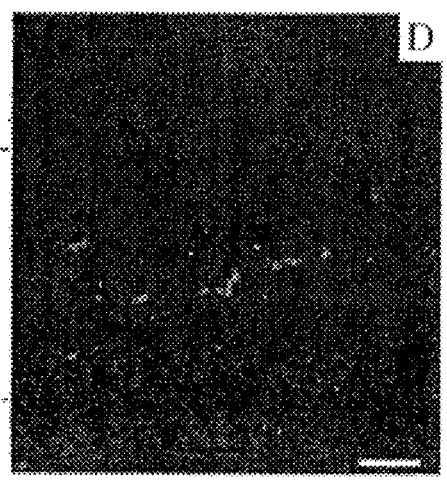

The above-described techniques are best used in combination as exemplified below. The relatively rapid rate of fibril assembly by the double mutant form of Aβ ("Aβ40DI") compared to wild-type Aβ ("Aβ40WT") is biochemically evident as determined by thioflavin T fluorescence (FIG. 8A) and ultrastructurally evident by transmission electron microscopy (FIGS. 8B and C). FIG. 9 supports the utility of immunohistochemistry for evaluating fibril formation. Brain tissue of a transgenic mouse that produces large amounts of Aβ40WT is compared to that of a transgenic strain that expresses Aβ40DI. Consistent with the finding that the double mutant form accumulates in cerebral blood vessels but not in brain parenchyma, one sees immunostaining in Panel A but not in panel B, and this is confirmed by thioflavin staining in panels C and D.

Figure 11:
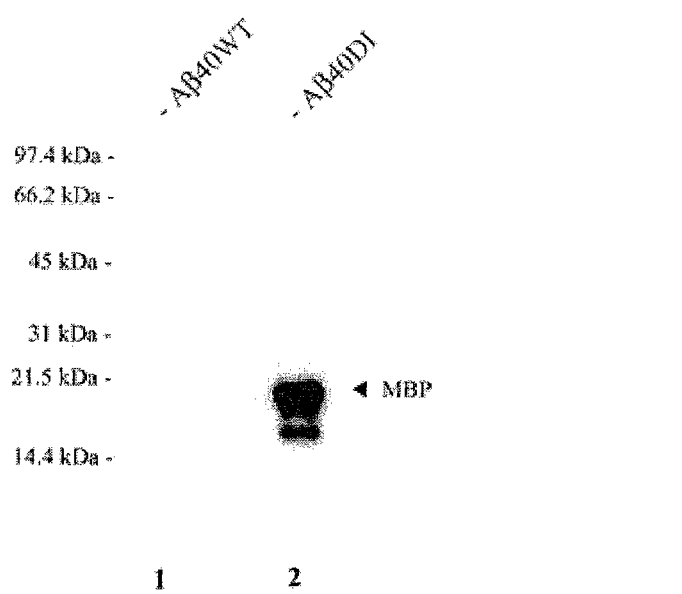
FIG. 11 Immunoblot for MBP in Aβ affinity column eluates. Equivalent amounts of eluates from each affinity column subjected to immunoblotting using mouse anti-MBP mAb 384. Lane 1, wild-type Aβ column eluate; lane 2, Dutch/Iowa-type Aβ column eluate.

The utility of affinity chromatography in embodiments of the invention is demonstrated in FIG. 10, where homogenates of human brain tissue were passed through affinity columns having different Aβ variants attached by streptavidin to beads in the column. A 20 kDa peptide, presumably MBP, passes through the column loaded with Aβ40WT, but is captured by the Aβ40DI column as shown by the large band eluted from the latter. Mass spectrometric analysis of a tryptic digest of the large eluted band revealed an amino acid spectrum homologous to MBP. Combining this finding with immunoblot analysis provided confirmation that the 20 kDa peptide is MBP and that it is not captured on an Aβ40WT affinity column (FIG. 11).

Figure 12:
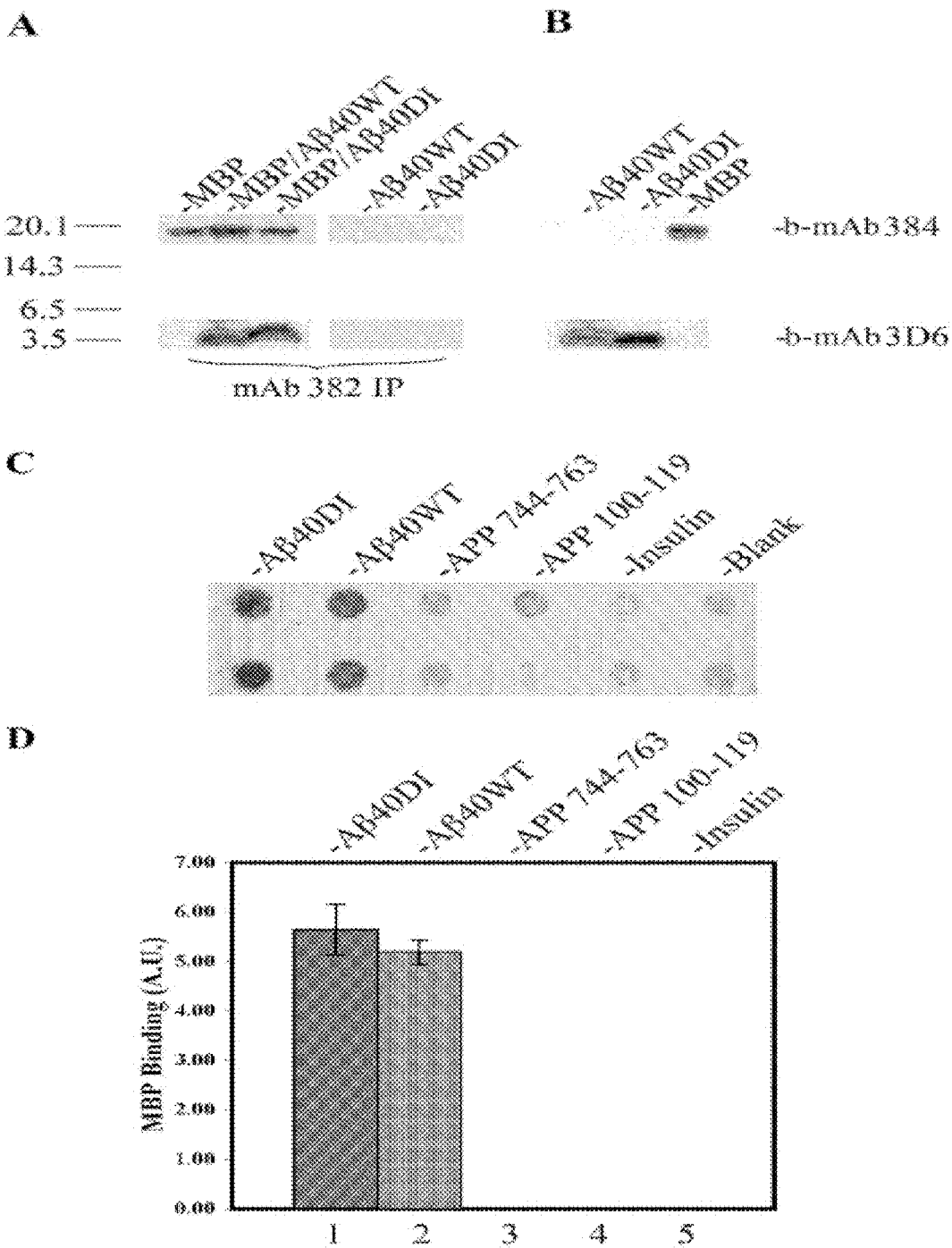
FIG. 12A-D show Interaction of MBP and Aβ peptides. Aβ peptides were immunoprecipitated (IP) with MBP using anti-MBP mAb 382.
Figure 13:
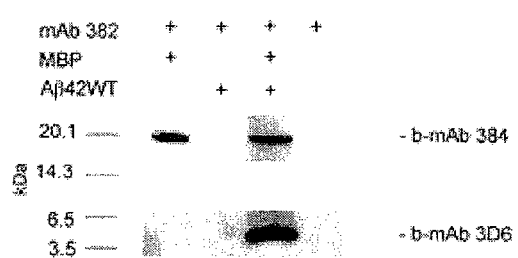
FIG. 13 Co-immunoprecipitation of MBP and Aβ42. Aβ42 peptides were immunoprecipitated with MBP using anti-MBP mAb Immunoprecipitated samples from left to right: MBP alone, Aβ42WT alone, MBP incubated with Aβ42, negative control (no MBP/no Aβ42).

Another benefit of using a combination of methods is illustrated in FIG. 12. Here, the specificity of MEP for different Aβ variants was examined by immunoprecipitation. In this case, MBP bound to Aβ40WT and showed no preference for Aβ40DI. It is to be noted that purified MBP was used. The contrast between these results and those found with affinity chromatography may therefore reflect the intrinsically impure condition of MBP in brain homogenates, wherein substances that modulate binding reactions may be present. MBP also interacts with Aβ42WT in co-immunoprecipitations (FIG. 13). Aβ42WT is more fibrillogenic than Aβ40WT and is strongly implicated in Alzheimer's disease, which provides a basis for embodiments of the present invention directed to the therapeutic use of MBP in this and related diseases.

Figure 14:
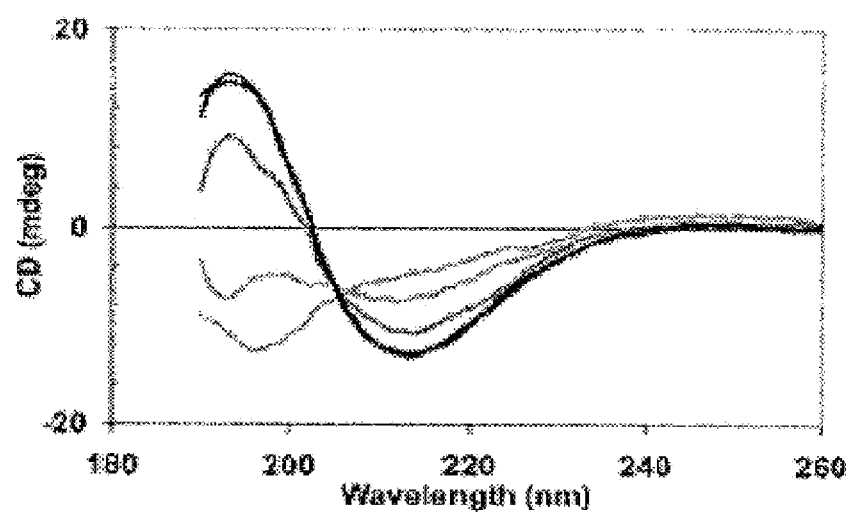
FIG. 14A-C shows Inhibition of Aβ42WT p-sheet formation by MBP, assessed by CD spectroscopy.
Figure 14:
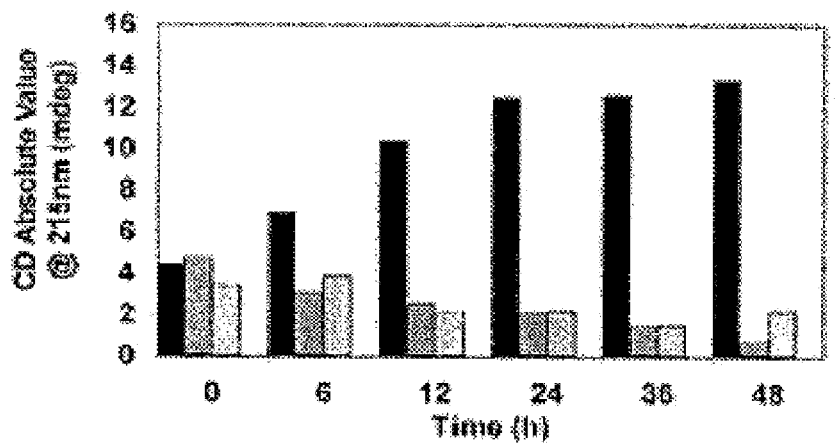
Figure 14:
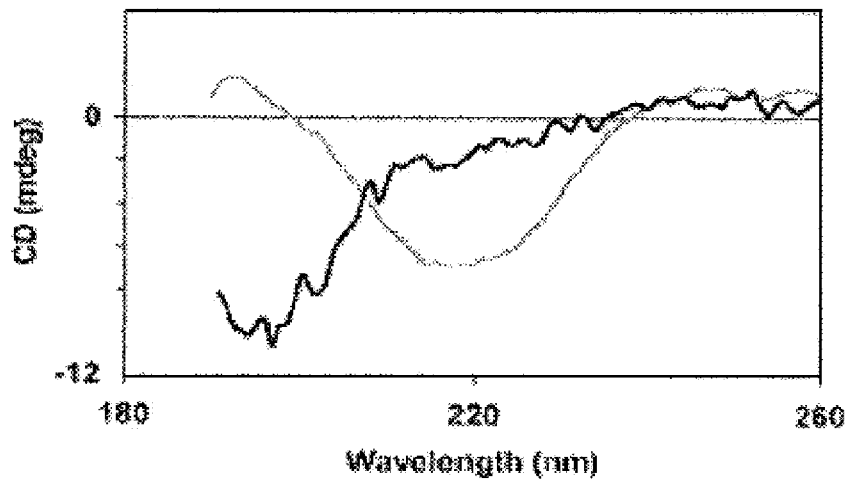

Additional support for using MBP in managing Alzheimer's and related diseases is to be found in results of circular dichroism measurements summarized in FIG. 14. Panel A shows four scans of Aβ42WT incubated for different periods.

Figure 15:
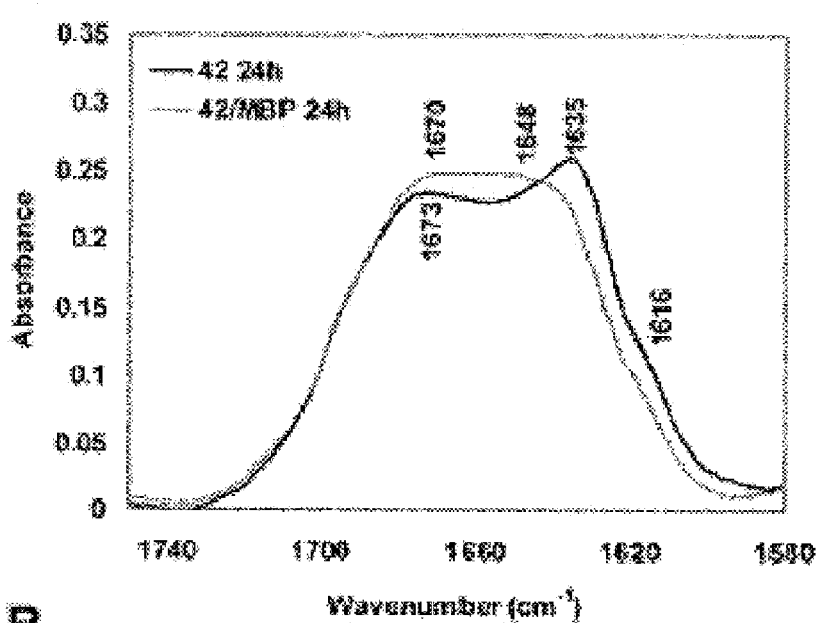
FIGS. 15A&B shows Inhibition of Aβ42 β-sheet formation by MBP, assessed by ATR-IR.
FIG. 15B shows Second-derivative plot of IR spectra in FIG. 15A.
Figure 15:
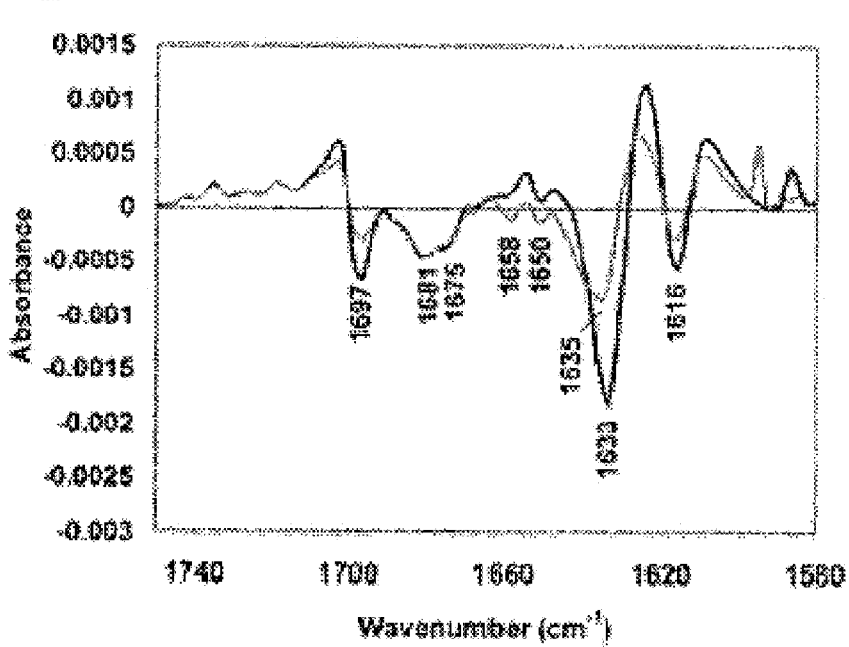

Short incubations correlate with negative ellipticity (see, especially, at about 195 nm), indicative of randomness. Longer incubations show the opposite, indicative of formed fibrils. Adding MBP to the incubates prevents fibril formation (Panel B and black scan in Panel C). When MBP is added late in the course of incubation (Panel C, gray scan), the scan reflects a degree of randomness, largely overshadowed by the presence of formed fibrils. The evanescent wave data (FIG. 15), although less clear, confirm the CD data. One must compare peaks in a derived plot (Panel B) to see the difference, which is especially prominent at wavenumber 1633. Interestingly, there is no difference between 1675 and 1681, which corresponds to the hairpin loop region of Aβ. Thus, MBP-binding apparently does not disturb this loop.

Figure 16:
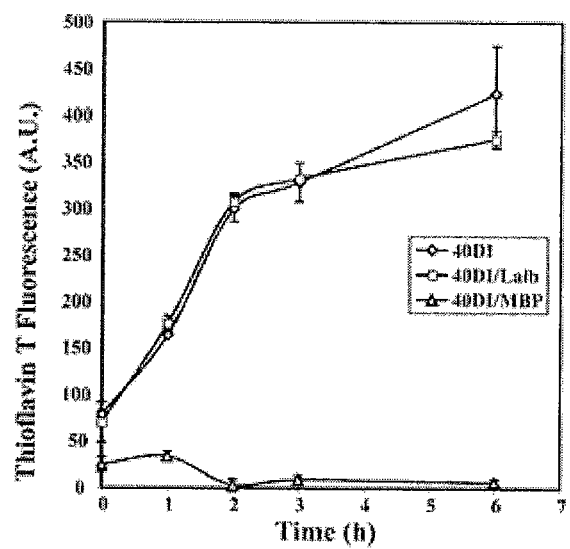
FIG. 16 Thioflavin T analysis of inhibition of CAA mutant Aβ fibril formation by MBP. Aβ40DI at a concentration of 12.5 μM in PBS in the absence (□) or presence of 1.56 μM MBP(□) or bovine a-lactalbumin (Lalb; □) as a control. At specific time points, aliquots were collected from each sample and analyzed by thioflavin T binding and fluorescence to determine fibrillar assembly. Data represent the means±S.D. of triplicate samples. A.U., arbitrary units.
Figure 18:
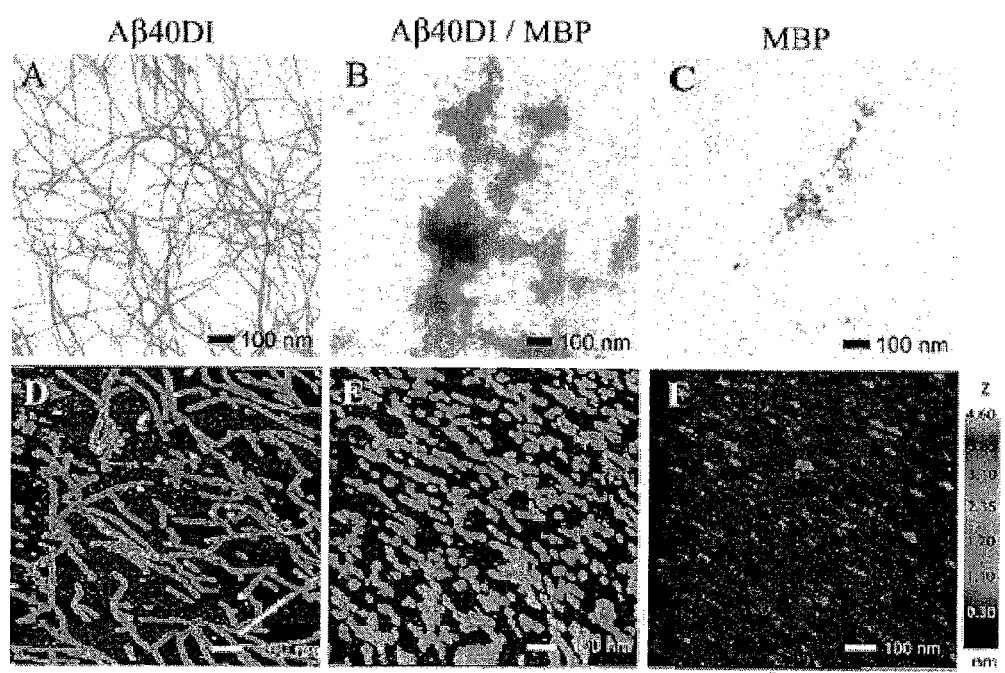
FIG. 18 Inhibition of Aβ40DI fibril formation by MBP as assessed by TEM and single-touch AFM analyses. Aβ40DI peptides at a concentration of 12.5 µM in PBS in the absence or presence of 1.56 µM MBP. Samples were imaged at 6 h by TEM (A and B) and at 3 h by single-touch AFM (D and E). Aliquots of 1.56 µM MBP alone were imaged by TEM (C) and by AFM (F).
Figure 19:
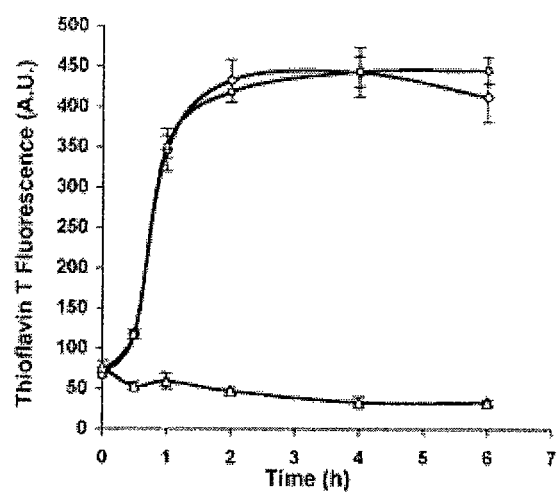
FIG. 19 Thioflavin T analysis for inhibition of Aβ42 fibril formation by MBP. Aβ42 at a concentration of 12.5 µM in PBS in the absence (diamond) or presence of 1.56 µM MBP (triangle) or 1.56 µM □-lactalbumin (square) as control. The data shown are the mean S.D. of triplicate samples.
Figure 20:
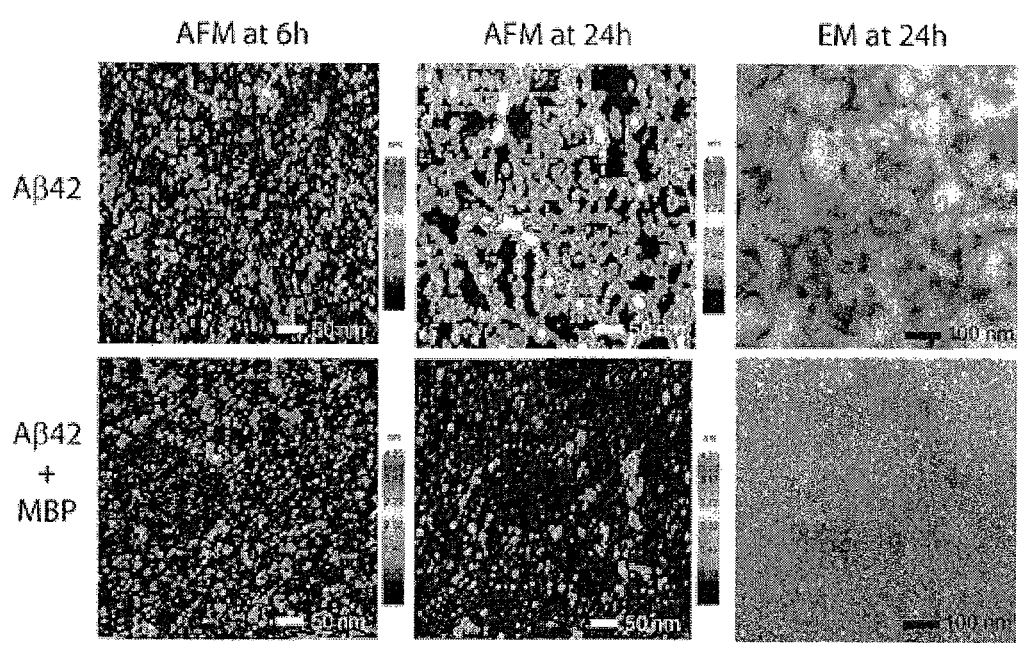
FIG. 20 AFM and TEM images of the inhibition Aβ42WT fibril formation by MBP. Aβ42 samples were incubated at 37° C. in the absence (top row) or presence (bottom row) of MBP at the same ratio of Aβ42:MBP used in the thioflavin T analysis. AFM images were scanned at 6 h and 24 h of incubation. EM images were taken at 24 h of incubation.

It is to be noted that MBP purification does not compromise the binding of MBP to Aβ40DI. Indeed, purified MBP completely inhibits the assembly of Aβ40DI into fibrils as determined by thioflavin T analysis (FIG. 16) and allows no high molecular mass species of Aβ40DI to accumulate as determined by quantitative immunoblot analysis (FIG. 17). This inhibition can be seen in ultrastructural studies as well by comparing, in FIG. 1, panels A, B and C (electron microscopy) and panels D, E, and F (atomic force microscopy). That MBP also prevents fibrillization of Aβ42WT is clearly shown by thioflavin T analysis (FIG. 2) and by atomic force microscopy and electron microscopy (FIG. 20).

Figure 21:
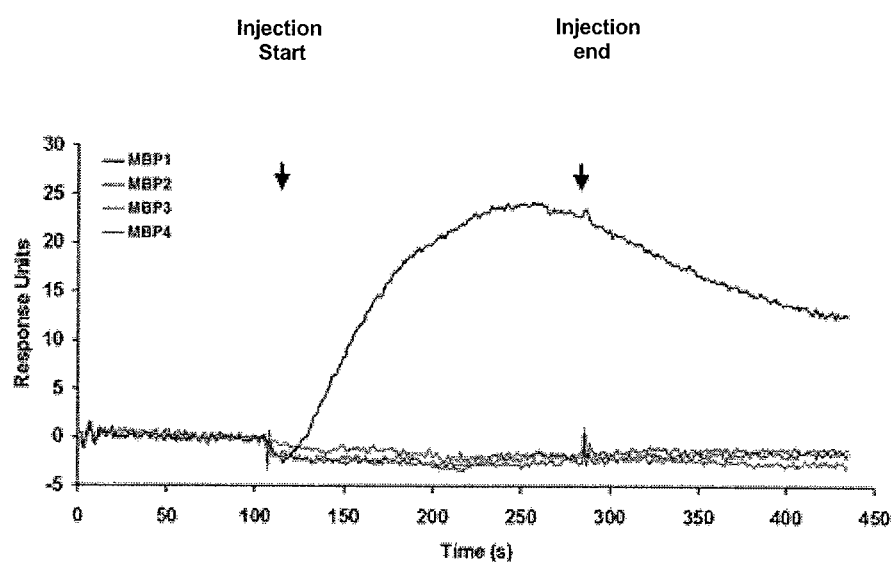
FIG. 21 Binding of MBP peptides measured by SPR analysis. MBP peptides were passed over immobilized Aβ42DI ligands at 50 nM each. Resulting sensorgrams were baseline corrected and plotted as overlays.
Figure 22:
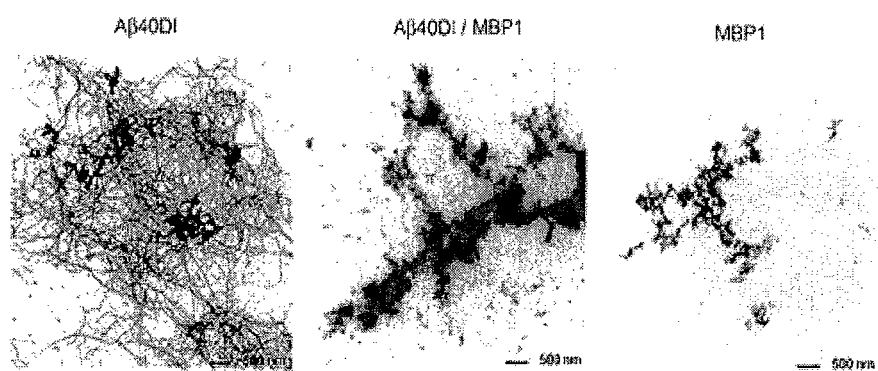
FIG. 22 Inhibition of Aβ40DI fibril formation by MBP as assessed by TEM. Aβ40DI at a concentration of 12.5 µM in PBS in the absence or presence of 1.56 µM MBP1. Samples were imaged at 6 h by TEM.

MBP fragmentation may or may not compromise binding to Aβ40DI. MBP1, constituting the first 64 residues of MBP, binds but MBP2, MBP. 3 and MBP4 (FIG. 21) do not as measured by surface plasmon resonance and confirmed by electron microscopy (FIG. 22). Neither does a C-terminal truncation of MBP1 ("MBP1 ΔCT") lacking residues 50-64, which makes the missing region of considerable interest.

Mutational Analysis of the Aβ40DI Binding Motif in MBP1—

Other known Aβ binding motifs. exist, one of which lies within the APP gene.

Figure 23:
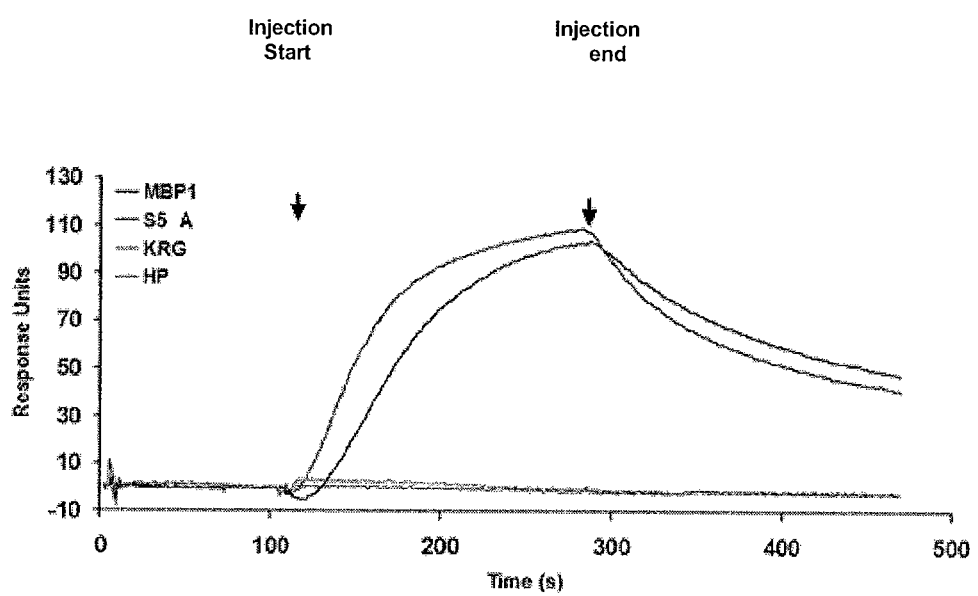
FIG. 23 Binding of MBP1 and MBP1 mutant peptides measured by SPR analysis. MBP1, MBP1 S57A, MBP1 ΔKRG, and MBP1 ΔHP peptides were passed over immobilized Aβ40DI ligands at 100 nM each. Binding is identified by an increase in response during injection (association) followed by a gradual decrease in response following injection (dissociation).
Figure 24:
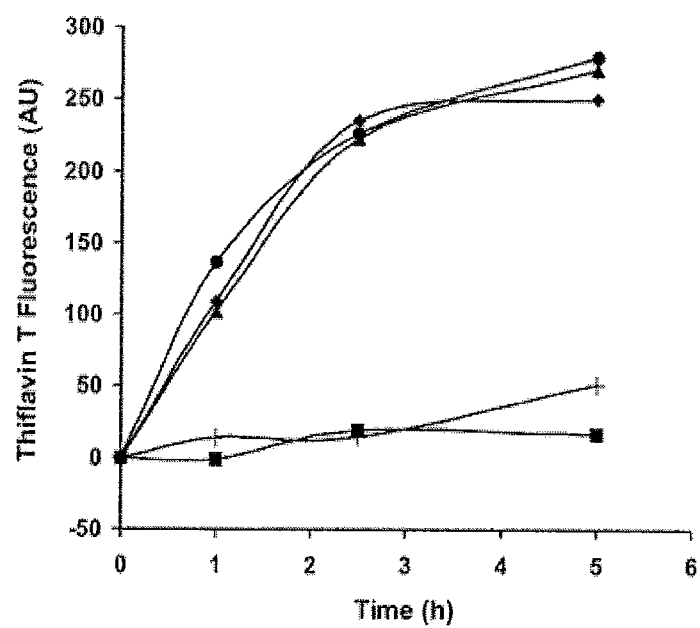
FIG. 24 Thioflavin T analysis for inhibition of Aβ40DI fibril formation by MBP1 mutants. Aβ40DI at a concentration of 12.5 µM in PBS in the absence (diamond) or presence of 1.56 µM MBP1 ΔHP (triangle), 1.56 ΔM MBP1 ΔKRG (circle), 1.56 ΔM MBP1 S57A (plus), or 1.56 µM MBP1 (square).

A comparison of these two sequences demonstrates a homology (KRGxxxxxxHP) (SEQ ID NO: 1) between MBP residues 54-64 and APP residues 99-109. MBP1 mutants modified in this region with alanine substitutions, that is, MBP1 ΔKRG, MBP1 ΔHP), do not bind to Aβ40DI (FIG. 23), but MBP1 with an alanine substitution at Ser57 (MBP1 S57A) does bind. The non-binders were confirmed to also lack fibril inhibition in a thioflavin T assay (FIG. 24).

Determination of Interacting Residues by Nuclear Magnetic Resonance Spectroscopy—

Figure 25:
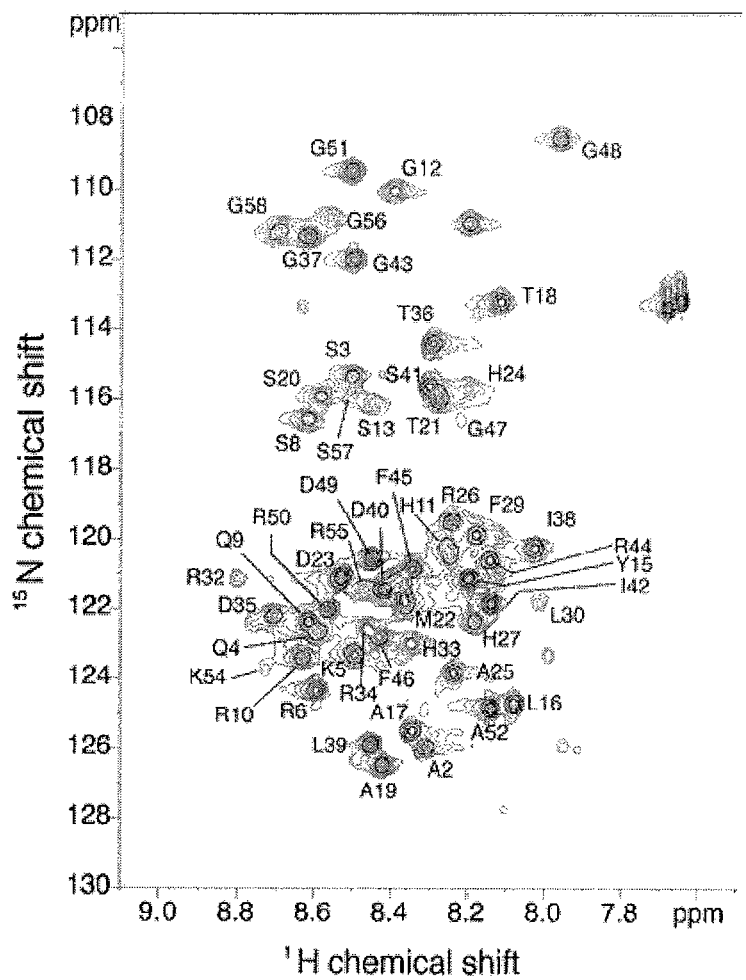
FIG. 25 $^1H$, $^{15}N$ HSQC spectrum of uniformly labeled $^{15}N$, $^{13}C$-MBP1. 0.5 mM $^{15}N$, $^{13}C$-MBP1 was diluted to 0.5 mM in PBS. 52 residues were assigned out of a possible 60 (64 minus 4 prolines).

The foregoing evidence that residues 54-56 and 63-64 are necessary to inhibit Aβ40DI fibrillogenesis does not by itself indicate whether or not these residues interact directly with Aβ or are necessary for the stability of a conformation formed upon Aβ binding. Other distal elements of the binding motif may also be necessary. One means of identifying directly interacting residues is solution NMR spectroscopy, as exemplified below:

Backbone resonance assignments were made using uniformly labeled $^{15}N$, $^{13}C$-MBP1 to obtain CBCACONH and FINCACB spectra. Assignments of 52 backbone peaks out of a possible 60 (64 residues minus 4 prolines) were completed (FIG. 25), with a high degree of probability in most cases. Uniformly labeled $^{15}N$-MBP1 was incubated with and without unlabeled Aβ40DI and its $^1H$-$^{15}N$ HSQC spectra resolved.

Figure 26:
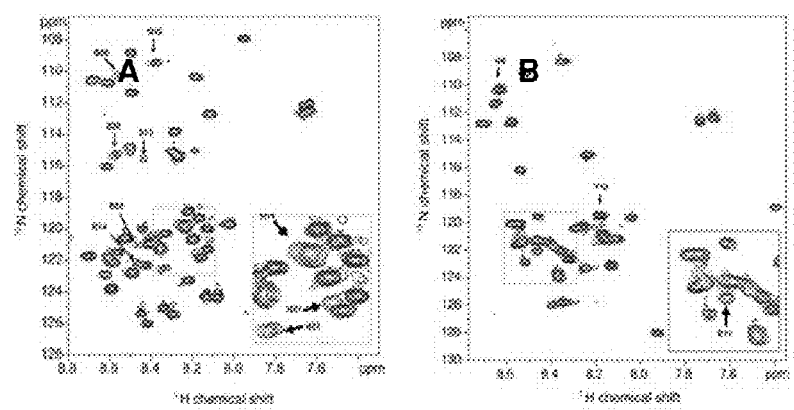
Figure 27:
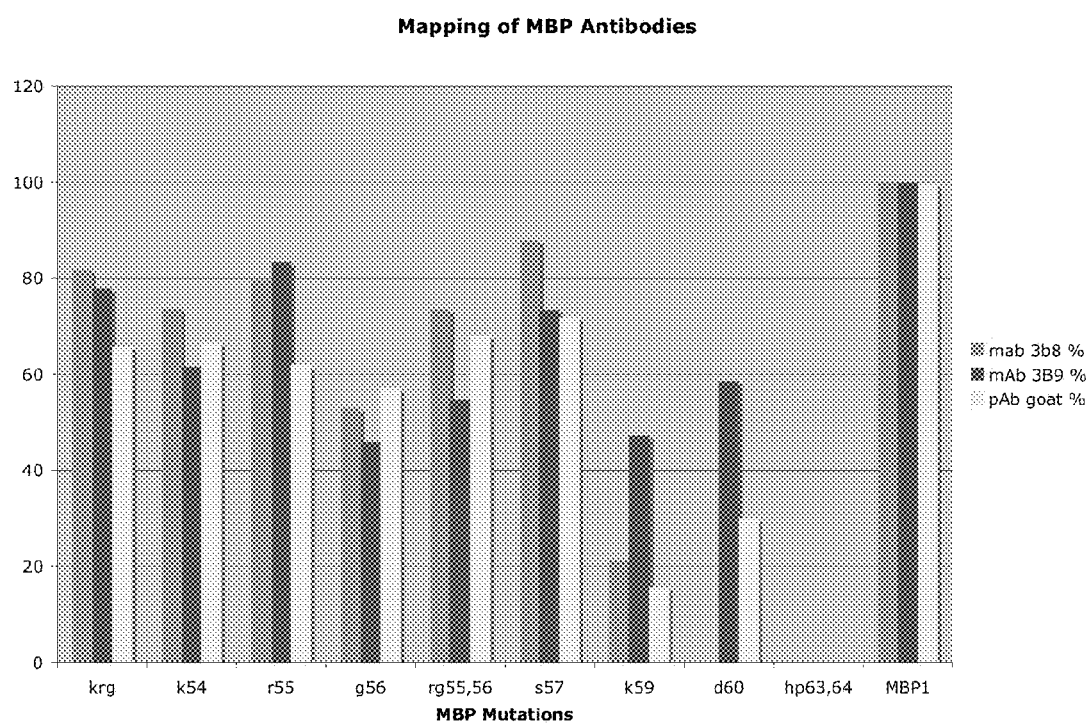
FIG. 27 is a bar graph representation of antibody-binding to a fragment of myelin basic protein (MBP1) and mutants thereof, relative to wild-type MBP1 (SEQ ID NOS: 51 and 52).

Comparisons of $^1H$-$^{15}N$ HSQC spectra with and without Aβ40DI reveal significant cross-peak shifts in several residues (FIG. 26). The identified residues demonstrate that the binding motif for Aβ40DI in MBP1 is composed of several distal elements. These include Arg55 and Gly56, which, as discussed above, were found to be homologous to a sequence in APP near an Aβ binding site and, when subjected to alanine substitution, caused affinity for Aβ40DI to be lost.

One embodiment of the present invention provides a method for identifying substances that either enhance ("activators") or inhibit ("inhibitors") interference with fibrillization by a functional species of MBP or by a fragment thereof, Activators and inhibitors are referred to herein collectively as "modulators." That is, they are "modulatory substances" or, interchangeably, "modulating substances." Persons of skill in the assay arts may use the methods referred to above to identify and evaluate the potency of such modulators. A modulation by a given substance may become manifest under conditions where a fibrillizing peptide is contacted with a species of MBP or a fragment thereof in vitro, in situ, or in vivo. A modulator may, for example, bind to the fibrillizing peptide, or to a product of fibrillization, or may otherwise change the MBP or a fragment thereof structurally or functionally. Without intending to be limited by any example specified herein, a modulator may act by up-regulating (or down-regulating) biosynthesis of native MBP or of an MBP introduced as a transgene. The modulator may also act as a proteolytic co-factor. The modulator may promote fragmentation of an MBP in such a manner that an interfering fragment of MBP accumulates. The modulator may potentiate the action of an endogenous or exogenous interfering fragment.

In other embodiments, the invention provides methods for treating subjects having a disease or disorder that is susceptible to treatment by interfering with fibrillization either before or after a fibrillizing peptide has aggregated to form fibrils, including matrix-like structures that incorporate other molecular species (e.g., calcium salts) or formed elements (e.g., blood platelets) to form complex biological structures. In some embodiments, an interfering MBP fragment, with or without modulators, is administered, directly or indirectly, by various modes and routes of administration, preferably near sites where a fibrillizing peptide tends to be expressed or to accumulate. In these embodiments, it is thought, the fragment tends to interfere with aggregation. In some embodiments, a functional species of MBP (that is, wild-type MBP or an isoform or variant that is active in the embodiments of the instant invention) is administered to digest fibril precursors before they aggregate or to disrupt formed aggregates.

A "subject," used herein interchangeably with the term "patient," may be a human or any other mammal including, without limitation, a primate, rat, mouse, rabbit, pig, cow, sheep, goat, cat or dog. A "subject at risk" for a disease, as the term is used herein, is any subject having a condition which, in the judgment of a practitioner of the healing arts, is predictive of the disease. It is not necessary that the subject present any objectively or subjectively recognizable symptom of the disease to be "at risk."

Fibrillizing peptides include, but are not limited to, any fibrillizing form of immunoglobulin light chain, immunoglobulin heavy chain, transthyretrin, betazmicroglobulin, fibrinogen alpha chain, apolipoprotein AI, apolipoprotein AII, lysozyme, amyloid beta protein precursor, prion protein, cystatin C, amyloid Bri precursor protein, amyloid Dan precursor protein, gelsolin, lactoferrin, keratoepithelin, calcitonin, amylin, atrial natriuretic factor, prolactin, keratin and media.

The invention provides a convenient means for identifying any fibrillizing peptide that is a substrate for a functional species of MBP or a binding partner for an MBP fragment. As used herein, the term "functional species of MBP" encompasses a polypeptide sequence encoded by any of the nucleic acids having nucleotide sequences as listed in Tables 4-7 herein, and any functional variant thereof. Any protein or polypeptide having an amino acid sequence encoded by any part of such a nucleic acid is an "MBP fragment." The full-length protein sequence, or a variant thereof, can be isolated or purified from a cell that naturally expresses it by many techniques well-known in the art. Alternatively, the protein, and fragments thereof, can be produced by recombinant, chemical, or protein synthesis methods, all of which are also routinely practiced by skilled artisans.

The term "polypeptide activity" refers herein to any activity of an MBP manifested by the disruption of biological structures comprising proteinaceous elements, whether monomeric, aggregated or polymerized. Thus, although MBP may hydrolyze or proteolyze such elements under some conditions, it is not intended that the term "polypeptide activity" be synonymous with proteolysis. Thus, evident disruption by a functional MBP species or a plaque that comprises Aβ, with or without evidence of proteolysis, is a "polypeptide activity" of that species. A fragment of MBP also has "polypeptide activity" herein, with or without evidence of its binding to a fibrillizing peptide. The fragment has "polypeptide activity" if it interferes in any way with fibrillization.

The term "therapy," used interchangeably herein with "treatment" and variants (e.g., "treating"), refers to an attempt to prevent or ameliorate a disease ("abnormal condition," "disorder," "syndrome," etc.), or the symptoms thereof, in a patient or a subject. It is not intended that "treating" a disease require curing or eradicating it. It is only necessary that the treatment have a therapeutic effect. "Prevention" of a disease or disorder includes the prevention of the recurrence, spread or onset of the disease or disorder. It is not intended that the present invention be limited to complete prevention. For example, delayed onset constitutes prevention herein, as does a reduction in the severity of the disease or disorder. Similarly, the progression of a disease is considered herein to be "reduced" or "inhibited" if, in the judgment of a practitioner of the healing arts, one or more of the characteristic indicia of progression of the disease are reduced or inhibited.

The term "therapeutic effect" refers to the inhibition, activation or replacement of factors causing or contributing to an abnormal, pathological or pathogenic condition. A therapeutic effect may or may not relieve symptoms of the abnormal condition. A prophylactic or preventative effect delays the onset or reduces the severity of one or more of the symptoms or factors causing or contributing to the abnormal condition. In reference to the treatment of abnormal conditions, a "therapeutic effect" can refer, without limitation, to one or more of the following: (a) an increase or decrease in the proliferation, growth, and/or differentiation of cells or the products of cells, whether those products accumulate within the cells or are released therefrom; (b) inhibition (i.e., slowing or stopping) of cell death; (c) potentiation or stimulation of cell death, especially programmed, or apoptotic cell death (d) inhibition of structural or functional degeneration of a cell, tissue, organ or organ system; (e) relieving to some extent one or more of the symptoms associated with the abnormal condition; and (f) enhancing or depressing the function of an affected cell or population of cells. Criteria for treating to the level of therapeutic effect, i.e., to prevent a disease and to evaluate any slowing in the disease's progression, are determined according to the judgment of a person of skill in the healing arts.

An "abnormal condition" refers herein to a function in the cells or tissues of an organism that deviates from the normal function in that organism. An abnormal condition, by way of non-limiting examples, can relate to cell proliferation, cell differentiation, cell survival or cell products. Abnormal cell proliferative conditions include, for example, cancers such as fibrotic and mesangial disorders, abnormal angiogenesis and vasculogenesis, wound healing, psoriasis, diabetes mellitus, and inflammation. Abnormal cell products include metabolic products, hormones and other secreted products, cell signaling agents (whether intracellular or extracellular), elements of intracellular architecture including the cell membrane, "housekeeping" enzymes, and elements of the extracellular matrix.

Abnormal differentiation conditions include, but are not limited to neuro degenerative disorders, slow wound healing rates, and slow integration of tissue grafts. Abnormal cell survival conditions relate to, for example and without limitation, conditions in which programmed cell death (apoptosis) pathways are activated or abrogated. Toxic agents of various types, both endogenous and exogenous, can induce any of the these conditions.

The abnormal condition can be prevented or treated with an identified compound or substance of the invention by contacting the compound or substance to the cells or tissues of the organism either within the organism or outside of the organism. Cells existing outside the organism can be maintained or grown in cell culture dishes, for example. For cells harbored within the organism, many techniques exist in the art to administer substances, including (but not limited to) oral, parenteral, and dermal injection, and aerosol applications. Injections, without limitation, may be made into the bloodstream, into cerebrospinal fluid, epidurally or subdurally, or by instillation into the eye, body cavities, and wound sites. For cells outside of the organism, multiple techniques exist in the art to administer the substances, including (but not limited to) cell microinjection techniques, transformation techniques, and carrier techniques.

In a preferred embodiment of the present invention, an abnormal condition can be prevented or treated by using an MBP or a fragment thereof linked to a therapeutic agent to deliver the agent to a target, the target being defined as a target site for the MBP or a binding site for the MBP fragment. The "therapeutic agent" may be any agent that confers any therapeutic effect on a subject. As a non-limiting example, a fragment of MBP may be employed to deliver to sites of accumulation in the brain of a subject, a drug such as tetrahydroaminoacridine conjugated to the fragment. Alternatively, and again without limitation, a cell, a viral particle, a macromolecule or a non-biological particle may be conjugated with the fragment. In preferred embodiments, the therapeutic agent is a "modulating substance" as defined herein. Many linkers and methods for their use in linking small molecules to peptides are known in the art and are readily practiced by persons of skill in the art. Inasmuch as Aβ is available in quantity only in diseased states (specifically, Alzheimer's disease, Lewy body dementia and cerebral amyloid angiopathy), it is an apt target for a therapeutic agent. An MBP fragment comprising a conjugate with a therapeutic agent is referred to herein as a "targeting moiety."

In another embodiment of the invention, a conjugate comprising MBP or a fragment of MBP and a "marking agent" is provided. As used herein, a "marking agent" is any substance that serves to locate a site at which an administered MBP localizes or a site where an administered MBP fragment is bound to a fibrillizing peptide. Nonlimiting examples include a fluorescent molecule, a radioisotope, a contrast agent, and an antigen to a specific antibody. It is not intended that the means of detecting the marking agent be limited in any way. Light or electron microscopy may be employed, as may chemical methods, or various imaging modalities.

Another preferred embodiment of the present invention offers an alternative to antibodies to provide a peripheral "sink" for sequestering Aβ that emerges from the central nervous system into the circulation of affected patients. Appropriate dosages of functional fragments of MBP for peripheral injection are readily calculable by persons of skill in the art from binding data for the MBP fragment and binding data from antibody preparations known in the art. See, for example U.S. Pat. No. 7,195,761 to Holtzman et al., incorporated herein in it entirety by reference for all purposes. As used herein, the term "peripheral" is used simply to distinguish over injections into the central nervous system, the brain in particular.

MBP or fragments thereof may be administered in relevant embodiments of the invention by a variety of routes, including but not limited to topical, oral, nasal, enteral, intravenous, intraarterial, intramuscular, intracardiac, subcutaneous, intradermal, intrathecal, epidural, intracranial, cerebro-ventricular, brain parenchymal, intraperitoneal, intravesical, inhalational, and intraocular. Of particular relevance in certain embodiments of the invention are methods wherein stem cells are stably transfected ex vivo with a nucleic acid sequence that encodes an MBP or a fragment thereof and transplanted to or near a site where a fibrillizing peptide is expressed or tends to accumulate in a subject.

A "variant" polypeptide of the invention can differ in amino acid sequence from a polypeptide encoded in a nucleic acid having the nucleotide sequence of any shown in Tables 4-7 by one or more substitutions, deletions, insertions, inversions, and truncations or a combination of any of these. "Isoforms," as used herein, encompass variants that arise from alternative splicing of a single gene or from different genes that differ, generally, by single nucleotide polymorphism. Any polypeptide can be made to contain amino acid substitutions that substitute a given amino acid with another amino acid of similar characteristics. See Bowie et al., Science 247: 1306-1310, 1990. A "variant" may be functional or non-functional.

Modified functional species of MBP and fragments thereof are useful in the present invention so long as the modification does not destroy the molecule's polypeptide activity (except that inactive modifications may be useful as controls). Amino acids that are not critical for function can be identified by methods known in the art, such as site-directed mutagenesis, crystallization, nuclear magnetic resonance, photoaffinity labeling or alanine-scanning mutagenesis (Cunningham et al., Science 244:1081-1085 (1989); Smith et al., J. Mol. Biol. 224:899-904 (1992); de Vos et al., Science 255:306-312 (1992)). Modified proteins can be tested for biological activity by detecting binding to a substrate (i.e., a fibrillizing peptide), interference with fibrillization, etc., with in vitro or in vivo assays. Typical modifications are described in detail in the art. See, for example, U.S. Pat. No. 6,331,427 to Robison.

A polypeptide having the full-length sequence of MBP or a variant, or an amino acid sequence encoded by a nucleic acid having a nucleotide sequence as shown in Tables 4-7, or a functional variant or fragment thereof, joined to another polypeptide with which it is not normally associated may also find use in the invention. An example would be a peptide having an amino acid sequence of MBP or a functional part thereof operatively linked, at either its N-terminus or C-terminus, or in a side chain, to a heterologous protein having an amino acid sequence not substantially homologous to MBP (or to the relevant fragment thereof).

A fusion protein may or may not affect the activity of a functional species of MBP or an interfering fragment of MBP. Fusion proteins include, but are not limited to, enzymatic fusion proteins, for example betagalactosidase fusions, yeast two-hybrid GAL fusions, poly-His fusions and Ig fusions. Such fusion proteins, particularly poly-His fusions, can facilitate the purification of polypeptides of the invention. In certain host cells, expression and/or secretion of a protein can be increased by using a heterologous signal sequence fused to the polypeptides of the invention that transports the polypeptide to an extracellular matrix or localizes the polypeptide in the cell membrane.

Other fusion proteins may affect the activity of an MBP or a fragment thereof. For example, without limitation, a binding domain (or parts thereof) of an MBP fragment fragment may be replaced by a domain from another peptide with a different binding specificity or affinity. Accordingly, chimeric peptides can be produced from an MBP fragment, which have altered binding or other polypeptide activity characteristics. Also, a protease domain (or parts thereof) in an MBP may be replaced by a domain from another peptide or other type of protease. Similarly, a substrate-binding domain, or subregion thereof, may be replaced with the corresponding domain or subregion from another peptide with different substrate specificity. Accordingly, chimeric peptides may be produced from a functional species of MBP such that, for example, release of substrate is faster or slower than that of the unmodified polypeptide. Likewise, the affinity for substrate may be altered, or proteolysis or other action on the substrate prevented. MBP fragments having no polypeptide activity and non-functional variants of MBP may be engineered to contain one or more amino acid substitutions, deletions, insertions, inversions, or truncations in a critical residue or critical region. Modifications of MBP or fragments can be made to affect, the function, for example, of one or more of the regions corresponding to substrate binding, subcellular localization (such as membrane association), proteolytic cleavage or effector binding.

Biologically active fragments of MBP can comprise a domain or region identified by analysis of the polypeptide sequence by well-known methods. Such biologically active fragments include, but are not limited to domains comprising one or more binding sites, glycosylation sites, cAMP and cGMP-dependent phosphorylation sites, N-myristoylation sites, activator binding sites, casein kinase 11 phosphorylation sites, palmitoylation sites, amidation sites. Such domains or sites can be identified by means of routine procedures for computerized homology or motif analysis.

Embodiments of the invention encompass not only variants of MBP having amino acid sequences as encoded by any of the nucleic acids in, and MBP fragments having polypeptide sequences encoded in nucleic acids having a nucleotide sequence as described in Tables 4-7 ("wild-type fragments"). Also encompassed are derivatives or analogs thereof in which (i) an amino acid is substituted with an amino acid residue that is not one encoded by the genetic code, (ii) the wild-type polypeptide is fused with another compound, such as a compound to increase the half-life of the polypeptide (for example, polyethylene glycol), or (iii) additional amino acids are fused to the polypeptide, such as a leader or secretory sequence or a sequence for purification of the polypeptide or a pro-protein sequence. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Particularly common modifications include glycosylation, lipid attachment, sulfation, gamma-carboxylation of glutamic acid residues, hydroxylation and ADP-ribosylation. See PROTEINS—STRUCTURE AND MOLECULAR PROPERTIES, 2nd Ed., T. E. Creighton, W. H. Freeman and Company, New York (1993); Wold, F., POST TRANSLATIONAL COVALENT MODIFICATION OF PROTEINS. B. C. Johnson, Ed., Academic Press, New York 1-12 (1983); Seifter et al. (Meth. Enzymol. 182: 626-646 (1990)) and Rattan et al. (Ann. N.Y. Acad. Sci. 663:48-62 (1992)).

Modifications can be made anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides.

Polypeptides of MBP or variants or fragments thereof may be modified by the process in which they are synthesized. With recombinantly-produced polypeptides, for example, the modifications will be determined by the host cell post-translational modification capacity and the modification signals in the polypeptide amino acid sequence. Accordingly, when glycosylation is desired, a polypeptide should be expressed in a glycosylating host, generally a eukaryotic cell. The same type of modification may be present in the same or varying degree at several sites in a given polypeptide. Also, a given polypeptide may contain more than one type of modification.

A functional species of MBP or a fragment thereof known to have polypeptide activity can be used to identify compounds or substances that modulate its interfering effect on fibrillization. Such substances may increase or decrease affinity or rate of binding to a substrate or activator, compete with substrate or activator for binding, or displace substrate or activator bound to the MBP or the fragment. For instance, a modulating substance may be a mutated polypeptide or a functional variant thereof, or an appropriate fragment containing a mutation(s) that compete(s) for substrate, activator or other protein that interacts with the polypeptide. Accordingly, a fragment that competes for substrate or activator, for example with a higher affinity, may serve as an element in embodiments of the invention. It is not intended that a "modulating substance" be limited to a substance that exerts its modulatory effect only by contacting both the fibrillizing peptide and the MBP or MBP fragment. It is not intended, either, that if the substance does contact both elements, that such contact must be simultaneous. In some embodiments, the candidate substance (i.e., a substance whose activity is to be proven by means of the assay) contacts the fibrillizing peptide before the substance contacts the MBP or MBP fragment. In other embodiments, the substance contacts the fibrillizing peptide after the substance contacts the MBP or MBP fragment. In some embodiments, the substance contacts the fibrillizing peptide and not the MBP or the MBP fragment. In some embodiments, the substance contacts the MBP or the MBP fragment and not the fibrillizing peptide.

As used herein, the terms "bind," "binding, bound" etc. refer to a phenomenon in which two or more molecules, at a given temperature, pressure and concentration, interact with one another to the extent that they are stably associated with one another (i.e., where the association is greater than that which occurs in the "random walk" of Brownian movement).

A "fibrillizing interaction" is a process in which such binding leads to polymerization.

In some embodiments, the invention affords the ability of determining whether a species of MBP or a fragment of MBP can bind to a substrate, inhibitor or other molecule. This can also be determined by real-time Bimolecular Interaction Analysis (BIA). Sjolander, S, and Urbaniczky, C. (1991) Anal. Chem., 63:2338-2345 and Szabo et al. (1995) Curr. Opin. Struct. Biol., 5:699-705. "BIA" is a technology for studying biospecific interactions in real time, without labeling any of the interactants. Changes in the optical phenomenon surface plasmon resonance (SPR) can be used as an indication of real-time reactions between biological molecules. Similarly, a microphysiometer can be used to detect the interaction of a test compound with the polypeptide without the labeling of either the test compound or the polypeptide. McConnell, H. M. et al. 1992) Science, 257:1906-1912.

MBP and fragments of MBP can also be used in a two-hybrid assay or three-hybrid assay (see, e.g., U.S. Pat. No. 5,283,317; Zervos et al. (1993) Cell, 72:223-232; Madura et al. (1993) J. Biol. Chem., 268:12046-12054; Bartel et al. (1993) Biotechniques, 14:920-924; Iwabuchi et al. (1993) Oncogene, 8:1693-1696; and Brent WO94/10300), to identify other proteins which bind to or interact with the protein and modulate its activity.

Binding can be determined by binding assays well known to the skilled artisan, including, but not limited to, gel-shift assays, Western blots, radiolabeled competition assay, phage-based expression cloning, co-fractionation by chromatography, co-precipitation, cross linking, interaction trap/two-hybrid analysis, southwestern analysis, ELISA, and the like, as described in, for example, Current Protocols in Molecular Biology, 1999, John Wiley & Sons, NY, incorporated herein by reference in its entirety. The substances to be screened include, but are not limited to, substances of extracellular, intracellular, biological or chemical origin.

A number of naturally occurring Aβ chaperone-binding molecules that modulate fibrillar assembly of the peptide have been identified. For example, apoE has been described to either promote or inhibit Aβ fibril formation in vitro (Strittmatter et al., (1993) PNAS 90:8098-8102; LaDu et al., (1994) J Biol Chem 269:23403-23404; Pillot et al., (1999) J Neurochem 72:230-237; Sanan et al., (1994) J Clin Invest 94: 860-869; Aleshkov et al., (1997) Biochemistry 36: 10571-10580). ApoJ, otherwise known as clusterin, is another chaperone that facilitates Aβ fibril formation in vitro and in vivo (Ghiso et al., (1993) Biochem J 293 (Pt. 1):27-30; Matsubara et al., (1995) J Biol Chem 270:7563-7567; DeMatos et al., (2002) PNAS 99:10843-10848). Other reported Aβ chaperones that may influence Aβ fibril assembly include $\alpha_1$-antichymotrypsin (Mucke et al., (2000) Am J Pathol 157:2003-2010; Potter et al., (2001) Neurobiol Aging 22:923-930), transthyretin (Tsuzuki et al., (2000) Neurosci Lett 281:171-174; Schwarzman et al., (2004) Amyloid 11:1-9), proteoglycans Yang et al., (2001) Amyloid 8 Suppl 1:10-19; Cotman et al., (2000) Mol Cell Neurosci 15:183-198, and gangliosides (Choo-Smith et al., (1997) J Biol Chem 272:22987-22990; Kakio et al., (2001) J Biol Chem 276:24985-24990). In these reports, the study of the interaction of chaperones was restricted to wild-type Aβ peptides. The involvement of these Aβ chaperones in promoting or inhibiting CAA mutant Aβ fibril formation remains largely unknown.

Substances to be tested for modulatory activity according to the present invention can be obtained, for example, without limitation, from biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Lam, K. S., Anticancer Drug Des. 12:145, 1997. Examples of methods for the synthesis of molecular libraries can be found in the art, for example in DeWitt et al. Proc. Natl. Acad. Sci. U.S.A., 90:6909, 1993; Erb et al. Proc. Natl. Acad. Sci. U.S.A., 91:11422, 1994; Zuckermam et al. J. Med. Chem., 37:2678 1994; Cho et al. Science, 261:1303, 1993; Carell et al., Angew. Chem. Int. Ed. Engl., 33:2059, 1994; Carell et al. Angew. Chem. Int. Ed. Engl., 33:2061, 1994; and Gallop et al. J. Med. Chem., 37:1233, 1994.

The invention does not restrict the sources for suitable test substances, which may be obtained from natural sources such as plant, animal or mineral extracts, or non-natural sources such as small molecule libraries, including the products of combinatorial chemical approaches to library construction, and peptide libraries.

Libraries of compounds may be presented in solution (e.g., Houghten, Biotechniques, 13:412 421, 1992), or on beads (Lam, Nature, 354:82-84, 1991), chips (Fodor, Nature, 364:555-556, (1993), bacteria (Ladner, U.S. Pat. No. 5,223,409), spores (Ladner, U.S. Pat. No. '409), plasmids (Cull et al., Proc. Natl. Acad. Sci. U.S.A., 89:1865-1869, 1992) or on phage (Scott and Smith, Science, 249:386-390, 1990; Devlin Science, 249:404-406, 1990; Cwirla et al., Proc. Natl. Acad. Sci., 97:6378-6382, 1990; Felici, J. Mol. Biol., 222:301-310, 1991; Ladner supra) or a library of mammalian cells. Test substances include, for example, peptides such as soluble peptides, including Ig-tailed fusion peptides and members of random peptide libraries (see, e.g., Lam et al., Nature 354: 82-84, 1991; Houghten et al., Nature 354:84-86, 1991) and combinatorial chemistry-derived molecular libraries made of D- and/or L-configuration amino acids; phosphopeptides (e.g., members of random and partially degenerate, directed phosphopeptide libraries, see, e.g., Songyang et al., Cell 72:767-778, 1993); antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and small organic and inorganic molecules such as those obtained from combinatorial and natural product libraries. Preferably, these inhibitors will have molecular weights from 100 to 200 daltons, from 200 to 300 daltons, from 300 to 400 daltons, from 400 to 600 daltons, from 600 to 1000 daltons, from 1000 to 2000 daltons, from 2000 to 4000 daltons, from 4000 to 8000 daltons and from 8000 to 16,000 daltons.

Alternatively, or in conjunction with a modulatory substance, a functional species of MBP or an interfering fragment of thereof may be therapeutically administered to a subject in need of such treatment in a pharmaceutical composition in a pharmaceutically acceptable vehicle.

A substance identified according to an assay described herein, or a functional species of MBP or fragment thereof, may be administered to an individual to compensate for reduced or aberrant expression activity in vivo. The administered MBP or fragment may compensate for reduced or aberrant expression of MBP itself or an endogenously produced fragment thereof.

The modulating substance(s) and/or the MBP or MBP fragment can be administered to a human patient directly, or in the form of a pharmaceutical composition, admixed with other active ingredients, as in combination therapy, or suitable carriers or excipient(s). Techniques for formulation and administration of the substances of the instant application may be found in REMINGTON'S PHARMACEUTICAL SCIENCES, Mack Publishing Co., Easton, Pa., latest edition. All methods are well-known in the art.

In a preferred embodiment of the present invention, a modulating substance is administered as a conjugate with MBP or a fragment of MBP. In some embodiments, the fragment targets a fibrillizing peptide and delivers the modulating substance in a targeted manner to sites where the fibrillizing peptide tends to accumulate. Numerous methods of conjugating modulating substances to a peptide are well known to skilled practitioners. Many drug-peptide conjugates are available from commercial sources. As used herein, the term "drug-peptide" conjugate is not intended to limit the ways in which a drug (or "modulating substance") may be associated with an MBP or an MBP fragment. Any chemical linking means (carbodiimide or maleimide reactions, for example) or attachment to liposomes, nanoparticles, etc. that retains the intended activity of the substance represent "conjugation" (or "linkage") herein.

Many of the modulating substances of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Pharmaceutical compositions suitable for use in the present invention include compositions where the active ingredient, i.e., a substance identified from a screening assay described herein, a functional species of MBP, or an interfering fragment of MBP, is contained in an amount effective to achieve its intended purpose. More specifically, a therapeutically effective amount of a substance or of the MBP or the interfering fragment means an amount effective to prevent, alleviate or ameliorate symptoms of disease or prolong the survival of the subject being treated. Determination of a therapeutically effective amount is well within the capability of those skilled in the art, especially in light of the detailed disclosure provided herein.

Polynucleotides encoding a functional species of MBP or an interfering fragment of MBP may be used in developing treatments wherein such a polynucleotide is introduced into one or more cells of a subject in such a manner that the introduced polynucleotide expresses the MBP's amino acid sequence, or a functional variant thereof, or a fragment thereof, in vivo. Such treatments may be for the purpose of replacing a defective or absent gene comprising the nucleotide or for the pharmaceutical purpose of providing an endogenous source of the MBP or the fragment. The latter purpose may be realized by introducing the polynucleotide where the endogenous source of the fragment is the full-length polynucleotide.

Any of a number of vectors known in the art are suitable for delivering a nucleic acid to a cell in vivo. Suitable vectors may simply be naked nucleic acid, or nucleic acid encapsulated in liposomes, dendrimers, or a variety of other particles that carry nucleic acid within or on their surfaces. Naked nucleic acid, e.g. in the form of a plasmid, a cosmid or a DNA molecule not encapsidated by a virus, is particularly suitable for transfection of cells. More complicated but also suitable as vectors for delivering nucleic acids to the brain or other tissues to effect transfection are viral vectors. Viruses have the advantage that foreign or heterologous genes or coding sequences may be inserted into the viral genome. After infection of a cell by the virus, the foreign nucleic acid is delivered to the nucleus of the cell. There are at least five classes of clinically available viral vectors, derived from (onco)retrovirus, lentivirus, adenovirus, adeno-associated virus and herpes virus. Those viral vectors whose genomes are integratable into the host cell DNA (oncoretroviruses and lentiviruses) may be preferred where stable genetic alteration in dividing cells is required. The other viruses mentioned persist in the cell nucleus as extrachromosomal episomes but are capable of mediating persistent transgene expression in non-proliferating cells. The most appropriate vector will depend on the particular gene therapy being attempted. Generally, recombinant viruses are preferred and, even more preferably, the recombinant virus is replicant-deficient.

For convenience, the term "gene" is used herein to describe regions of nucleic acid not only that are transcribed into mRNA and translated into polypeptides (structural genes), but also those that are transcribed into RNA (e.g. rRNA, tRNA) and those that function as regulators of the expression of the former two types. Preferably the nucleic acid delivered to a cell-type of interest will encode a structural gene relevant (directly or indirectly) to treatment of a given medical condition but it may be appropriate to introduce regulatory regions which, in combination with the genes already present in the cell, can provide a therapeutic benefit.

The nucleic acid molecule of the vector is typically DNA but may, for example where the vector is an RNA virus, be RNA. Non-viral vectors may contain cDNA and the nucleic acid may be linear or circular, e.g. as with plasmid DNA. DNA may be single or double-stranded.

Where the nucleic acid encodes a protein which it is desired to express in transfected cells (e.g., an interfering fragment of MBP), the nucleic acid molecule will typically also comprise an operably linked promoter and possibly other regulatory sequences. For certain vectors, in particular viral vectors, the nucleic acid will also encode structural and other proteins involved with the generation of further vectors which can go on to transfect other cells, e.g. the gag, pol and env genes of an adenovirus. The design, construction and use of such expression vectors are familiar to those of skill in the art and well described in the literature, including appropriate pharmaceutical formulations in which to carry the plasmid or other vector.

The concentration of the nucleic acid delivered will vary depending on the vector chosen, the route and site of administration, and the disease state to be treated, but may be optimised by persons of skill in the art. Suitable dosages for intravenous administration include between 5 and 50 mg of plasmid in a concentration of e.g. 10-100 µg/ml of physiological saline.

According to a further aspect, the present invention provides the use of a nucleic acid molecule that encodes a species of MBP or an interfering fragment of MBP in the manufacture of a medicament for introduction into a region of the body of a subject to treat said subject with the peptide by gene therapy.

TABLE 1

Single-letter code of the natural amino acids

G Glycine (Gly)
P Proline (Pro)
A Alanine (Ala)
V Valine (Val)
L Leucine (Leu)
I Isoleucine (Ile)
M Methionine (Met)
C Cysteine (Cys)
F Phenylalanine (Phe)
Y Tyrosine (Tyr)
W Tryptophan (Trp)
H Histidine (His)
K Lysine (Lys)
R Arginine (Arg)
Q Glutamine (Gln)
N Asparagine (Asn)
E Glutamic Acid (Glu)
D Aspartic Acid (Asp)
S Serine (Ser)
T Threonine (Thr)

TABLE 2

Fragments of MBP Comprising the "KRG Motif" (KRGX$_1$X$_2$X$_3$X$_4$X$_5$X$_6$X$_7$X$_8$) (SEQ ID NO: 20).
Code: The single-letter code for the natural amino acids (see Table 1) is used. X$_1$ represents any 5 one of the natural amino acids at the first position following KRG, X$_2$ any one of the natural amino acids at the second position to follow KRG, etc.

| | |
|---|---|
| KRGX$_1$X$_2$X$_3$X$_4$X$_5$X$_6$X$_7$X$_8$ | (SEQ ID NO: 20) |
| KRGSGKVWPXX | (SEQ ID NO: 21) |
| KRGSGKDXHXX | (SEQ ID NO: 22) |
| KRGXXXXXXLK | (SEQ ID NO: 23) |
| KRGXXXXXXTR | (SEQ ID NO: 24) |
| KRGXXXXXXHA | (SEQ ID NO: 25) |

TABLE 3

KRG 11-mers in Specific Isoforms of MBP

| | | |
|---|---|---|
| SEQ ID NO: 2 | KRGSGKDSHHP | (in isoforms 3 and 4 of *homo sapiens* MBP) |
| SEQ ID NO: 27 | KRGRKQCKTHP | (in isoforms a, b and c of *homo sapiens* ApPP) |
| SEQ ID NO: 28 | KRGSGKVPWLK | (in isoforms 1 and 2 of *homosapiens* MBP) |
| SEQ ID NO: 29 | KRGSGKVPWLK | (in isoforms 1 and 3 of rat MBP) |
| SEQ ID NO: 30 | KRGSGKVPWLK | (in isoforms 1, 2 and 4 of *Mus muscullus* MBP) |
| SEQ ID NO: 31 | KRGSGKDSHTR | (in isoforms 2, 4, and 5 of rat MBP) |
| SEQ ID NO: 32 | KRGSGKDGHHA | (in MBP of *Sus scrofa*) |

Expression, isolation and purification of MBP and fragments thereof may be accomplished by any suitable technique, including the utilization of expression systems known in the art. The polynucleotide that encodes KRGSGKDSHHP (SEQ ID NO: 2), for example, may be operably inserted into a commercially available expression vector by recombinant techniques known in the art. Typically the polynucleotide will be inserted downstream (or 3') of, and operably linked to, a control or regulatory sequence. As used herein, "control sequence" and "regulatory sequence" are used interchangeably to include a promoter, enhancer-promoter combination, or other sequence that effects the expression or transcription of the downstream polynucleotide sequence. A promoter is a transcriptional regulatory element composed of a region of a DNA molecule typically within 100 nucleotide pairs in front of (upstream of) the point at which transcription starts. Another transcriptional regulatory element is an enhancer, which provides specificity in terms of time, location, and expression level. Unlike a promoter, an enhancer can function when located at variable distances from the transcription site, provided a promoter is present. An enhancer can also be located downstream of the transcription initiation site. Other regulatory sequences include transcription termination sequence, internal ribosome entry sites (RES), and the like.

Typically, to bring a coding sequence under control of a promoter, it is necessary to position the translation initiation site of the translational reading frame of the gene encoding the peptide or polypeptide between one and about fifty nucleotides downstream (3') of the promoter. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast a-mating factors, to name a few.

Expression vectors and methods for their construction are known to those skilled in the art (Ausubel et al.). Suitable vectors include plasmids, and viral vectors such as herpes viruses, retroviruses, canary poxviruses, adenoviruses and adeno-associated viruses, among others, and derivatives thereof.

A polynucleotide and regulatory sequences are "operably linked" when they are connected in such a way as to permit expression when the coding sequence of the polynucleotide of interest is bound to the regulatory sequences, e.g., within an expression vector. An origin of replication that confers the ability to replicate in the desired host cells, and a selection gene (e.g., $kan^r$, $amp^r$) by which transformants are identified, are generally incorporated into the expression vector.

An expression vector comprising a polynucleotide encoding a peptide, e.g., KRGSGKDSHHP (SEQ ID NO:2), may be used to prepare the polypeptide. A method for producing polypeptides comprises culturing host cells transformed or tranfected with a recombinant expression vector encoding the polypeptide, under conditions that promote expression of the polypeptide, then recovering the expressed polypeptides from the cells or from culture medium in which the host cell is grown. The procedure for purifying the expressed polypeptides will vary according to the type of host cells employed, and whether the polypeptide is membrane-bound or is a secreted soluble form of the polypeptide.

In addition, a sequence encoding an appropriate signal peptide (native or heterologous) can be incorporated into expression vectors. A DNA sequence for a signal peptide may be fused in frame to a polynucleotide encoding, for example, KRGSGKDSHHP (SEQ ID NO:2), so that the polynucleotide is initially transcribed, and the mRNA translated, into a fusion protein comprising the signal peptide. Signal peptides may be employed that direct transmembrane proteins to the cell surface or different signal peptides may be used that promote the secretion of a soluble form of the protein. Generally, the signal peptide is cleaved during maturation of the protein. A polynucleotide encoding a localization sequence, or signal sequence, can be ligated or fused at the 5' terminus of a polynucleotide encoding a polypeptide of, for example, KRGSGKDSHHP (SEQ ID NO:2), such that the signal peptide is located at the amino terminal end of the resulting fusion polynucleotide/polypeptide. In eukaryotes, the signal peptide functions to transport the fusion polypeptide across the endoplasmic reticulum. The secretory protein is then transported through the Golgi apparatus, into secretory vesicles and into the extracellular space or, preferably, the external environment. Signal peptides, which can be utilized according to the invention, include pre-pro peptides, which contain a proteolytic enzyme recognition site.

Suitable host cells for expression of polypeptides include prokaryotes (e.g., *E. coli*), yeast, plant cells, and insect or higher eukaryotic cells, including in vivo cells of a subject for the purpose of treating the subject with a peptide having the sequence KRGSGKDSHHP (SEQ ID NO:2), for example, or functional variants thereof. Most typically, yeast or mammalian cells are used. Appropriate cloning and expression vectors for use with bacterial, fungal, yeast, and mammalian cellular hosts are described, for example, in Pouwels et al. Cloning Vectors: A Laboratory Manual, Elsevier, New York, (1985). Cell-free translation systems could also be employed to produce polypeptides using RNAs derived from DNA constructs disclosed herein.

Suitable prokaryotic host cells for transformation may be gram-negative or gram-positive, and include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine (met) residue to facilitate expression of the recombinant polypeptide in the prokaryotic host cell. The N-terminal met may be cleaved from the expressed recombinant polypeptide.

Expression vectors for use in prokaryotic host cells generally comprise one or more phenotypic selectable marker genes, which may include, for example, a gene encoding a protein that confers antibiotic resistance or that supplies an autotrophic requirement. Useful prokaryotic expression vectors include those derived from commercially available plasmids such as the cloning vector pBR322 (ATCC 37017), with ampicillin and tetracycline resistance genes. Other suitable vectors include pKK223-3 (Pharmacia Fine Chemicals, Uppsala, Sweden) and pGEM1 (Promega Biotec, Madison, Wis., USA). An appropriate promoter and a polynucleotide sequence encoding the desired polypeptide may be inserted into the vector.

Promoter sequences commonly used for recombinant prokaryotic host cell expression vectors include β-lactamase (penicillinase), lactose promoter system (Chang et al., Nature 275:615, 1978; and Goeddel et al., Nature 281:544, 1979), tryptophan (trp) promoter system (Goeddel et al., Nucl. Acids Res. 8:4057, 1980) and tac promoter (Maniatis et al., Molecular Cloning: A Laboratory Manual, first ed., Cold Spring Harbor Laboratory, p. 412, 1982). A particularly useful prokaryotic host cell expression system employs a phage γPL promoter and a ci857ts thermolabile repressor sequence. Plasmid vectors available from the American Type Culture Collection which incorporate derivatives of the) γPL promoter include plasmid pHUB2 (resident in *E. coli* strain JMB9, ATCC 37092) and pPLc28 (resident in *E. coli* RR1, ATCC 53082).

Alternatively, the polypeptides may be expressed in yeast host cells, such as from the *Saccharomyces* genus (e.g., *S. cerevisiae*). Alternatively, *Pichia*, *Kluyveromyces*, or other yeast genera may be employed. Yeast vectors will often contain an origin of replication sequence from a 2 mu yeast plasmid, an autonomously replicating sequence (ARS), a promoter region, sequences for polyadenylation, sequences for transcription termination, and a selectable marker gene. Suitable promoter sequences include those derived from the yeast metallothionein or 3-phosphoglycerate kinase genes (Hitzeman et al., J. Biol. Chem. 255:2073, 1980) or other genes encoding glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are known in the art (e.g., see in Hitzeman, EPA-73,657; Russell et al., J. Biol. Chem. 258:2674, 1982; and Beier et al., Nature 300:724, 1982).

The yeast α-factor leader sequence may be employed to direct secretion of the polypeptide, and often is inserted between the promoter sequence and the structural gene sequence (e.g., Kurj an et al., Cell 30:933, 1982 and Bitter et al., Proc. Natl. Acad. Sci. USA 81:5330, 1984).

Yeast transformation protocols are known to those of skill in the art, including a protocol involving selection for Trp$^+$ transformants in a medium containing yeast nitrogen base, casamino acids, glucose, 10 mg/ml adenine and 20 mg/ml uracil (see, e.g., Hirmen et al., Proc. Natl. Acad. Sci. USA 75:1929, 1978). In other protocols, yeast cells transformed by vectors containing an ADH2 promoter sequence may be grown in a "rich" medium, An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or insect host cell culture systems also may be employed to express recombinant polypeptides, such as the baculovirus systems reviewed by Luckow and Summers, Bio/Technology 6:47 (1988), Established cell lines of mammalian origin also may be employed. Examples of suitable mammalian host cell lines include the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (EMBO J. 10: 2821, 1991).

Established methods for introducing polynucleotides into mammalian cells have been described (Kaufman, R. J., Large Scale Mammalian Cell Culture, 1990, pp. 15-69). Additional protocols using commercially available reagents, such as Lipofectamine lipid reagent (Gibco/BRL) or Lipofectamine-Plus lipid reagent, can be used to transfect cells (Feigner et al., Proc. Natl. Acad. Sci. USA 84:7413-7417, 1987). In addition, electroporation can be used to transfect mammalian cells using conventional procedures, such as those in Sambrook et al., 1989. Selection of stable transformants can be performed using methods known in the art, such as, for example, resistance to cytotoxic drugs. Kaufman et al., Meth. in Enzymology 185:487-511, 1990, describes several selection schemes, such as dihydrofolate reductase (DHFR) resistance. A suitable host strain for DHFR selection is CHO strain DX-B 11, which is deficient in DHFR (Urlaub and Chasin, Proc. Natl. Acad. Sci. USA 77:4216-4220, 1980). A plasmid expressing the DHFR cDNA can be introduced into strain DX-B 11, and only cells that contain the plasmid can grow in the appropriate selective media. Other examples of selectable markers include genes conferring resistance to antibiotics, such as G418 and hygromycin B, which permit selection of cells harboring the vector on the basis of resistance to these agents.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. Polynucleotide sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., Nature 273: 113, 1978; Kaufman, Meth. in Enzymology, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., Animal Cell Technology, 1997, pp. 529-534 and PCT Application WO 97/25420) and the tripartite leader (TPL) and VA gene RNAs from Adenovirus 2 (Gingeras et al., J. Biol. Chem. 257:13475-13491, 1982). The internal ribosome entry site (IRES) sequences of viral origin allows dicistronic mRNAs to be translated efficiently (Oh and Sarnow, Current Opinion in Genetics and Development 3:295-300, 1993; Ramesh et al., Nucleic Acids Research 24:2697-2700, 1996). Expression of a heterologous cDNA as part of a dicistronic mRNA followed by the gene for a selectable marker (e.g. DHFR) has been shown to improve transfectability of the host and expression of the heterologous polynucleotides (Kaufman, Meth. in Enzymology, 1990). Exemplary expression vectors that employ dicistronic mRNAs are pTR-DC/GFP described by Mosser et al., Biotechniques 22:150-161, 1997, and p2A5I described by Morris et al., Animal Cell Technology, 1997, pp. 529-534.

A useful high expression vector, pCAVNOT, has been described by Mosley et al., Cell 59:335-348, 1989. Other expression vectors for use in mammalian host cells can be constructed as disclosed by Okayama and Berg (Mol. Cell. Biol. 3:280, 1983). A useful system for stable high level expression of mammalian cDNAs in C127 murine mammary epithelial cells can be constructed substantially as described by Cosman et al. (Mol. Immunol. 23:935, 1986). A useful high expression vector, PMLSV N1/N4, described by Cosman et al., Nature 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAG® marker peptide to the N-terminus of a recombinant protein expressed by pFLAG® expression vectors, pDC311 is another specialized vector used for expressing proteins in CHO cells, pDC311 is characterized by a bicistronic sequence containing the genes of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Other useful fragments of MBP in certain embodiments of the invention include antisense or sense oligonucleotides comprising a single-stranded polynucleotide sequence (either RNA or DNA) capable of binding to target mRNA (sense) or DNA (antisense) sequences. Antisense or sense oligonucleotides, according to the present invention, comprise fragments of a polynucleotide having a nucleotide sequence as set forth in any of Tables 4-7 or sequences at least 95% identical to any one of them. Such a fragment generally comprises at least about 14 nucleotides, preferably from about 14 to about 30 nucleotides. The ability to derive an antisense or a sense oligonucleotide, based upon a nucleic acid sequence encoding a given protein is described in, for example, Stein and Cohen (Cancer Res. 48:2659, 1988) and van der Krol et al. BioTechniques 6:958, 1988).

TABLE 4

| Nucleotide Sequence for Isoform 1 of *Homo sapiens* MBP (SEQ ID NO: 41) |
|---|

Isoform 1: (NM_001025081.1)

| | | | | |
|---|---|---|---|---|
| 1 | ggacaacacc | ttcaaagaca | ggccctctga | gtccgacgag ctccagacca tccaagaaga |
| 61 | cagtgcagcc | acctccgaga | gcctggatgt | gatggcgtca cagaagagac cctcccagag |
| 121 | gcacggatcc | aagtacctgg | ccacagcaag | taccatggac catgccaggc atggcttcct |
| 181 | cccaaggcac | agagacacgg | gcatccttga | ctccatcggg cgcttctttg gcggtgacag |
| 241 | gggtgcgccc | aagcggggct | ctggcaaggt | accctggcta aagccgggcc ggagccctct |
| 301 | gccctctcat | gcccgcagcc | agcctgggct | gtgcaacatg tacaaggact cacaccaccc |
| 361 | ggcaagaact | gctcactacg | gctccctgcc | ccagaagtca cacggccgga cccaagatga |
| 421 | aaaccccgta | gtccacttct | tcaagaacat | tgtgacgcct cgcacaccac ccccgtcgca |
| 481 | gggaaagggg | agaggactgt | ccctgagcag | atttagctgg ggggccgaag gccagagacc |
| 541 | aggatttggc | tacggaggca | gagcgtccga | ctataaatcg gctcacaagg gattcaaggg |
| 601 | agtcgatgcc | cagggcacgc | tttccaaaat | ttttaagctg ggaggaagag atagtcgctc |
| 661 | tggatcaccc | atggctagac | gctgaaaacc | cacctggttc cggaatcctg tcctcagctt |
| 721 | cttaatataa | ctgccttaaa | actttaatcc | cacttgcccc tgttacctaa ttagagcaga |
| 781 | tgaccccctcc | cctaatgcct | gcggagttgt | gcacgtagta gggtcaggcc acggcagcct |
| 841 | accggcaatt | tccggccaac | agttaaatga | gaacatgaaa acagaaaacg gttaaaactg |
| 901 | tcccttttctg | tgtgaagatc | acgttccttc | ccccgcaatg tgccccccaga cgcacgtggg |
| 961 | tcttcagggg | gccaggtgca | cagacgtccc | tccacgttca cccctccacc cttggacttt |
| 1021 | cttttcgccg | tggctgcggc | accttgcgc | ttttgctggt cactgccatg gaggcacaca |
| 1081 | gctgcagaga | cagagaggac | gtgggcggca | gagaggactg ttgacatcca agcttccttt |
| 1141 | gtttttttttt | cctgtccttc | tctcacctcc | taaagtagac ttcatttttc ctaacaggat |
| 1201 | tagacagtca | aggagtggct | tactacatgt | gggagctttt ggtatgtgac atgcgggctg |
| 1261 | ggcagctgtt | agagtccaac | gtgggcagc | acagagaggg ggccacctcc ccaggccgtg |
| 1321 | gctgcccaca | caccccaatt | agctgaattc | gcgtgtggca gagggaggaa aaggaggcaa |
| 1381 | acgtgggctg | ggcaatggcc | tcacatagga | aacagggtct tcctggagat ttggtgatgg |
| 1441 | agatgtcaag | caggtggcct | ctggacgtca | ccgttgccct gcatggtggc cccagagcag |
| 1501 | cctctatgaa | caacctcgtt | tccaaaccac | agcccacagc cggagagtcc aggaagactt |
| 1561 | gcgcactcag | agcagaaggg | taggagtcct | ctagacagcc tcgcagccgc gccagtcgcc |
| 1621 | catagacact | ggctgtgacc | gggcgtgctg | gcagcggcag tgcacagtgg ccagcactaa |
| 1681 | ccctccctga | gaagataacc | ggctcattca | cttcctccca gaagacgcgt ggtagcgagt |
| 1741 | aggcacaggc | gtgcacctgc | tcccgaatta | ctcaccgaga cacacgggct gagcagacgg |
| 1801 | ccccgtggat | ggagacaaag | agctcttctg | accatatcct tcttaacacc cgctggcatc |

TABLE 4-continued

Nucleotide Sequence for Isoform 1 of *Homo sapiens* MBP (SEQ ID NO: 41)

```
1861  tcctttcgcg cctccctccc taacctactg acccaccttt tgattttagc gcacctgtga
1921  ttgataggcc ttccaaagag tcccacgctg gcatcaccct ccccgaggac ggagatgagg
1981  agtagtcagc gtgatgccaa aacgcgtctt cttaatccaa ttctaattct gaatgtttcg
2041  tgtgggctta ataccatgtc tattaatata tagcctcgat gatgagagag ttacaaagaa
2101  caaaactcca gacacaaacc tccaaatttt tcagcagaag cactctgcgt cgctgagctg
2161  aggtcggctc tgcgatccat acgtggccgc acccacacag cacgtgctgt gacgatggct
2221  gaacggaaag tgtacactgt tcctgaatat tgaaataaaa caataaactt ttaatggtaa
2281  aaaaaaaaaa aaaaaaaaaa
```

TABLE 5

Nucleotide Sequence for Isoform 2 of *Homo sapiens* MBP (SEQ ID NO:42)

Isoform 2: (NM_002385.2)
```
   1  ggacaacacc ttcaaagaca ggccctctga gtccgacgag ctccagacca tccaagaaga
  61  cagtgcagcc acctccgaga gcctggatgt gatggcgtca cagaagagac cctcccagag
 121  gcacggatcc aagtacctgg ccacagcaag taccatggac catgccaggc atggcttcct
 181  cccaaggcac agagacacgg gcatccttga ctccatcggg cgcttctttg gcggtgacag
 241  gggtgcgccc aagcggggct ctggcaaggt accctggcta agccgggcc ggagccctct
 301  gccctctcat gcccgcagcc agcctgggct gtgcaacatg tacaaggact cacaccaccc
 361  ggcaagaact gctcactacg gctccctgcc ccagaagtca cacggccgga cccaagatga
 421  aaaccccgta gtccacttct tcaagaacat tgtgacgcct cgcacaccac ccccgtcgca
 481  gggaaagggg gccgaaggcc agagaccagg atttggctac ggaggcagag cgtccgacta
 541  taaatcggct cacaagggat tcaagggagt cgatgcccag ggcacgcttt ccaaaatttt
 601  taagctggga ggaagagata gtcgctctgg atcacccatg gctagacgct gaaaacccac
 661  ctggttccgg aatcctgtcc tcagcttctt aatataactg ccttaaaact ttaatcccac
 721  ttgcccctgt tacctaatta gagcagatga cccctcccct aatgcctgcg gagttgtgca
 781  cgtagtaggg tcaggccacg gcagcctacc ggcaatttcc ggccaacagt taaatgagaa
 841  catgaaaaca gaaaacggtt aaaactgtcc ctttctgtgt gaagatcacg ttccttcccc
 901  cgcaatgtgc ccccagacgc acgtgggtct tcagggggcc aggtgcacag acgtccctcc
 961  acgttcaccc ctccacccct ggactttctt ttcgccgtgg ctgcggcacc cttgcgcttt
1021  tgctggtcac tgccatggag gcacacagct gcagagacag agaggacgtg ggcggcagag
1081  aggactgttg acatccaagc ttccttttgtt ttttttttcct gtccttctct cacctcctaa
1141  agtagacttc attttttccta acaggattag acagtcaagg agtggcttac tacatgtggg
1201  agcttttggt atgtgacatg cgggctgggc agctgttaga gtccaacgtg gggcagcaca
1261  gagagggggc cacctcccca ggccgtggct gcccacacac cccaattagc tgaattcgcg
1321  tgtggcagag ggaggaaaag gaggcaaacg tgggctgggc aatggcctca cataggaaac
1381  agggtcttcc tggagatttg gtgatggaga tgtcaagcag gtggcctctg gacgtcaccg
1441  ttgccctgca tggtggcccc agagcagcct ctatgaacaa cctcgtttcc aaaccacagc
1501  ccacagccgg agagtccagg aagacttgcg cactcagagc agaagggtag gagtcctcta
1561  gacagcctcg cagccgcgcc agtcgcccat agacactggc tgtgaccggg cgtgctggca
```

TABLE 5-continued

Nucleotide Sequence for Isoform 2 of *Homo sapiens* MBP (SEQ ID NO:42)

```
1621  gcggcagtgc acagtggcca gcactaaccc tccctgagaa gataaccggc tcattcactt
1681  cctcccagaa gacgcgtggt agcgagtagg cacaggcgtg cacctgctcc cgaattactc
1741  accgagacac acgggctgag cagacggccc cgtggatgga gacaaagagc tcttctgacc
1801  atatccttct taacacccgc tggcatctcc tttcgcgcct ccctccctaa cctactgacc
1861  cacctttga ttttagcgca cctgtgattg ataggccttc caaagagtcc cacgctggca
1921  tcaccctccc cgaggacgga gatgaggagt agtcagcgtg atgccaaaac gcgtcttctt
1981  aatccaattc taattctgaa tgtttcgtgt gggcttaata ccatgtctat taatatatag
2041  cctcgatgat gagagagtta caaagaacaa aactccagac acaaacctcc aaattttca
2101  gcagaagcac tctgcgtcgc tgagctgagg tcggctctgc gatccatacg tggccgcacc
2161  cacacagcac gtgctgtgac gatggctgaa cggaaagtgt acactgttcc tgaatattga
2221  aataaaacaa taaacttta atggtaaaaa aaaaaaaaaa aaaaaa
```

TABLE 6

Nucleotide Sequence for Isoform 3 of *Homo sapiens* MBP (SEQ ID NO: 43)

Isoform 3: (NM_001025090.1)
```
   1  ggacaacacc ttcaaagaca ggccctctga gtccgacgag ctccagacca tccaagaaga
  61  cagtgcagcc acctccgaga gcctggatgt gatggcgtca cagaagagac cctcccagag
 121  gcacggatcc aagtacctgg ccacagcaag taccatggac catgccaggc atggcttcct
 181  cccaaggcac agagacacgg gcatccttga ctccatcggg cgcttctttg gcggtgacag
 241  gggtgcgccc aagcggggct ctggcaagga ctcacaccac ccggcaagaa ctgctcacta
 301  cggctccctg ccccagaagt cacacggccg gacccaagat gaaaacccg tagtccactt
 361  cttcaagaac attgtgacgc ctcgcacacc accccgtcg cagggaaagg ggagaggact
 421  gtccctgagc agatttagct gggggggccga aggccagaga ccaggatttg gctacggagg
 481  cagagcgtcc gactataaat cggctcacaa gggattcaag ggagtcgatg cccagggcac
 541  gctttccaaa attttaagc tggaggaag agatagtcgc tctggatcac ccatggctag
 601  acgctgaaaa cccacctggt tccggaatcc tgtcctcagc ttcttaatat aactgcctta
 661  aaactttaat cccacttgcc cctgttacct aattagagca gatgacccct cccctaatgc
 721  ctgcggagtt gtgcacgtag tagggtcagg ccacggcagc ctaccggcaa tttccggcca
 781  acagttaaat gagaacatga aaacagaaaa cggttaaaac tgtccctttc tgtgtgaaga
 841  tcacgttcct tcccccgcaa tgtgccccca gacgcacgtg ggtcttcagg gggccaggtg
 901  cacagacgtc cctccacgtt caccccctcca cccttggact ttcttttcgc cgtggctgcg
 961  gcacccttgc gcttttgctg gtcactgcca tggaggcaca cagctgcaga gacagagagg
1021  acgtgggcgg cagagaggac tgttgacatc caagcttcct ttgttttttt ttcctgtcct
1081  tctctcacct cctaaagtag acttcatttt tcctaacagg attagacagt caaggagtgg
1141  cttactacat gtgggagctt tggtatgtg acatgcgggc tgggcagctg ttagagtcca
1201  acgtggggca gcacagagag ggggccacct ccccaggccg tggctgccca cacacccaa
1261  ttagctgaat tcgcgtgtgg cagagggagg aaaaggaggc aaacgtgggc tgggcaatgg
1321  cctcacatag gaaacagggt cttcctggag atttggtgat ggagatgtca agcaggtggc
1381  ctctggacgt caccgttgcc ctgcatggtg gccccagagc agcctctatg aacaacctcg
```

TABLE 6-continued

Nucleotide Sequence for Isoform 3 of *Homo sapiens* MBP (SEQ ID NO: 43)

```
1441  tttccaaacc acagcccaca gccggagagt ccaggaagac ttgcgcactc agagcagaag
1501  ggtaggagtc ctctagacag cctcgcagcc gcgccagtcg cccatagaca ctggctgtga
1561  ccgggcgtgc tggcagcggc agtgcacagt ggccagcact aaccctccct gagaagataa
1621  ccggctcatt cacttcctcc cagaagacgc gtggtagcga gtaggcacag gcgtgcacct
1681  gacccgaat tactcaccga gacacacggg ctgagcagac ggccccgtgg atggagacaa
1741  agagctcttc tgaccatatc cttcttaaca cccgctggca tctcctttcg cgcctccctc
1801  cctaacctac tgacccacct ttttgatttta gcgcacctgt gattgatagg ccttccaaag
1861  agtcccacgc tggcatcacc ctccccgagg acggagatga ggagtagtca gcgtgatgcc
1921  aaaacgcgtc ttcttaatcc aattctaatt ctgaatgttt cgtgtgggct taataccatg
1981  tctattaata tatagcctcg atgatgagag agttacaaag aacaaaactc cagacacaaa
2041  cctccaaatt tttcagcaga agcactctgc gtcgctgagc tgaggtcggc tctgcgatcc
2101  atacgtggcc gcacccacac agcacgtgct gtgacgatgg ctgaacggaa agtgtacact
2161  gttcctgaat attgaaataa aacaataaac ttttaatggt aaaaaaaaaa aaaaaaaaaa
2221  aa
```

TABLE 7

Nucleotide Sequence for Isoform 4 of *Homo sapiens* MBP (SEQ ID NO: 44)

Isoform 4: (NM_001025092.1)
```
   1  ggacaacacc ttcaaagaca ggccctctga gtccgacgag ctccagacca tccaagaaga
  61  cagtgcagcc acctccgaga gcctggatgt gatggcgtca cagaagagac cctcccgag
 121  gcacggatcc aagtacctgg ccacagcaag taccatggac catgccaggc atggcttcct
 181  cccaaggcac agagacacgg gcatccttga ctccatcggg cgcttctttg gcggtgacag
 241  gggtgcgccc aagcggggct ctggcaagga ctcacaccac ccggcaagaa ctgctcacta
 301  cggctccctg ccccagaagt cacacggccg gacccaagat gaaaaccccg tagtccactt
 361  cttcaagaac attgtgacgc ctcgcacacc accccgtcg cagggaaagg gggccgaagg
 421  ccagagacca ggatttggct acgaggcag agcgtccgac tataaatcgg ctcacaaggg
 481  attcaaggga gtcgatgccc agggcacgct ttccaaaatt tttaagctgg gaggaagaga
 541  tagtcgctct ggataccca tggctagacg ctgaaaaccc acctggttcc ggaatcctgt
 601  cctcagcttc ttaatataac tgccttaaaa ctttaatccc acttgcccct gttacctaat
 661  tagagcagat gacccctccc ctaatgcctg cggagttgtg cacgtagtag ggtcaggcca
 721  cggcagccta ccggcaattt ccggccaaca gttaaatgag aacatgaaaa cagaaaacgg
 781  ttaaaactgt cccttctgt gtgaagatca cgttccttcc cccgcaatgt gccccagac
 841  gcacgtgggt cttcagggg ccaggtgcac agacgtccct ccacgttcac ccctccaccc
 901  ttggacttc ttttcgccgt ggctgcggca cccttgcgct tttgctggtc actgccatgg
 961  aggcacacag ctgcagagac agagaggacg tgggcggcag agaggactgt tgacatccaa
1021  gcttcctttg tttttttttc ctgtccttct ctcacctcct aaagtagact tcatttttcc
1081  taacaggatt agacagtcaa ggagtggctt actacatgtg ggagcttttg gtatgtgaca
1141  tgcgggctgg gcagctgtta gagtccaacg tggggcagca cagagagggg gccacctccc
1201  caggccgtgg ctgcccacac accccaatta gctgaattcg cgtgtggcag agggaggaaa
```

TABLE 7-continued

Nucleotide Sequence for Isoform 4 of *Homo sapiens* MBP (SEQ ID NO: 44)

| | | | | | |
|---|---|---|---|---|---|
| 1261 | aggaggcaaa | cgtgggctgg | gcaatggcct | cacataggaa | acagggtctt | cctggagatt |
| 1321 | tggtgatgga | gatgtcaagc | aggtggcctc | tggacgtcac | cgttgccctg | catggtggcc |
| 1381 | ccagagcagc | ctctatgaac | aacctcgttt | ccaaaccaca | gcccacagcc | ggagagtcca |
| 1441 | ggaagacttg | cgcactcaga | gcagaagggt | aggagtcctc | tagacagcct | cgcagccgcg |
| 1501 | ccagtcgccc | atagacactg | gctgtgaccg | ggcgtgctgg | cagcggcagt | gcacagtggc |
| 1561 | cagcactaac | cctccctgag | aagataaccg | gctcattcac | ttcctcccag | aagacgcgtg |
| 1621 | gtagcgagta | ggcacaggcg | tgcacctgct | cccgaattac | tcaccgagac | acacgggctg |
| 1681 | agcagacggc | cccgtggatg | gagacaaaga | gctcttctga | ccatatcctt | cttaacaccc |
| 1741 | gctggcatct | cctttcgcgc | ctccctccct | aacctactga | cccaccttt | gattttagcg |
| 1801 | cacctgtgat | tgataggcct | tccaaagagt | cccacgctgg | catcaccctc | cccgaggacg |
| 1861 | gagatgagga | gtagtcagcg | tgatgccaaa | acgcgtcttc | ttaatccaat | tctaattctg |
| 1921 | aatgtttcgt | gtgggcttaa | taccatgtct | attaatatat | agcctcgatg | atgagagagt |
| 1981 | tacaaagaac | aaaactccag | acacaaacct | ccaaattttt | cagcagaagc | actctgcgtc |
| 2041 | gctgagctga | ggtcggctct | gcgatccata | cgtggccgca | cccacacagc | acgtgctgtg |
| 2101 | acgatggctg | aacggaaagt | gtacactgtt | cctgaatatt | gaaataaaac | aataaacttt |
| 2161 | taatggtaaa | aaaaaaaaaa | aaaaaaaaa | | | |

Binding of antisense or sense oligonucleotides to target nucleic acids results in the formation of duplexes that block or inhibit protein expression by one of several means, including enhanced degradation of the mRNA by RNAse H, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleic acids.

Other examples of sense or antisense oligonucleotides include those oligonucleotides which are covalently linked to organic moieties, such as those described in WO 90/10448, and other moieties that increases affinity of the oligonucleotide for a target nucleic acid, such as poly-(L)-lysine. Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid by any gene transfer method, including, for example, lipofection, CaPO$_4$-mediated DNA transfection, electroporation, or by using gene transfer vectors such as Epstein-Barr virus or adenovirus.

Sense or antisense oligonucleotides also may be introduced into a cell containing the target nucleic acid by formation of a conjugate with a ligand-binding molecule, as described in WO 91/04753. Suitable ligand binding molecules include, but are not limited to, cell surface receptors, growth factors, other cytokines, or other ligands that bind to cell surface receptors. Preferably, conjugation of the ligand-binding molecule does not substantially interfere with the ability of the ligand-binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid by formation of an oligonucleotide-lipid complex, as described in WO 90/10448. The sense or antisense oligonucleotide-lipid complex is preferably dissociated within the cell by an endogenous lipase.

Species of MBP or fragments thereof may also be used as diagnostic markers of a disease or disorder characterized by abnormal fibrillization. One may, for example, compare a nucleic acid target in a MBP gene obtained from an affected subject with that of a control nucleic acid target in a MBP gene from a normal subject, and then detect differences in sequence or amount between the target region and the control target region, as an indication of the disease or disorder. A method for detecting a species of MBP or an abnormal code for an MBP fragment in a sample as a diagnostic marker of a disease or disorder characterized by abnormal fibrillization may comprise (a) contacting the sample with a nucleic acid probe which hybridizes under hybridization assay conditions to a nucleic acid target encoding the MBP or abnormal fragment thereof or the nucleic acid sequence complements thereof; and (b) detecting the presence or amount of the probe:nucleic acid target region hybrid as an indication of the disease.

In one embodiment, the invention provides a method that employs a recombinant cell or tissue comprising a nucleic acid molecule encoding MBP or a variant thereof, or a fragment thereof. Such a cell or tissue may be grown or differentiated and introduced into an individual in need of treatment.

In such fashion, the nucleic acid may be introduced into an individual by cellular administration of cells or tissues, rather than by direct injection. Accordingly, cells or tissues may be taken from the individual in question, modified so as to contain cells expressing the MBP or the fragment and then reintroduced into the same individual. Mesenchymal stem cells and bone marrow stem cells are examples of cells that may be modified and used in such fashion.

Methods for using nucleic acid probes include detecting the presence or amount of RNA transcript of MBP or a fragment thereof in a sample by contacting the sample with a nucleic acid probe under conditions such that hybridization occurs and detecting the presence or amount of the probe bound to the RNA. The nucleic acid duplex formed may be used in the identification of the sequence of the nucleic acid detected (Nelson et al., in NONISOTOPIC DNA PROBE TECHNIQUES, Academic Press, San Diego, Kxicka, ed., p. 275, 1992, hereby incorporated by reference herein in its entirety, including any drawings, figures, or tables).

Antibodies specific for a species of MBP, regions thereof, or fragments thereof are useful in certain embodiments of the invention. A preferred antibody binds to the MBP or fragment thereof with greater affinity than it binds to other inhibitor polypeptides under specified conditions. Antibodies or antibody fragments are polypeptides that contain regions that can bind other polypeptides. An antibody or antibody fragment with specific binding affinity to the MBP or MBP fragment can be isolated, enriched, or purified from a prokaryotic or eukaryotic organism. Routine methods known to those skilled in the art enable production of antibodies or antibody fragments, in both prokaryotic and eukaryotic organisms. Purification, enrichment, and isolation of antibodies, which are polypeptide molecules, are described above.

Antibodies having specific binding affinity to a species of MBP, regions thereof, or fragments thereof may be used in embodiments of the invention that provide methods for detecting the presence and/or amount of the MBP or MBP fragment in a sample. The sample is contacted with the antibody under conditions such that an immunocomplex forms and the presence and/or amount of the antibody conjugated to the MBP or MBP fragment is detected. The polypeptide need not be identical to any wild-type species of MBP, or region thereof, or fragment thereof. A sequence at least about 90% identical to an amino acid sequence of that species of MBP or domain or fragment thereof is encompassed in these methods. Preferably the polypeptide has at least about 91%, 92%, 93%, 94%, 95%, 96%, 97%, 98% 99% or 100% identity therewith. By "specific binding affinity" is meant that the antibody binds to the MBP or MBP fragment with greater affinity than it binds to other polypeptides under specified conditions. Antibodies can be used to identify an endogenous source of a species of MBP or a fragment thereof, and for its immunolocalization within or outside cell.

Antibodies or antibody fragments having specific binding affinity to a species of MBP or to a fragment thereof may be used in methods for detecting the presence and/or amount of the polypeptide in a sample by probing the sample with the antibody under conditions suitable for the MBP-antibody immunocomplex formation and detecting the presence and/or amount of the antibody conjugated to the polypeptide. Diagnostic kits for performing such methods may be constructed to include antibodies or antibody fragments specific for the MBP as well as a conjugate of a binding partner of the antibodies or the antibodies themselves.

An antibody or antibody fragment with specific binding affinity to a species of MBP or to a fragment thereof can be, isolated, enriched, or purified from a prokaryotic or eukaryotic organism. Routine methods known to those skilled in the art enable production of antibodies or antibody fragments, in both prokaryotic and eukaryotic organisms. Purification, enrichment, and isolation of antibodies, which are polypeptide molecules, are described above.

Antibodies having specific binding affinity to a species of MBP or to a fragment thereof, may be used in methods for detecting the presence and/or amount of the polypeptide in a sample by contacting the sample with the antibody under conditions such that an immunocomplex forms and detecting the presence and/or amount of the antibody conjugated to the polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

In another aspect, the invention features a hybridoma which produces an antibody having specific binding affinity to a species of MBP or a polypeptide domain thereof or a fragment thereof that is encoded by any of the nucleic acids, the nucleic acid sequences of which are listed in Tables 4-7, and nucleic acids at least 95% homologous thereto.

The following examples are provided in order to demonstrate and further illustrate certain preferred embodiments and aspects of the present invention and are not to be construed as limiting the scope thereof.

Example 1

Identification of the Fibrillar Amyloid Binding Domain of AβPP

Deposition of fibrillar amyloid-β protein (Aβ) in senile plaques and in the walls of cerebral blood vessels is a key pathological feature of Alzheimer's disease and certain related disorders. Fibrillar Aβ deposition is intimately associated with neuronal and cerebrovascular cell death both in vivo and in vitro. Similarly, accumulation of the Aβ protein precursor (AβPP) is also observed at sites of fibrillar Aβ deposition. Recently, fibrillar Aβ, but not unassembled Aβ, was shown to promote the specific binding of AβPP through its cysteine-rich, amino-terminal region (Melchor, J. P., and Van Nostrand, W. E. (2000) J. Biol. Chem. 275, 9782-9791). The present study sought to determine the precise site on AβPP that facilitates its binding to fibrillar Af3. A series of synthesized overlapping peptides spanning the cysteine-rich, amino-terminal region of AβPP were used as competitors for AβPP binding to fibrillar Aβ. A peptide spanning residues 105-119 of AβPP competitively inhibited AβPP binding to fibrillar Aβ in a solid-phase binding assay and on the surface of cultured human cerebrovascular smooth muscle cells. Alanine-scanning mutagenesis of residues 105-117 within glutathione S-transferase (GST)-AβPP-(18-119) revealed that $His^{110}$, $Val^{112}$, and $Ile^{113}$ are key residues that facilitate AβPP binding to fibrillar Aβ. These specific residues belong to a common strand within this region of AβPP. Wild-type GST-AβPP-(18-119) protected cultured human cerebrovascular smooth muscle cells from Aβ-induced toxicity whereas H110A mutant GST-AβPP-(18-119) did not. Wild-type GST-AβPP-(18-119) bound to different isoforms of fibrillar Aβ and fibrillar amylin peptides whereas H110A mutant and I113A mutant GST-AβPP-(18-119) were substantially less efficient in binding to each fibrillar peptide. Applicant concludes that $His^{110}$, $Val^{112}$, and $Ile^{113}$, residing in a common β-strand region within AβPP-(18-119), comprise a domain that mediates the binding of AβPP to fibrillar peptides.

Fibrillar amyloid-β protein (Aβ) deposition in senile plaques in the neuropil and in the walls of cerebral blood vessels is a common pathologic feature of patients with Alzheimer's disease (AD) and certain related disorders including Down's syndrome and hereditary cerebral hemorrhage with amyloidosis of the Dutch type (1). Aβ is a 39-43-amino acid peptide that has the propensity to self-assemble into insoluble, β-sheet-containing fibrils. Aβ is proteolytically derived from a large type I integral membrane precursor protein, termed the amyloid β-protein precursor (AβPP), encoded by a gene located on chromosome 21. In this regard, full-length AβPP is proteolytically cleaved by an enzyme, termed β-secretase, at the amino terminus of the Aβ domain. An aspartyl proteinase named BACE (β-site AβPP-Cleaving Enzyme) has been identified as the β-secretase enzyme. Subsequent cleavage of the remaining amyloidogenic membrane spanning AβPP carboxyl-terminal fragment by an enzyme termed γ-secretase liberates the 40- or 42-amino acid residue Aβ peptide. Although the exact identity of γ-secretase remains unclear, studies suggest that the presenilin proteins may function as this enzyme or as a required cofactor for γ-secretase function. Alternatively, full-length AβPP can be proteolytically processed by an enzyme termed α-secretase through the Aβ domain. This cleavage event generates a non-amyloidogenic membrane spanning carboxyl-terminal fragment and truncated secretory forms of AβPPα (sAβPP)α that are released into the extracellular environment.

Cerebrovascular Aβ deposition, known as cerebral amyloid angiopathy, is accompanied by smooth muscle cell degeneration, suggesting a toxic effect of Aβ to these cells in vivo. These degenerating smooth muscle cells have been implicated in the overproduction of AβPP and Aβ in the cerebral vessel wall, further suggesting the active involvement of these cells in the progression of this cerebrovascular pathology. Similar to these in vivo observations, Aβ-(1-42) (the more pathogenic form of the wild-type peptide), causes severe cellular degeneration accompanied by a marked increase in the level of cell-associated AβPP in cultured human cerebrovascular smooth muscle (HCSM) cells. More recent studies have demonstrated that mutations associated with familial forms of cerebral amyloid angiopathy (E22Q Dutch, E22K Italian, and D23N Iowa) markedly enhance both the fibrillogenic and cerebrovascular pathogenic properties of Aβ toward cultured HCSM cells. The studies showed that these pathogenic forms of Aβ assemble into an elaborate network of fibrils on the surfaces of HCSM cells. Furthermore, fibril assembly of pathogenic Aβ on the cell surface is required for inducing downstream pathologic responses in HCSM cells, including cell-surface accumulation of sAβPPα, degradation of vascular smooth muscle cell α-actin, and ultimately an apoptotic cell death.

The accumulation of sAβPPα has been shown to be mediated by its high-affinity binding to the Aβ fibrils that assemble on the HCSM cell surface. This event coincides with the induction of smooth muscle cell α-actin degradation and cell death. It is noteworthy that an interaction between fibrillar Aβ and AβPP also has been implicated in neuronal cell death in vitro. Finally, Aβ fibril binding to Kunitz proteinase inhibitory (KPI) domain containing forms of AβPP can enhance its proteinase inhibitory property. Together, the findings indicate that interactions between fibrillar Aβ binding and AβPP may have significant physiological and pathological consequences.

In the present study, the precise site in the cysteine-rich, amino-terminal region of AβPP that facilitates binding to fibrillar forms of Aβ is identified. The investigations show that residues $His^{110}$, $Val^{112}$, and $Ile^{113}$, all on a common β-strand region within AβPP, comprise a domain on AβPPP that is involved with its binding to fibrillar Aβ peptides. This domain also mediates the binding of AβPP to other fibrillar peptides, suggesting that this region may participate in other biologically important interactions.

Experimental Procedures:

Materials—

Aβ peptides were synthesized by solid-phase Fmoc ((N-(9-fluorenyl)methoxycarbonyl) amino acid chemistry, purified by reverse phase-HPLC, and structurally characterized. Amylin peptide was obtained from Bachem (San Carlos, Calif.). For preparation of amyloid fibrils, Aβ peptides or amylin were resuspended to a final concentration of 1.25 mM in 50 mM Tris-HCl, 150 mM NaCl, pH 7.4 and incubated at 37° C. for 3 days. The β-sheet, fibrillar structure of each peptide was confirmed by circular dichroism spectroscopy and electron microscopy. For cell culture experiments, lyophilized Aβ peptide was first resuspended to a concentration of 250 µM in sterile distilled water. Prior to addition to HCSM cells, the peptide was diluted to a final concentration of 25 µM in serum-free culture medium. The set of overlapping 15 amino acid peptides spanning AβPP residues 18-119 was prepared by Multiple Peptide Systems (San Diego, Calif.). Wild-type sAβPPα-770 was purified and was then biotinylated according to the manufacturer's protocol using the Pierce EZ Sulfo-link Biotin (Rockford, Ill.). The anti-AβPP mouse monoclonal antibody (mAb) P2-1, which specifically recognizes an epitope in the amino-terminal region of human AβPP, was prepared. The anti-AβPP mAb 22C11 was obtained from Chemicon (Temecula, Calif.). Secondary peroxidase-coupled sheep anti-mouse IgG and peroxidase-conjugated streptavidin were purchased from Amersham Biosciences. Supersignal Dura West chemiluminescence substrate was purchased from Pierce (Rockford, Ill.).

Solid-Phase Binding Assay—

Aβ peptides or amylin were assembled into fibrils as described above. For most studies fibrillar forms of Dutch-type Aβ40 were used since this mutant form of Aβ exhibits enhanced fibrillogenic and pathogenic properties compared with wild-type Aβ. Two µg of each fibrillar Aβ peptide, fibrillar amylin, or ovalbumin in 100 µl of phosphate-buffered saline (PBS) were dried in a 96-well microtiter plate (Corning, Cambridge, Mass.) overnight at 37° C. The wells were rinsed with PBS three times and blocked with 100 µl per well PBS containing 1 mg/ml bovine serum albumin (BSA) for 1 hour at room temperature. After rinsing three times with PBS, known concentrations of biotinylated sAβPPα in PBS containing 0.1 mg/ml BSA were incubated in triplicate (100 µl per well) for 1 hour at room temperature. After rinsing the wells with PBS three times, 100 µl of streptavidin conjugated to horseradish peroxidase in PBS containing 0.1 mg/ml BSA (1:800) was added for 1 hour at room temperature. The binding of biotinylated sAβPPα was detected using the colorimetric substrate o-phenylenediamine dihydrocholride as described by the manufacturer (InVitrogen). Briefly, the substrate was diluted in buffer (0.1 M sodium citrate, pH 4.5) to a final concentration of 1 mg/ml. $H_2O_2$ was added to a final concentration of 0.012% immediately before 100 µl of the substrate was added to each microtiter well. The solution was developed for ≈30 min at room temperature and quenched by the addition of 50 µl of 4N $H_2SO_4$ to each well. The conversion of the colorimetric substrate was measured at a wavelength of 490 nm using a Molecular Dynamics $V_{max}$ kinetic plate reader (Sunnyvale, Calif.).

Alternatively, known concentrations of GST-AβPP-(18-119) proteins were added to the wells followed by the anti-AβPP mAb 22C11 at a dilution of 1 µg/ml in PBS containing 0.1 mg/ml BSA and a secondary anti-mouse IgG conjugated to horseradish peroxidase (1:1000). Bound secondary antibody was detected using the colorimetric substrate as described above.

Site-Directed Mutagenesis of GST-AβPP-(18-119) Fusion Protein—

The pGEX-KG-human AβPP exon 2-3 fusion construct, encoding AβPP residues 18-119, was prepared. Individual amino acids from $Cys^{105}$ through $Cys^{117}$ within exon 3 were mutagenized to Ala employing single nucleotide change approach using the QuickChange Site-Directed Mutagenesis Kit (Stratagene, La Jolla, Calif.). Briefly, complementary oligonucleotides used in the site-directed mutagenesis were 5' phosphorylated, 40 bases in length with 20 matched bases on either side of the point mutation, possessing a $T_m \geq 78°$ C. and containing at least 40% GC content. The 50 μl PCR reaction sample included 40 ng of the pGEX-KG-human AβPP exon 2-3 fusion construct and 125 ng of the sense and antisense oligonucleotides. The PCR program was as follows: 1 cycle of 95° C. for 30 s, 20 cycles of 95° C. for 30 s, 55° C. for 1 min, 68° C. for 20 min, and 1 cycle of 72° C. for 10 min. The PCR product was then digested with DpnI for 1.5 hours to remove methylated parental DNA as per the manufacturer's protocol. The digested sample was transformed into Epicurian Coli XL1-Blue supercompetent cells and grown on LB agar plates containing 100 μg/ml ampicillin. Colonies were chosen and plasmid DNA was isolated and sequenced to confirm the presence of each mutation. In some cases, a second mutation was needed to change the codon to alanine. In these cases, sequential mutagenesis was done using two mutagenesis oligonucleotide sets, the second set with both mutations. The plasmids were sequenced to confirm the presence of the second mutation.

*Escherichia coli* BL21 cells were transformed with wild-type and mutant pGEXKG-human AβPP exon 2-3 fusion constructs, plated on LB agar plates containing 100 μg/ml ampicillin and incubated overnight at 37° C., and colonies were picked and used to inoculate 100 ml LB media. Protein expression was induced by the addition of isopropyl β-D-thioglucoside to a final concentration of 1 mM for 4 hours. Wild-type and mutant GST-AβPP-(18-119) fusion proteins were affinity-purified from the harvested cells using glutathione-Sepharose beads. The concentration of the eluted GST-AβPP-(18-119) fusion proteins was measured using the extinction coefficient of GST. The precise concentrations of wild-type and each mutant GST-AβPP-(18-119) protein were confirmed by titration using mAb 22C11 and compared with standard curves of known concentrations of purified sAβPPα. The mAb 22C11 was used for the precise titration since its epitope on AβPP and GST-AβPP-(18-119) resides upstream of residues 105-117 and was not affected by any of the alanine substitutions inserted in the mutant fusion proteins.

HCSM Cell Culture—

Primary cultures of HCSM cells were established and characterized. Two lines of HCSM cells were used in these studies. One was derived from a 70-year-old male AD patient and the other was derived from a 37-year-old female control. All HCSM cells were used between passages 4-7 and maintained in 24-well tissue culture dishes with Dulbecco's minimum essential medium containing 10% fetal bovine serum (Gemini Bio-Products, Calabasas, Calif.), non-essential amino acids, and antibiotics (Invitrogen). For experiments, near-confluent cultures of HCSM cells were placed in serum-free medium containing 0.1% BSA, non-essential amino acids, and antibiotics overnight prior to treatment. Freshly solubilized Dutch-type Aβ-(1-40) at a final concentration of 25 μM was added to the cultures in serum-free medium and incubated at 37° C. for 6 days. Cells were routinely viewed and photographed using an Olympus IX70 phase-contrast microscope. Cell viability was quantified using a fluorescent live/dead cell assay following the manufacturer's protocol (Molecular Probes, Eugene, Oreg.). The number of live and dead cells were counted from several fields (n=4) from at least three separate wells for each experiment.

Results:

Peptide Mapping of the Fibrillar A/3 Binding Domain in AβPP-(18-119)—

The amino-terminal region of AβPP-(18-119), encoded by exons 2 and 3 of the AβPP gene, was previously shown to mediate the binding of AβPP to fibrillar forms of Aβ. The goal of these experiments was to identify the precise site within this region of AβPP that is responsible for this interaction. To accomplish this, a series of overlapping peptides of amino acids starting at residue 18 of AβPP with each subsequent peptide shifting 3 amino acids toward the carboxyl-terminal end were synthesized. This approach covered the entire region of AβPP-(18-119). Each of these peptides was tested for its ability to compete against biotinylated sAβPPα for binding to fibrillar Aβ in a solid-phase binding assay. At a relatively high concentration of 1 mM, the peptide AβPP-(105-119) competed for ≈80% of the biotinylated sAβPPα binding to fibrillar. In contrast, a 1000-fold lower concentration of GST-AβPP-(18-119) completely blocked biotinylated sAβPPα binding to immobilized fibrillar Aβ. Overlapping peptide AβPP-(102-116) were also found to exhibit some competing activity in the assay, although it was approximately half that of AβPP-(105-119) (data not shown). However, none of the other 15-mer peptides showed either appreciable or consistent competing activity.

Previous results showed that fibrillar Aβ assembled on the surface of HCSM cells mediates the binding of endogenously produced sAβPPα on the cell surface. Consistent with the results obtained from the solid-phase binding assay, GST-AβPP-(18-119) completely inhibited endogenous sAβPPα binding to HCSM cell surface fibrillar Aβ, whereas higher concentrations of AβPP-(105-119) could partially diminish this A3PP binding. The findings that AβPP-(105-119) peptide was less effective than GST-AβPP-(18-119) and that higher concentrations of AβPP-(105-119) peptide were needed in blocking sAβPPα binding to fibrillar Aβ likely results from this region in AβPP being highly structured containing three intrachain disulfide bonds.

Alanine-Scanning Mutagenesis of the Putative Fibrillar 4 Binding Domain in AβPP-(18-119)—

The peptide-mapping experiments described above indicated that the sequence AβPP-(105-119) contains the fibrillar Aβ binding domain. However, this small peptide was not nearly as effective as the larger, recombinantly expressed AβPP-(18-119) in binding to fibrillar Aβ. Therefore, alanine-scanning mutagenesis studies of the AβPP-(105-119) sequence within AβPP-(18-119) were performed to further identify key epitopes important in facilitating its binding to fibrillar Aβ. Alanine residues were introduced from $Cys^{105}$ through $Cys^{117}$ of AβPP-(18-119) by site-directed mutagenesis of the AβPP-(18-119) cDNA. Each mutant AβPP-(18-119) cDNA was expressed as a GST fusion protein and purified, and the concentrations were carefully determined by quantitative immunoblotting as described in "Experimental Procedures". Each purified mutant GST-AβPP-(19-118) was tested for its ability to bind immobilized fibrillar Aβ in a solid-phase binding assay and compared with the level of binding observed with wildtype GST-AβPP-(18-119). Most of the alanine substitutions had modest inhibitory or enhancing effects on GST-AβPP-(18-119) binding to fibrillar Aβ.

However, alanine substitutions at residues $His^{110}$, $Val^{112}$, or $Ile^{113}$ showed highly diminished GST-AβPP-(18-119) binding to fibrillar Aβ. In particular, H110A mutant GST-AβPP-(18-119) exhibited <10% of fibrillar Aβ binding compared with wild-type GST-AβPP-(18-119). Based on a predicted structural fold of this region, it is interesting to note that the x-ray crystal structure for this amino-terminal region of AβPP reveals that residues $His^{110}$, $Val^{112}$, and $Ile^{113}$ all reside on the same β-strand of AβPP-(18-119). Also observed in these studies was that the C117A mutant GST-AβPP-(18-119) showed markedly diminished binding to fibrillar Aβ compared with wild-type GST-AβPP-(18-119). Residue $Cys^{117}$ participates in a disulfide bond with $Cy^{s73}$, suggesting that this linkage is important in presenting a properly folded fibrillar Aβ binding domain in AβPP-(18-119) likely involving a β-strand within this region that includes specific residues $His^{110}$, $Val^{112}$, and $Ile^{113}$.

H110A Mutant GST-A#PP-(18-119) is Deficient in Blocking Cell Death in Pathogenic Aβ-Treated Cultured HCSM Cells—

Incubation of HCSM cells with pathogenic Dutch-type Aβ-(1-40) leads to cell death. Previous results revealed that wild-type GST-AβPP-(18-119) inhibits HCSM cell death induced by treatment with Dutch-type Aβ-(1-40). Therefore, the H110A mutant GST-AβPP-(18-119), which is deficient in binding to fibrillar Aβ, was examined to determine whether it is capable of blocking HCSM cell death induced by treatment with Aβ-(1-40) Dutch-type. Near-confluent cultures of HCSM cells were incubated in the absence or presence of 25 μM Dutch-type Aβ-(1-40) and in the absence or presence of 1 μM wild-type or H110A mutant GSTAβPP-(18-119) for 6 days at 37° C. After this time, HCSM cell viability was quantified as described in "Experimental Methods." Wild-type GST-AβPP-(18-119) lowered Aβ-induced HCSM cell death to <10% (lane 4) whereas H110A mutant GST-AβPP-(18-119) was incapable of preventing the cytotoxic effects of this peptide. These studies demonstrate that H110A mutant GST-AβPP-(18-119) is ineffective in blocking cell death evoked by pathogenic Aβ in HCSM cells.

Deficient Binding of Mutant GST-AβPP-(18-119) Proteins to Fibrillar Amyloid Peptides—

The solid-phase binding experiments with wild-type and mutant GST-AβPP-(18-119) proteins were performed using fibrillar Dutch-type Aβ. Experiments were then performed to determine whether key mutant GST-AβPP-(18-119) proteins similarly exhibited deficient binding to fibrillar wild-type Aβ-(1-42) and fibrillar amylin peptide. These studies used purified wild-type, HUM mutant, and I113A mutant GST-AβPP-(18-119) proteins in solid-phase binding experiments. H110A and I113A mutant GST-AβPP-(18-119) proteins displayed markedly decreased binding to fibrillar Dutch-type Aβ-(1-40) compared with wild-type GST AβPP-(18-119). Similarly, both mutant GST-AβPP-(18-119) proteins showed considerably reduced binding to fibrillar wild-type Aβ-(1-42) and fibrillar amylin peptide compared with wild-type GST-AβPP-(18-119). As a control, none of the GST-AβPP-(18-119) proteins exhibited any binding to immobilized ovalbumin. These findings suggest that $His^{110}$ and $Ile^{113}$, which reside on the same β-strand within this region of AβPP, are key residues for also facilitating AβPP-(18-119) binding to fibrillar wild-type Aβ and fibrillar amylin peptides. The results with fibrillar amylin further suggest that the binding of AβPP-(18-119) through this domain is not sequence-specific but appears to involve recognition of the fibrillar structure of the peptide.

Discussion:

Deposition of fibrillar Aβ in senile plaques and in the walls of cerebral blood vessels is a key pathological feature of AD, Down's syndrome, and several related cerebral amyloid angiopathy disorders. These fibrillar Aβ deposits that occur within the brain are intimately associated with neuronal and cerebrovascular cell degeneration at their respective sites. Similarly, fibrillar Aβ deposition is involved in neuronal cell and HCSM cell toxicity in vitro. Fibrillar Aβ deposits that occur both in vivo and in vitro cell culture models lead to accumulation of its precursor protein AβPP. Fibrillar Aβ mediates the pathological accumulation of Al3PP on the HCSM cell surface through interaction with a domain in the cysteine-rich, amino-terminal region of AβPP. In this study the majority of the HCSM cell-accumulated AβPP was shown to be sAβPPα. Although sAβPPα has been postulated to be a protective molecule, the interaction between fibrillar Aβ and its precursor may have significant implications in cytopathogenic mechanisms in AD and related disorders. For example, this interaction, which results in the accumulation of AβPP on the HCSM cell surface, may contribute to the onset of cell death. Likewise, there is evidently an interaction between fibrillar APand AβPP in neuronal toxicity in vitro. In light of the potential importance of these findings, the precise site on AβPP that facilitates its binding to fibrillar Aβ was sought to be determined.

The amino-terminal domain of residues 18-119 was previously identified as the region on AβPP responsible for mediating its binding to fibrillar Aβ. Therefore, a set of overlapping 15-amino-acid peptides that spanned this region of AβPP were synthesized to further localize this site. In competition experiments, the peptide AβPP-(105-119), located at the extreme carboxyl-terminal end of this amino-terminal region of AβPP, was found to compete against AβPP for binding to both immobilized fibrillar Aβ and fibrillar Aβ assembled on the surface of HCSM cells. However, AβPP-(105-119) was found to be much less effective than GST-AβPP-(18-119) in its ability to compete for AβPP binding. This disparity is likely caused by the highly structured nature of AβPP-(18-119), a region that contains three intrachain disulfide bonds. Although the integrity of this structure is preserved in the recombinantly expressed GST-A[3PP-(18-119), it is unlikely to be properly folded in the small synthetic A[3PP-(105-119) peptide. Nevertheless, these findings suggest the involvement of this focused region on AβPP-(18-119) in binding fibrillar Aβ.

Because the peptide-competition experiments implicated the region AβPP-(105-119) as the likely site of a fibrillar Aβ binding domain, alanine-scanning mutagenesis studies were conducted in this region to determine the key residues involved. This analysis was performed using recombinantly expressed GST-AβPP-(18-119) fusion proteins since the wild-type GST-AβPP-(18-119) protein faithfully recapitulates the binding characteristics of native sAβPP to fibrillar Aβ. Alanine substitutions were made for each amino acid from $Cys^{105}$ through $Cys^{117}$ of GST-AβPP-(18-119). These studies clearly identified His110, $Val^{112}$, and $Ile^{113}$ as key residues that facilitate GST-AβPP-(18-119) binding to fibrillar Aβ. It is noteworthy that these three particular residues reside on a predicted common β-strand within this region of AβPP. These particular residues, along with $Phe^{37}$, $Pro^{109}$, $Phe^{111}$, and $Tyr^{115}$ may form a hydrophobic surface patch on AβPP. These alanine scanning mutagenesis results indicate that P109A, F111A, and Y115A had little or no effect on GST-AβPP-(18-119) binding to fibrillar Aβ. Similarly, little effect on binding was observed with a F37A mutant GST-AβPP-(18-119. This suggests that this putative hydrophobic surface patch is not wholly involved with mediating the binding of AβPP to fibrillar Aβ. The finding that the C117A substitution substantially affects GST-AβPP-(18-119) binding to fibrillar Aβ further supports the notion that the disulfide bond formed between $Cys^{73}$ and $Cys^{117}$ is important for properly presenting the β-strand of this region containing $His^{110}$, $Val^{112}$, and $Ile^{113}$ as a functional fibrillar Aβ binding domain.

Treatment of cultured HCSM cells with pathogenic forms of Aβ results in a protracted period of cellular degeneration leading to apoptotic cell death. Previous results demonstrated that GST-AβPP-(18-119), which contains a functionally active fibrillar binding domain, blocks cell death in HCSM cells treated with pathogenic Dutch-type Aβ-(1-40). GST-AβPP-(18-119) may act as a dominant-negative factor containing the site for fibrillar Aβ binding but lacks other downstream regions of AβPP that mediate a cell-death response. This study demonstrates that in contrast to wild-type GST-AβPP-(18-119), the H110A mutant GST-AβPP-(18-119), which is deficient in fibrillar AE3 binding, is incapable of protecting HCSM cells from the cytotoxic effects of Dutch-type Aβ-(1-40). This finding further supports the notion that an interaction between AβPP and fibrillar contributes to the cell death response in HCSM cells.

Earlier studies showed that biotinylated sAβPPa and GST-AβPP-(18-119) bound to fibrils formed with either Dutch-type A13-(1-40) or wild-type Aβ-(1-42), but not unassembled forms, indicating that this interaction depends on fibrillar structures of the peptide. Similarly, the present study shows that H110A mutant and I113A mutant GSTAβPP-(18-119) proteins are deficient in binding fibrils formed with either Dutch-type Aβ-(1-40) or wild-type Aβ-(1-42). It is noteworthy that the same pattern of binding was observed when fibrillar amylin peptide was used in the solid-phase binding assay. This finding suggests that the β-strand containing residues $His^{110}$, $Val^{112}$, and $Ile^{113}$ folds into a binding site that is not specific for the Aβ amino acid sequence but rather possesses recognition for fibrillar structures. Therefore, it is possible that this domain may mediate the binding of AβPP to other fibrillar structures as well.

The binding of fibrillar Aβ, and possibly other fibrillar proteins, to AβPP through the domain identified here may have several potential consequences. For example, this interaction may help to explain the high levels of AβPP that accumulate around fibrillar Aβ present in cerebrovascular and, possibly plaque, amyloid deposits. In addition, recent results showed that the binding of fibrillar Aβ to KPI-containing forms of AβPP enhances its coagulation proteinase inhibitory properties. The KPI domain resides downstream from AβPP-(105-119) starting at AβPP residue 289. This finding suggests that fibrillar Aβ deposits may bind, localize, and stimulate the proteinase inhibitory functions of AβPP. This activity may have implications regarding hemorrhagic stroke seen in patients with severe cerebral amyloid angiopathy. AβPP that is produced locally in the cerebral vessel wall or released by circulating activated platelets may accumulate at sites of cerebrovascular Aβ deposition. This would result in a microenvironment high in anticoagulant activity and conducive to hemorrhaging.

More germane to the present work, several studies have reported that treatment of cultured neuronal cells with the mAb 22C11 or a polyclonal antibody (both of which recognize epitopes in the amino-terminal region of AβPP not far from the identified fibrillar Aβ binding site) can stimulate G-protein activity and/or initiate cell death pathways in vitro. It is thought that these responses proceed through the dimerization of AβPP by divalent antibody binding. Also of note is accumulating evidence from in vitro studies with antibodies that AβPP dimerization contributes to increased Aβ production. Other more pathologically relevant agonists than antibodies must exist in vivo to elicit these potential responses in situations such as AD. In this case the Aβ fibril, and perhaps the protofibril, may be pathological agonists that facilitate AβPP dimerization on the cell surface stimulating cell death pathways and Aβ production. In regard to the present study, GST-AβPP-(18-119) may inhibit pathogenic Aβ-induced HCSM cell death by interfering with AβPP dimerization. This is also consistent with finding that GST-AβPP-(18-119) mutants deficient in binding fibrillar Aβ are incapable of blocking pathogenic Aβ-induced HCSM cell death.

In summary, the present study has identified the precise site of a fibrillar binding domain on the extracellular, amino-terminal region of AβPP. This site involves several key amino acids located on a putative β-strand within this region and depends on proper disulfide bonding. The interaction of AβPP with fibrillar Aβ mediated through this site may contribute to the pathologic accumulation of AβPP observed at sites of fibrillar Aβ deposition that occur in vitro on the cultured HCSM cell surface and in vivo in the cerebral vessel walls of patients with severe cerebral amyloid angiopathy. This pathologic fibrillar Aβ-AβPP interaction may provide further insight into the mechanisms that lead to cerebrovascular and, possibly neuronal, cellular degeneration observed in AD and related disorders.

Example 2

MBP Inhibits CAA Mutant A Fibrillogenesis

Deposition of fibrillar Aβ in brain is a prominent pathological feature of AD and related disorders, including familial forms of CAA. Mutant forms of Aβ including Dutch-type and Iowa-type Aβ, which are responsible for familial CAA, deposit primarily as fibrillar amyloid along the cerebral vasculature and are either absent or present only as diffuse non-fibrillar plaques in the brain parenchyma. Despite the lack of parenchymal fibril formation in vivo, these CAA mutant Aβ peptides exhibit a markedly increased rate and extent of fibril formation in vitro compared to wild-type Aβ. Based on these conflicting observations the Applicant sought to determine if brain parenchymal factors exist that selectively interact with and modulate CAA mutant Aβ fibril assembly. A combination of immunoaffinity chromatography coupled with mass spectrometry has shown that MBP was identified as a prominent brain parenchymal factor that preferentially binds to CAA mutant Aβ compared to wild-type Aβ. Surface plasmon resonance measurements confirmed that MBP bound more tightly to Dutch/Iowa CAA mutant Aβ than wild-type Aβ. Using a combination of biochemical and ultrastructural techniques, MBP was found to inhibit the fibril assembly of CAA mutant Aβ. This was confirmed by TEM and single-touch AFM analysis as shown in FIG. 1. At 6 hours of incubation, in the absence of MBP, Dutch/Iowa Aβ40 formed dense networks of fibrils as observed by TEM (FIG. 1A). In the presence of sub-stoichiometric amounts of MBP, no evidence of fibril formation was found and only amorphous aggregate staining was observed (FIG. 1B). At an earlier time point of 3 hours, high resolution single-touch AFM showed that Dutch/Iowa Aβ40 forms long, well-ordered fibrils with heights of ≈4 nm and variable lengths (FIG. 1D). In the presence of MBP at 3 hours, Aβ40DI peptides form shorter, less-ordered oligomers and protofibrils with heights of ≈2 nm and lengths<200 nm (FIG. 1E). TEM and AFM images of MBP alone show that MBP does not aggregate significantly in these assays (FIG.

1C, 1F, respectively). Together, these findings suggest a possible role for MBP in regulating parenchymal fibrillar Aβ deposition.

Example 3

MBP Inhibits Wild-Type Aβ42 Fibrillogenesis

Figure 2:
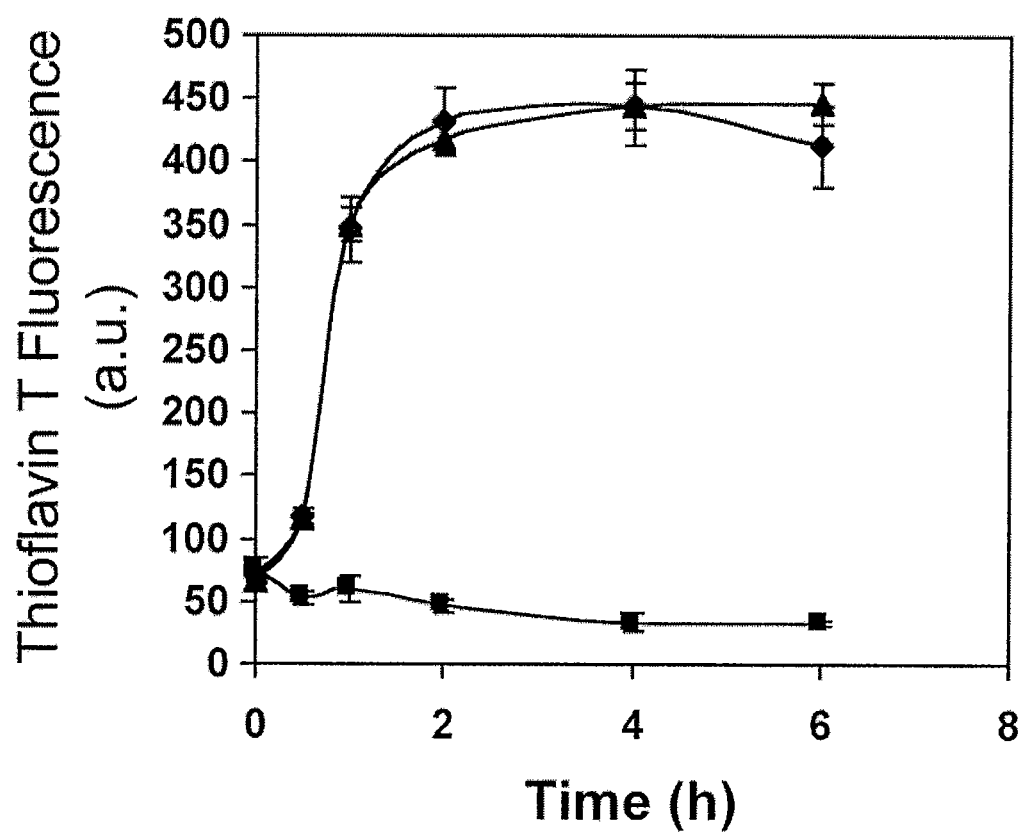
FIG. 2 depicts the results of a thioflavin T analysis of inhibition of wild-type Aβ42 fibrillization by MBP (squares) and bovine lactalbumin as control (diamonds). Mean±S.D. of triplicate samples are shown.

The findings described above showed that MBP bound CAA mutant Aβ40 and inhibited its fibrillogenesis. Significantly weaker binding to wild-type Aβ40 was observed. However, due to the poor fibrillogenic properties of wild-type Aβ40 it was difficult to ascertain if MBP can inhibit this process with this peptide. Therefore, the binding of MBP to wild-type Aβ42 was determined by surface plasmon resonance. MBP bound to Dutch/Iowa CAA mutant Aβ40 with a KD=1.69×10$^{-8}$M. MBP bound to wild-type Aβ42 with a similar KD 4.30×10$^{-8}$M. Subsequently, as shown in FIG. 2, purified MBP inhibited wild-type Aβ42 fibrillogenesis according to a thioflavin T fluorescence assay. This is a significant finding since it shows that the binding and fibril inhibiting effects of MBP are not restricted to CAA mutant Aβ but are more general and may reflect an activity on Aβ peptides that exhibit a high propensity to form fibrils (i.e. CAA mutant forms or wild-type Aβ42).

Example 4

Mapping of the Aβ Binding Domain on MBP

Figure 4B:
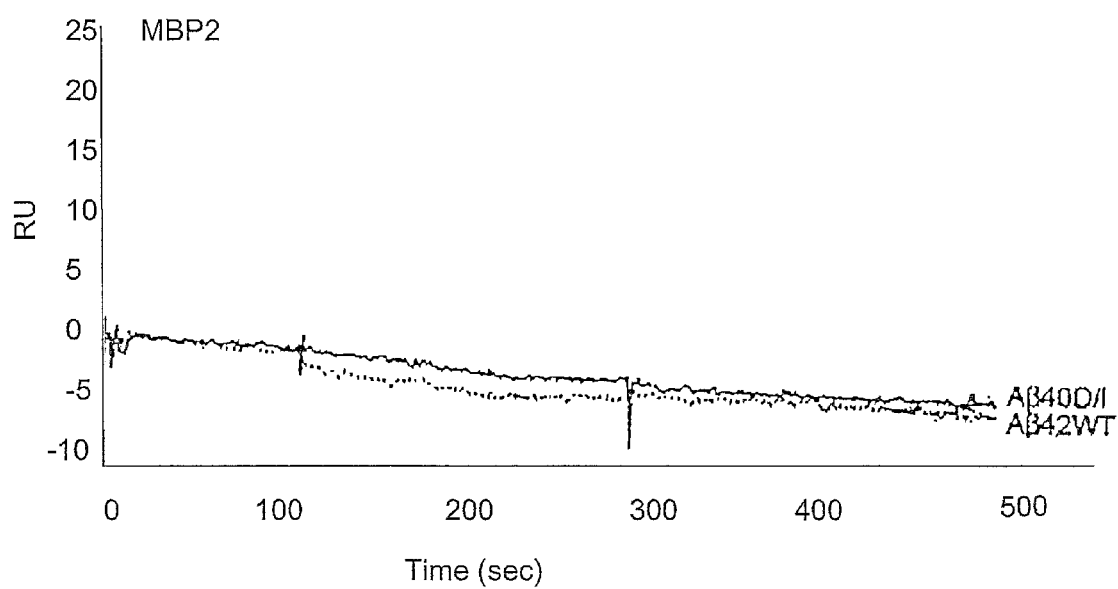
Figure 4C:
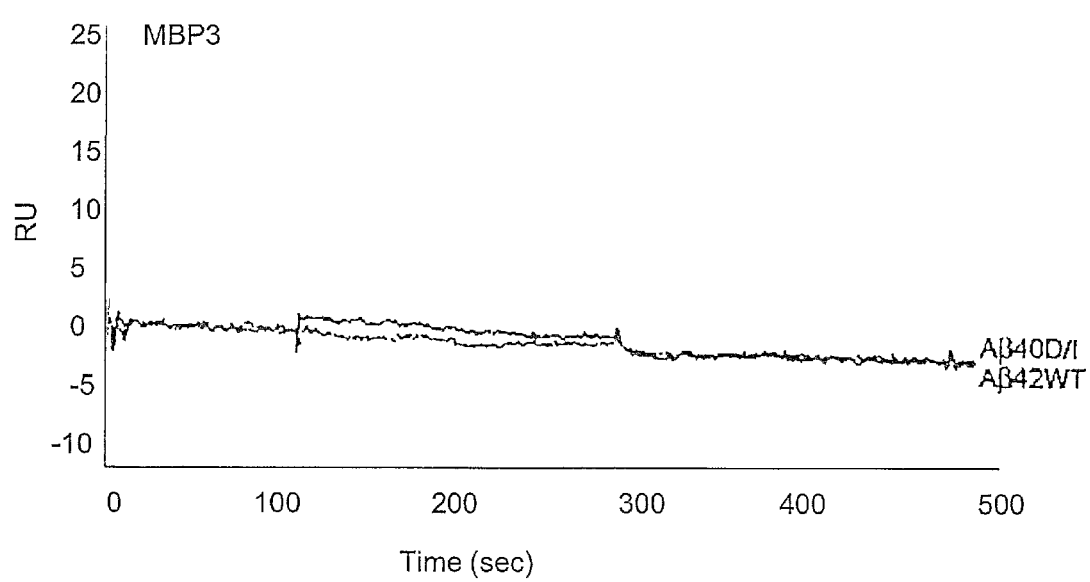
Figure 4D:
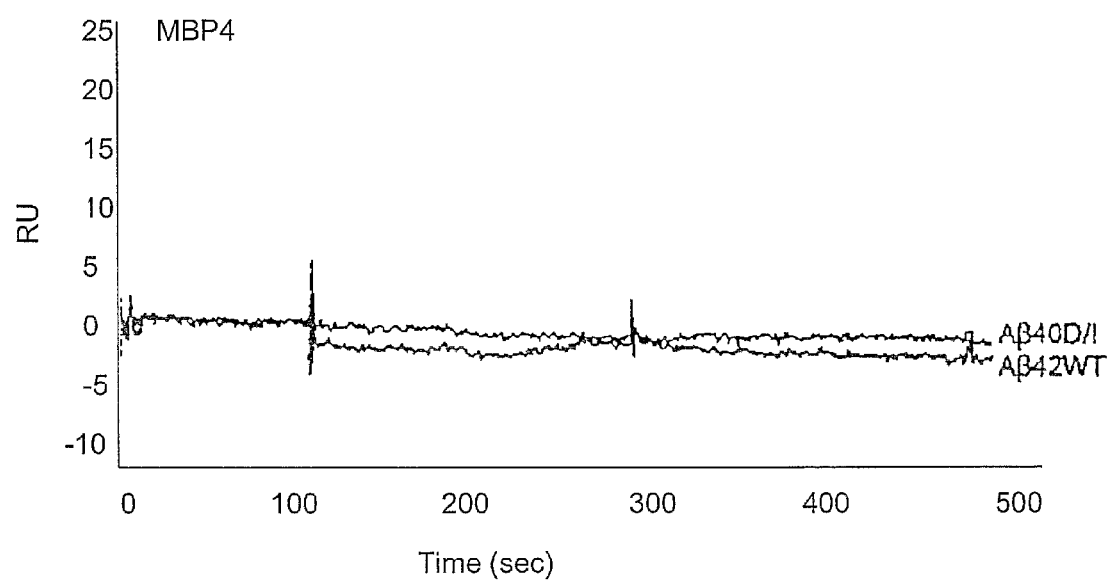

Using recombinant methodology to express and purify regions of the 18.5 kDa human MBP protein and test their abilities to bind Aβ and inhibit fibrillogenesis, cDNAs were prepared for the following regions of MBP shown in FIG. 3. The cDNAs for MBP fragments were cloned into pTYB11 plasmids containing an ampr gene and transformed into competent E. coli BL21 DE3 cells. Expression of cDNAs in this vector results in a fusion protein containing a chitin binding domain (CBD) as well as a self-cleavable intein protein from S. cerevisiae. CBD-Intein-MBP fusion proteins were captured on chitin beads from the resulting cell lysates. MBP protein fragments were eluted by inducing the cleavage between the C-terminus of the intein and the N-terminus of MBP by exposure to dithiothreitol. This resulted in MBP and fragments free of any affinity tags or additional residues. MBP was further purified by cation exchange chromatography on CM52 resin, resulting in a >95% pure protein preparations. Each of the four MBP fragments were tested for binding to Dutch/Iowa Aβ40 and wild-type Aβ42 by surface plasmon resonance (FIG. 4).

Figure 5:
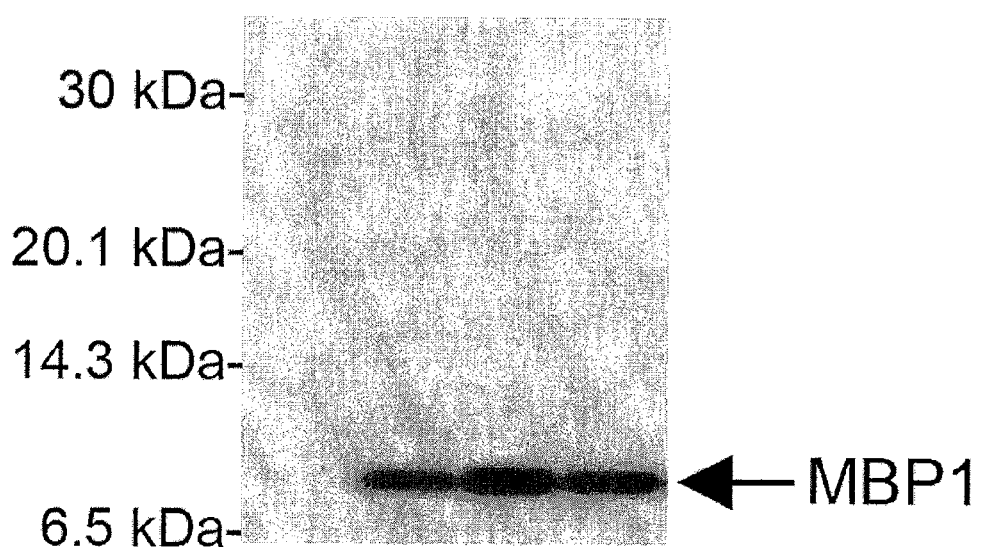
FIG. 5 (Panel B, FIG. 4.1?) is an SDS-PAGE gel analysis of the purification of MBP1 (Coomassie Brilliant Blue Stain)
Figure 6:
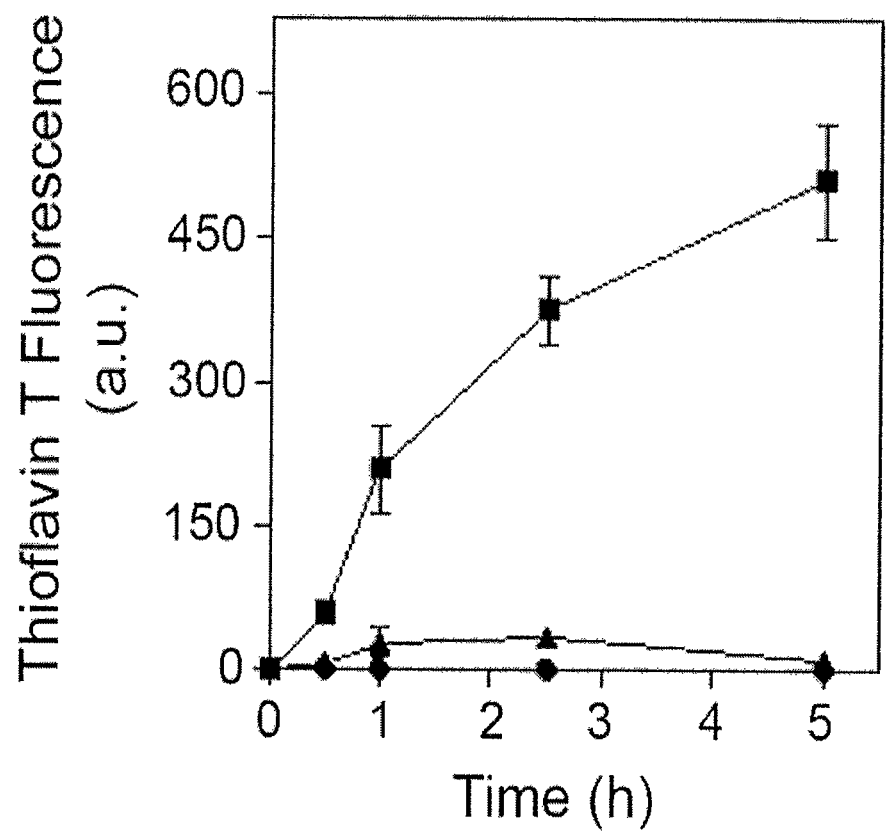
FIG. 6 compares the inhibitory effect of MBP and MBP1 on fibrillization of Dutch/Iowa mutant Aβ40. Squares represent no inhibitor present, triangles represent inhibitor present. Mean±S.D. of triplicate samples are shown.
Figure 7:
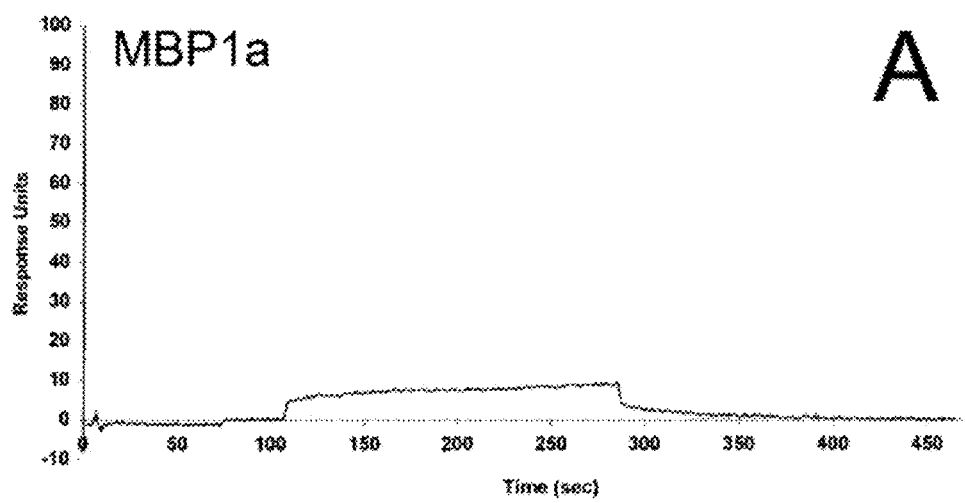
FIG. 7 illustrates the binding of MBP1a (FIG. 7A) and MBP1b (FIG. 7B) to Dutch/Iowa Aβ40 by surface plasmon resonance.
Figure 7:
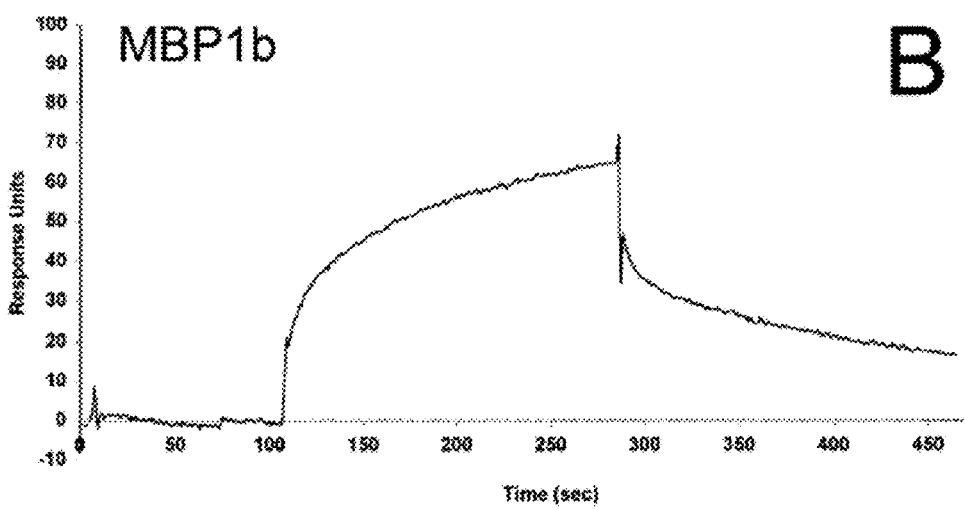

Only fragment MBP1, composed of residues 1-63 of MBP, showed binding to the Aβ peptides. Further, the tenacity of the binding to Aβ peptides was very similar to that observed for intact MBP. It is of note that MBP1 is encoded from MBP exon 1 of the Golli/MBP locus and contained in both Golli and MBP proteins. An example of purified recombinant MBP1 is shown in FIG. 5. Fragment MBP1 inhibits Dutch/Iowa CAA mutant Aβ fibrillogenesis as assessed by thioflavin T binding (FIG. 6). Thus, the Aβ binding region of MBP is in residues 1-64 (MBP1). Each of two fragments of MBP1, MBP1a spanning MBP1-32 (MASQKRPSQRHGSKYLATASTMDHARHGFLRP) (SEQ ID NO:13) and MBP1b spanning MBP 33-64 (HRDTGILDSIGRFFGGDRGAPKRGSGKDSHHP) (SEQ ID NO:14), was expressed as fusion proteins containing a chitin binding domain (CBD) as well as a self-cleavable intein protein from S. cerevisiae. CBD-Intein-MBP fusion proteins were captured on chitin beads from the resulting cell lysates. MBP1a and MBP1b protein fragments were eluted by inducing the cleavage between the C-terminus of the intein and the N-terminus of MBP by exposure to dithiothreitol. The MBP fragments were further purified by cation exchange chromatography on CM52 resin, resulting in a >95% pure protein preparations. The purified MBP1a and MBP1b fragments were tested for binding to Dutch/Iowa Aβ40 by surface plasmon resonance (SPR) as shown below in FIG. 7. Fragment MBP1a (FIG. 7A) showed no binding to Dutch/Iowa Aβ40 on SPR whereas MBP1b (FIG. 7B) exhibited strong binding. Moreover, MBP1b, but not MBP1a, inhibited Aβ fibril assembly as assessed by the thioflavin-T binding fluorescence assay (not shown).

Example 5

Identification of the KRGX1X2X3X4X5X6HP Motif (SEQ ID NO: 1)

The discovery that the amyloid β-protein precursor (AβPP), in a region within residues 18-119, binds strongly with fibrillar amyloid proteins, taken together with the more recent discovery that MBP also binds such proteins, suggested that a search be made for a similar motif in both this region of AβPP and MBP. Such a motif, KRGX$_1$X$_2$X$_3$X$_4$X$_5$X$_6$HP (SEQ ID NO:1), was found in MBP 33-64 and in AβPP 54-64. Specifically, the motif in MBP spans residues 54-64. Using recombinant methodology to express and purify regions of the human MBP protein and test their abilities to bind Aβ and inhibit fibrillogenesis, as above, MBP 1-49 was tested with negative results. The fragment remaining (MBP 50-64) carries all the binding activity. In one embodiment, the invention provides a peptide composition comprising the amino acid sequence KRGX$_1$X$_2$X$_3$X$_4$X$_5$X$_6$HP, wherein X$_1$-X$_6$ are amino acids selected from the group consisting of G, P, A, V, L, I, M, C, F, Y, W, H, K, R, Q, N, E, D, S and T (SEQ ID NO:1). In one embodiment, the peptide composition is selected from the group consisting of KRGSGKDSHHP (SEQ ID NO:2), KRGRKQCKTHP (SEQ ID NO:3) and KRGSGKVPWLK (SEQ ID NO:4).

The invention claimed is:

1. A method of treating a subject having an amyloid disease or disorder, wherein said subject comprises at least one fibril, comprising administering a composition comprising a peptide consisting of a myelin basic protein fragment, wherein said fragment consists of the amino acid sequence KRGX$_1$X$_2$X$_3$X$_4$X$_5$X$_6$HP (SEQ ID NO: 1), wherein X$_1$-X$_6$ are amino acids selected from the group consisting of G, P, A, V, L, I, M, C, F, Y, W, H, K, R, Q, N, E, D, S and T, wherein said amyloid disease or disorder is ameliorated.

2. The method of claim 1, wherein said composition further comprises a pharmaceutically acceptable vehicle, wherein said vehicle is targeted to said at least one fibril.

3. The method of claim 1, wherein said administering contacts said composition with a brain tissue of said subject.

4. The method of claim 1, wherein said myelin basic protein fragment is KRGSGKVPWLK (SEQ ID NO:4).

5. The method of claim 1, wherein said amyloid disease or disorder is selected from the group consisting of Alzheimer's disease, cerebral amyloid angiopathy, bovine spongiform encephalopathy, Creutzfeldt-Jakob disease, laughing death syndrome, scrapie, and Lewy body dementia.

6. The method of claim 1, wherein said at least one fibril comprises at least one fibrillizing peptide.

7. The method of claim 6, wherein said at least one fibrillizing peptide is an Aβ peptide.

8. The method of claim 6, wherein said myelin basic protein fragment interferes with said at least one fibrillizing peptide such that formation of a plaque is inhibited.

9. A method of treating a subject having an amyloid disease or disorder, wherein said subject comprises at least one fibril comprising administering a composition comprising a vector encoding a peptide consisting of a myelin basic protein fragment, wherein said fragment consists of the amino acid sequence KRGX$_1$X$_2$X$_3$X$_4$X$_5$X$_6$HP (SEQ ID NO: 1), wherein X$_1$-X$_6$ are amino acids selected from the group consisting of G, P, A, V, L, I, M, C, F, Y, W, H, K, R, Q, N, E, D, S and T, wherein said amyloid disease or disorder is ameliorated.

10. The method of claim 9, wherein said composition further comprises a pharmaceutically acceptable vehicle, wherein said vehicle is targeted to said at least one fibril.

11. The method of claim 10, wherein said pharmaceutically acceptable vehicle comprises a nanoparticle vehicle.

12. The method of claim 10, wherein said pharmaceutically acceptable vehicle comprises a vector-based delivery vehicle.

13. The method of claim 9, wherein said administering contacts said composition with a brain tissue of said subject.

14. The method of claim 9, wherein said myelin basic protein fragment is KRGSGKVPWLK (SEQ ID NO:4).

15. The method of claim 9, wherein said amyloid disease or disorder is selected from the group consisting of Alzheimer's disease, cerebral amyloid angiopathy, bovine spongiform encephalopathy, Creutzfeldt-Jakob disease, laughing death syndrome, scrapie, and Lewy body dementia.

16. The method of claim 9, wherein said fibril comprises at least one fibrillizing peptide.

17. The method of claim 9, wherein said at least one fibrillizing peptide is an Aβ peptide.

18. The method of claim 9, wherein said myelin basic protein fragment interferes with said at least one fibrillizing peptide such that formation of a plaque is inhibited.

* * * * *

SEQUENCE LISTING

```
<160> NUMBER OF SEQ ID NOS: 52

<210> SEQ ID NO 1
<211> LENGTH: 11
<212> TYPE: PRT
<213> ORGANISM: Artificial sequence
<220> FEATURE:
<223> OTHER INFORMATION: Synthetic
<220> FEATURE:
```

-continued

```
<221> NAME/KEY: MISC_FEATURE
<222> LOCATION: (4)..(9)
<223> OTHER INFORMATION: The residues in these positions are amino acids
      selected from the group consisting of G, P, A, V, L, I, M, C, F,
      Y, W, H, K, R, Q, N, E, D, S and T.

<400> SEQUENCE: 1

Lys Arg Gly Xaa Xaa Xaa Xaa Xaa Xaa His Pro
1               5                   10

<210> SEQ ID NO 2
<211> LENGTH: 11
<212> TYPE: PRT
<213> ORGANISM: Artificial sequence
<220> FEATURE:
<223> OTHER INFORMATION: Synthetic

<400> SEQUENCE: 2

Lys Arg Gly Ser Gly Lys Asp Ser His His Pro
1               5                   10

<210> SEQ ID NO 3
<211> LENGTH: 11
<212> TYPE: PRT
<213> ORGANISM: Artificial sequence
<220> FEATURE:
<223> OTHER INFORMATION: Synthetic

<400> SEQUENCE: 3

Lys Arg Gly Arg Lys Gln Cys Lys Thr His Pro
1               5                   10

<210> SEQ ID NO 4
<211> LENGTH: 11
<212> TYPE: PRT
<213> ORGANISM: Artificial sequence
<220> FEATURE:
<223> OTHER INFORMATION: Synthetic

<400> SEQUENCE: 4

Lys Arg Gly Ser Gly Lys Val Pro Trp Leu Lys
1               5                   10

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000
```

```
<210> SEQ ID NO 9
<400> SEQUENCE: 9

000

<210> SEQ ID NO 10
<400> SEQUENCE: 10

000

<210> SEQ ID NO 11
<400> SEQUENCE: 11

000

<210> SEQ ID NO 12
<400> SEQUENCE: 12

000

<210> SEQ ID NO 13
<211> LENGTH: 32
<212> TYPE: PRT
<213> ORGANISM: Artificial sequence
<220> FEATURE:
<223> OTHER INFORMATION: Synthetic

<400> SEQUENCE: 13

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Arg Pro
            20                  25                  30

<210> SEQ ID NO 14
<211> LENGTH: 32
<212> TYPE: PRT
<213> ORGANISM: Artificial sequence
<220> FEATURE:
<223> OTHER INFORMATION: Synthetic

<400> SEQUENCE: 14

His Arg Asp Thr Gly Ile Leu Asp Ser Ile Gly Arg Phe Phe Gly Gly
1               5                   10                  15

Asp Arg Gly Ala Pro Lys Arg Gly Ser Gly Lys Asp Ser His His Pro
            20                  25                  30

<210> SEQ ID NO 15
<400> SEQUENCE: 15

000

<210> SEQ ID NO 16
<400> SEQUENCE: 16

000

<210> SEQ ID NO 17
<400> SEQUENCE: 17

000
```

<210> SEQ ID NO 18

<400> SEQUENCE: 18

000

<210> SEQ ID NO 19

<400> SEQUENCE: 19

000

<210> SEQ ID NO 20
<211> LENGTH: 11
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (4)..(11)
<223> OTHER INFORMATION: Xaa can be any naturally occurring amino acid

<400> SEQUENCE: 20

Lys Arg Gly Xaa Xaa Xaa Xaa Xaa Xaa Xaa Xaa
1               5                   10

<210> SEQ ID NO 21
<211> LENGTH: 11
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: Xaa can be any naturally occurring amino acid

<400> SEQUENCE: 21

Lys Arg Gly Ser Gly Lys Val Trp Pro Xaa Xaa
1               5                   10

<210> SEQ ID NO 22
<211> LENGTH: 11
<212> TYPE: PRT
<213> ORGANISM: Artificial sequence
<220> FEATURE:
<223> OTHER INFORMATION: Artificial sequence Synthetic
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 22

Lys Arg Gly Ser Gly Lys Asp Xaa His Xaa Xaa
1               5                   10

<210> SEQ ID NO 23
<211> LENGTH: 11
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (4)..(9)
<223> OTHER INFORMATION: Xaa can be any naturally occurring amino acid

<400> SEQUENCE: 23

Lys Arg Gly Xaa Xaa Xaa Xaa Xaa Xaa Leu Lys
1               5                   10

<210> SEQ ID NO 24
<211> LENGTH: 11
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (4)..(9)
<223> OTHER INFORMATION: Xaa can be any naturally occurring amino acid

<400> SEQUENCE: 24

Lys Arg Gly Xaa Xaa Xaa Xaa Xaa Xaa Thr Arg
1               5                   10

<210> SEQ ID NO 25
<211> LENGTH: 11
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (4)..(9)
<223> OTHER INFORMATION: Xaa can be any naturally occurring amino acid

<400> SEQUENCE: 25

Lys Arg Gly Xaa Xaa Xaa Xaa Xaa Xaa His Ala
1               5                   10

<210> SEQ ID NO 26

<400> SEQUENCE: 26

000

<210> SEQ ID NO 27
<211> LENGTH: 11
<212> TYPE: PRT
<213> ORGANISM: Artificial sequence
<220> FEATURE:
<223> OTHER INFORMATION: Synthetic

<400> SEQUENCE: 27

Lys Arg Gly Arg Lys Gln Cys Lys Thr His Pro
1               5                   10

<210> SEQ ID NO 28
<211> LENGTH: 11
<212> TYPE: PRT
<213> ORGANISM: Artificial sequence
<220> FEATURE:
<223> OTHER INFORMATION: Synthetic

<400> SEQUENCE: 28

Lys Arg Gly Ser Gly Lys Val Pro Trp Leu Lys
1               5                   10

<210> SEQ ID NO 29
<211> LENGTH: 11
<212> TYPE: PRT

```
<213> ORGANISM: Artificial sequence
<220> FEATURE:
<223> OTHER INFORMATION: Synthetic

<400> SEQUENCE: 29

Lys Arg Gly Ser Gly Lys Val Pro Trp Leu Lys
1               5                   10

<210> SEQ ID NO 30
<211> LENGTH: 11
<212> TYPE: PRT
<213> ORGANISM: Artificial sequence
<220> FEATURE:
<223> OTHER INFORMATION: Synthetic

<400> SEQUENCE: 30

Lys Arg Gly Ser Gly Lys Val Pro Trp Leu Lys
1               5                   10

<210> SEQ ID NO 31
<211> LENGTH: 11
<212> TYPE: PRT
<213> ORGANISM: Artificial sequence
<220> FEATURE:
<223> OTHER INFORMATION: Synthetic

<400> SEQUENCE: 31

Lys Arg Gly Ser Gly Lys Asp Ser His Thr Arg
1               5                   10

<210> SEQ ID NO 32
<211> LENGTH: 11
<212> TYPE: PRT
<213> ORGANISM: Artificial sequence
<220> FEATURE:
<223> OTHER INFORMATION: Synthetic

<400> SEQUENCE: 32

Lys Arg Gly Ser Gly Lys Asp Gly His His Ala
1               5                   10

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37
```

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 2300
<212> TYPE: DNA
<213> ORGANISM: Homo sapiens

<400> SEQUENCE: 41

| | | | | | |
|---|---|---|---|---|---|
| ggacaacacc | ttcaaagaca | ggccctctga | gtccgacgag | ctccagacca | tccaagaaga | 60 |
| cagtgcagcc | acctccgaga | gcctggatgt | gatggcgtca | cagaagagac | cctcccagag | 120 |
| gcacggatcc | aagtacctgg | ccacagcaag | taccatggac | catgccaggc | atggcttcct | 180 |
| cccaaggcac | agagacacgg | gcatccttga | ctccatcggg | cgcttctttg | gcggtgacag | 240 |
| gggtgcgccc | aagcggggct | ctggcaaggt | accctggcta | agccgggcc | ggagccctct | 300 |
| gccctctcat | gcccgcagcc | agcctgggct | gtgcaacatg | tacaaggact | cacaccaccc | 360 |
| ggcaagaact | gctcactacg | gctccctgcc | ccagaagtca | cacggccgga | cccaagatga | 420 |
| aaacccgta | gtccacttct | tcaagaacat | tgtgacgcct | cgcacaccac | cccgtcgca | 480 |
| gggaaagggg | agaggactgt | ccctgagcag | atttagctgg | ggggccgaag | gccagagacc | 540 |
| aggatttggc | tacggaggca | gagcgtccga | ctataaatcg | gctcacaagg | gattcaaggg | 600 |
| agtcgatgcc | cagggcacgc | tttccaaaat | ttttaagctg | ggaggaagag | atagtcgctc | 660 |
| tggatcaccc | atggctagac | gctgaaaacc | cacctggttc | cggaatcctg | tcctcagctt | 720 |
| cttaatataa | ctgccttaaa | actttaatcc | cacttgcccc | tgttacctaa | ttagagcaga | 780 |
| tgacccctcc | cctaatgcct | gcggagttgt | gcacgtagta | gggtcaggcc | acggcagcct | 840 |
| accggcaatt | tccggccaac | agttaaatga | aacatgaaa | acagaaaacg | gttaaaactg | 900 |
| tcccttcctg | tgtgaagatc | acgttccttc | ccccgcaatg | tgcccccaga | cgcacgtggg | 960 |
| tcttcagggg | gccaggtgca | cagacgtccc | tccacgttca | cccctccacc | cttggacttt | 1020 |
| cttttcgccg | tggctgcggc | acccttgcgc | ttttgctggt | cactgccatg | gaggcacaca | 1080 |
| gctgcagaga | cagagaggac | gtgggcggca | gagaggactg | ttgacatcca | agcttccttt | 1140 |
| gttttttttt | cctgtccttc | tctcacctcc | taaagtagac | ttcattttc | ctaacaggat | 1200 |
| tagacagtca | aggagtggct | tactacatgt | gggagctttt | ggtatgtgac | atgcgggctg | 1260 |
| ggcagctgtt | agagtccaac | gtggggcagc | acagagaggg | ggccacctcc | ccaggccgtg | 1320 |
| gctgcccaca | caccccaatt | agctgaattc | gcgtgtggca | gagggaggaa | aaggaggcaa | 1380 |

```
acgtgggctg ggcaatggcc tcacatagga acagggtct tcctggagat ttggtgatgg    1440
agatgtcaag caggtggcct ctggacgtca ccgttgccct gcatggtggc cccagagcag    1500
cctctatgaa caacctcgtt tccaaaccac agcccacagc cggagagtcc aggaagactt    1560
gcgcactcag agcagaaggg taggagtcct ctagacagcc tcgcagccgc gccagtcgcc    1620
catagacact ggctgtgacc gggcgtgctg gcagcggcag tgcacagtgg ccagcactaa    1680
ccctccctga aagataaacc ggctcattca cttcctccca aagacgcgt ggtagcgagt    1740 aggcacaggc gtgcacctgc tcccgaatta ctcaccgaga cacacgggct gagcagacgg    1800
ccccgtggat ggagacaaag agctcttctg accatatcct tcttaacacc cgctggcatc    1860
tcctttcgcg cctccctccc taacctactg acccacctt tgatttttagc gcacctgtga    1920 ttgataggcc ttccaaagag tcccacgctg gcatcaccct ccccgaggac ggagatgagg    1980
agtagtcagc gtgatgccaa aacgcgtctt cttaatccaa ttctaattct gaatgtttcg    2040
tgtgggctta ataccatgtc tattaatata tagcctcgat gatgagagag ttacaaagaa    2100
caaaactcca gacacaaacc tccaaatttt tcagcagaag cactctgcgt cgctgagctg    2160
aggtcggctc tgcgatccat acgtggccgc acccacacag cacgtgctgt gacgatggct    2220
gaacggaaag tgtacactgt tcctgaatat tgaaataaaa caataaactt ttaatggtaa    2280
aaaaaaaaaa aaaaaaaaa                                                  2300
```

<210> SEQ ID NO 42
<211> LENGTH: 2267
<212> TYPE: DNA
<213> ORGANISM: Homo sapiens

<400> SEQUENCE: 42

```
ggacaacacc ttcaaagaca ggccctctga gtccgacgag ctccagacca tccaagaaga    60
cagtgcagcc acctccgaga gcctggatgt gatggcgtca cagaagagac cctcccagag    120
gcacggatcc aagtacctgg ccacagcaag taccatggac catgccaggc atggcttcct    180
cccaaggcac agagacacgg gcatccttga ctccatcggg cgcttctttg gcggtgacag    240
gggtgcgccc aagcggggct ctggcaaggt accctggcta aagccgggcc ggagccctct    300
gccctctcat gcccgcagcc agcctgggct gtgcaacatg tacaaggact cacaccaccc    360
ggcaagaact gctcactacg gctccctgcc ccagaagtca cacggccgga cccaagatga    420
aaaccccgta gtccacttct tcaagaacat tgtgacgcct cgcacaccac cccgtcgca    480 gggaaagggg gccgaaggcc agagaccagg atttggctac ggaggcagag cgtccgacta    540
taaatcggct cacaagggat tcaagggagt cgatgcccag ggcacgcttt ccaaaatttt    600
taagctggga ggaagagata gtcgctctgg atcacccatg gctagacgct gaaaacccac    660
ctggttccgg aatcctgtcc tcagcttctt aatataactg ccttaaaact ttaatcccac    720
ttgcccctgt tacctaatta gagcagatga cccctcccct aatgcctgcg gagttgtgca    780
cgtagtaggg tcaggccacg gcagcctacc ggcaatttcc ggccaacagt aaatgagaa    840 catgaaaaca gaaaacggtt aaaactgtcc ctttctgtgt gaagatcacg ttccttcccc    900
cgcaatgtgc cccagacgc acgtgggtct tcaggggcc aggtgcacag acgtccctcc    960
acgttcaccc ctccacccctt ggactttctt ttcgccgtgg ctgcggcacc cttgcgcttt    1020
tgctggtcac tgccatggag gcacacagct gcagagacag agaggacgtg gcggcagag    1080 aggactgttg acatccaagc ttccttttgtt ttttttttcct gtccttctct cacctcctaa    1140
agtagacttc attttttccta acaggattag acagtcaagg agtggcttac tacatgtggg    1200
```

```
agcttttggt atgtgacatg cgggctgggc agctgttaga gtccaacgtg gggcagcaca    1260 gagaggggc cacctcccca ggccgtggct gcccacacac cccaattagc tgaattcgcg     1320
tgtggcagag ggaggaaaag gaggcaaacg tgggctgggc aatggcctca cataggaaac    1380
agggtcttcc tggagatttg tgtgatggaga tgtcaagcag gtggcctctg acgtcaccg    1440 ttgccctgca tggtggcccc agagcagcct ctatgaacaa cctcgtttcc aaaccacagc    1500
ccacagccgg agagtccagg aagacttgcg cactcagagc agaagggtag gagtcctcta    1560
gacagcctcg cagccgcgcc agtcgcccat agacactggc tgtgaccggg cgtgctggca    1620
gcggcagtgc acagtggcca gcactaaccc tccctgagaa gataaccggc tcattcactt    1680
cctcccagaa gacgcgtggt agcgagtagg cacaggcgtg cacctgctcc cgaattactc    1740
accgagacac acgggctgag cagacggccc cgtggatgga gacaaagagc tcttctgacc    1800
atatccttct taacacccgc tggcatctcc tttcgcgcct ccctccctaa cctactgacc    1860 cacctttga ttttagcgca cctgtgattg ataggccttc caaagagtcc cacgctggca    1920
tcaccctccc cgaggacgga gatgaggagt agtcagcgtg atgccaaaac gcgtcttctt    1980
aatccaattc taattctgaa tgtttcgtgt gggcttaata ccatgtctat taatatatag    2040
cctcgatgat gagagagtta caaagaacaa aactccagac acaaacctcc aaattttca    2100 gcagaagcac tctgcgtcgc tgagctgagg tcggctctgc gatccatacg tggccgcacc    2160
cacacagcac gtgctgtgac gatggctgaa cggaaagtgt acactgttcc tgaatattga    2220
aataaaacaa taaacttta atggtaaaaa aaaaaaaaaa aaaaaaa                   2267

<210> SEQ ID NO 43
<211> LENGTH: 2222
<212> TYPE: DNA
<213> ORGANISM: Homo sapiens

<400> SEQUENCE: 43
ggacaacacc ttcaaagaca ggccctctga gtccgacgag ctccagacca tccaagaaga      60
cagtgcagcc acctccgaga gcctggatgt gatggcgtca cagaagagac cctcccagag    120
gcacggatcc aagtacctgg ccacagcaag taccatggac catgccaggc atggcttcct    180
cccaaggcac agagacacgg gcatccttga ctccatcggg cgcttctttg gcggtgacag    240
gggtgcgccc aagcggggct ctggcaagga ctcacaccac ccggcaagaa ctgctcacta    300
cggctccctg ccccagaagt cacacggccg gacccaagat gaaaaccccg tagtccactt    360
cttcaagaac attgtgacgc ctcgcacacc accccgtcg cagggaaagg ggagaggact     420
gtccctgagc agatttagct gggggccga aggccagaga ccaggatttg gctacggagg    480
cagagcgtcc gactataaat cggctcacaa gggattcaag ggagtcgatg cccagggcac    540
gctttccaaa attttaagc tgggaggaag agatagtcgc tctggatcac ccatggctag    600
acgctgaaaa cccaccggt tccggaatcc tgtcctcagc ttcttaatat aactgcctta    660
aaactttaat cccacttgcc cctgttacct aattagagca gatgacccct cccctaatgc    720
ctgcggagtt gtgcacgtag tagggtcagg ccacggcagc ctaccggcaa tttccggcca    780
acagttaaat gagaacatga aaacagaaaa cggttaaaac tgtcccttc tgtgtgaaga    840 tcacgttcct tcccccgcaa tgtgccccca acgcacgtg ggtcttcagg gggccaggtg     900
cacagacgtc cctccacgtt caccctcca cccttggact ttctttcgc cgtggctgcg     960 gcacccttgc gcttttgctg gtcactgcca tggaggcaca cagctgcaga gacagagagg    1020
```

-continued

```
acgtgggcgg cagagaggac tgttgacatc caagcttcct ttgttttttt ttcctgtcct      1080
tctctcacct cctaaagtag acttcatttt tcctaacagg attagacagt caaggagtgg      1140
cttactacat gtgggagctt ttggtatgtg acatgcgggc tgggcagctg ttagagtcca      1200
acgtggggca gcacagagag ggggccacct ccccaggccg tggctgccca cacacccccaa     1260
ttagctgaat tcgcgtgtgg cagagggagg aaaaggaggc aaacgtgggc tgggcaatgg      1320
cctcacatag gaaacagggt cttcctggag atttggtgat ggagatgtca agcaggtggc      1380
ctctggacgt caccgttgcc ctgcatggtg gccccagagc agcctctatg aacaacctcg      1440
tttccaaacc acagcccaca gccgagagt ccaggaagac ttgcgcactc agagcagaag       1500
ggtaggagtc ctctagacag cctcgcagcc gcgccagtcg cccatagaca ctggctgtga      1560
ccgggcgtgc tggcagcggc agtgcacagt ggccagcact aaccctccct gagaagataa      1620
ccggctcatt cacttcctcc cagaagacgc gtggtagcga gtaggcacag gcgtgcacct      1680
gctcccgaat tactcaccga gacacacggg ctgagcagac ggccccgtgg atggagacaa      1740
agagctcttc tgaccatatc cttcttaaca cccgctggca tctcctttcg cgcctccctc      1800
cctaacctac tgacccacct tttgatttta gcgcacctgt gattgatagg ccttccaaag      1860
agtcccacgc tggcatcacc ctccccgagg acggagatga ggagtagtca gcgtgatgcc      1920
aaaacgcgtc ttcttaatcc aattctaatt ctgaatgttt cgtgtgggct taataccatg      1980
tctattaata tatagcctcg atgatgagag agttacaaag aacaaaactc cagacacaaa     2040
cctccaaatt tttcagcaga agcactctgc gtcgctgagc tgaggtcggc tctgcgatcc     2100
atacgtggcc gcacccacac agcacgtgct gtgacgatgg ctgaacggaa agtgtacact    2160
gttcctgaat attgaaataa aacaataaac ttttaatggt aaaaaaaaaa aaaaaaaaa     2220
aa                                                                   2222
```

<210> SEQ ID NO 44
<211> LENGTH: 2189
<212> TYPE: DNA
<213> ORGANISM: Homo sapiens

<400> SEQUENCE: 44

```
ggacaacacc ttcaaagaca ggccctctga gtccgacgag ctccagacca tccaagaaga       60
cagtgcagcc acctccgaga gcctggatgt gatggcgtca cagaagagac cctcccagag      120
gcacggatcc aagtacctgg ccacagcaag taccatggac catgccaggc atggcttcct      180
cccaaggcac agagacacgg gcatccttga ctccatcggg cgcttctttg gcggtgacag      240
gggtgcgccc aagcggggct ctggcaagga ctcacaccac ccggcaagaa ctgctcacta      300
cggctcccctg ccccagaagt cacacggccg gacccaagat gaaaaccccg tagtccactt     360
cttcaagaac attgtgacgc ctcgcacacc accccgtcg cagggaaagg gggccgaagg       420
ccagagacca ggatttggct acggaggcag agcgtccgac tataaatcgg ctcacaaggg      480
attcaaggga gtcgatgccc aggcacgct ttccaaaatt tttaagctgg gaggaagaga       540
tagtcgctct ggatcacca tggctagacg ctgaaaaccc acctggttcc ggaatcctgt       600
cctcagcttc ttaatataac tgccttaaaa ctttaatccc acttgcccct gttacctaat      660
tagagcagat gaccctcccc ctaatgcctg cggagttgtg cacgtagtag ggtcaggcca      720
cggcagccta ccggcaattt ccggccaaca gttaaatgag aacatgaaaa cagaaacgg       780
ttaaaactgt ccctttctgt gtgaagatca cgttccttcc cccgcaatgt gccccagac       840
gcacgtgggt cttcaggggg ccaggtgcac agacgtccct ccacgttcac ccctccaccc     900
```

```
ttggactttc ttttcgccgt ggctgcggca cccttgcgct tttgctggtc actgccatgg    960
aggcacacag ctgcagagac agagaggacg tgggcggcag agaggactgt tgacatccaa   1020
gcttcctttg ttttttttc ctgtccttct ctcacctcct aaagtagact tcattttcc    1080
taacaggatt agacagtcaa ggagtggctt actacatgtg ggagcttttg gtatgtgaca   1140
tgcgggctgg gcagctgtta gagtccaacg tggggcagca cagagagggg gccacctccc   1200
caggccgtgg ctgcccacac accccaatta gctgaattcg cgtgtggcag agggaggaaa   1260
aggaggcaaa cgtgggctgg gcaatggcct cacataggaa acagggtctt cctggagatt   1320
tggtgatgga gatgtcaagc aggtggcctc tggacgtcac cgttgccctg catggtggcc   1380
ccagagcagc ctctatgaac aacctcgttt ccaaaccaca gcccacagcc ggagagtcca   1440
ggaagacttg cgcactcaga gcagaagggt aggagtcctc tagacagcct cgcagccgcg   1500
ccagtcgccc atagacactg gctgtgaccg ggcgtgctgg cagcggcagt gcacagtggc   1560
cagcactaac cctccctgag aagataaccg gctcattcac ttcctcccag aagacgcgtg   1620
gtagcgagta ggcacaggcg tgcacctgct cccgaattac tcaccgagac acgggctg    1680
agcagacggc cccgtggatg gagacaaaga gctcttctga ccatatcctt cttaacaccc   1740
gctggcatct cctttcgcgc ctccctccct aacctactga cccacctttt gattttagcg   1800
cacctgtgat tgataggcct tccaaagagt cccacgctgg catcaccctc ccgaggacg    1860
gagatgagga gtagtcagcg tgatgccaaa acgcgtcttc ttaatccaat tctaattctg   1920
aatgtttcgt gtgggcttaa taccatgtct attaatatat agcctcgatg atgagagagt   1980
tacaaagaac aaaactccag acacaaacct ccaaattttt cagcagaagc actctgcgtc   2040
gctgagctga ggtcggctct gcgatccata cgtggccgca cccacacagc acgtgctgtg   2100
acgatggctg aacggaaagt gtacactgtt cctgaatatt gaaataaaac aataaacttt   2160
taatggtaaa aaaaaaaaaa aaaaaaaaa                                     2189
```

<210> SEQ ID NO 45
<211> LENGTH: 63
<212> TYPE: PRT
<213> ORGANISM: Artificial sequence
<220> FEATURE:
<223> OTHER INFORMATION: Synthetic

<400> SEQUENCE: 45

```
Ala Ser Gln Lys Arg Pro Ser Gln Arg His Gly Ser Lys Tyr Leu Ala
1               5                   10                  15

Thr Ala Ser Thr Met Asp His Ala Arg His Gly Phe Leu Pro Arg His
            20                  25                  30

Arg Asp Thr Gly Ile Leu Asp Ser Ile Gly Arg Phe Phe Gly Gly Asp
        35                  40                  45

Arg Gly Ala Pro Lys Arg Gly Ser Gly Lys Asp Ser His His Pro
    50                  55                  60
```

<210> SEQ ID NO 46
<211> LENGTH: 39
<212> TYPE: PRT
<213> ORGANISM: Artificial sequence
<220> FEATURE:
<223> OTHER INFORMATION: Synthetic

<400> SEQUENCE: 46

```
Ala Arg Thr Ala His Tyr Gly Ser Leu Pro Gln Lys Ser His Gly Arg
1               5                   10                  15
```

-continued

Thr Gln Asp Glu Asn Pro Val Val His Phe Lys Asn Ile Val Thr
                20                  25                  30

Pro Arg Thr Pro Pro Ser
        35

<210> SEQ ID NO 47
<211> LENGTH: 34
<212> TYPE: PRT
<213> ORGANISM: Artificial sequence
<220> FEATURE:
<223> OTHER INFORMATION: Synthetic

<400> SEQUENCE: 47

Gln Gly Lys Gly Arg Gly Leu Ser Leu Ser Arg Phe Ser Trp Gly Ala
1               5                   10                  15

Glu Gly Gln Arg Pro Gly Phe Gly Tyr Gly Gly Arg Ala Ser Asp Tyr
                20                  25                  30

Lys Ser

<210> SEQ ID NO 48
<211> LENGTH: 34
<212> TYPE: PRT
<213> ORGANISM: Artificial sequence
<220> FEATURE:
<223> OTHER INFORMATION: Synthetic

<400> SEQUENCE: 48

Ala His Lys Gly Phe Lys Gly Val Asp Ala Gln Gly Thr Leu Ser Lys
1               5                   10                  15

Ile Phe Lys Leu Gly Gly Arg Asp Ser Arg Ser Gly Ser Pro Met Ala
                20                  25                  30

Arg Arg

<210> SEQ ID NO 49
<211> LENGTH: 64
<212> TYPE: PRT
<213> ORGANISM: Artificial sequence
<220> FEATURE:
<223> OTHER INFORMATION: Synthetic

<400> SEQUENCE: 49

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
                20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Asp Ser His His Pro
    50                  55                  60

<210> SEQ ID NO 50
<211> LENGTH: 40
<212> TYPE: PRT
<213> ORGANISM: Artificial sequence
<220> FEATURE:
<223> OTHER INFORMATION: Synthetic

<400> SEQUENCE: 50

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile

```
                    20                  25                  30
Gly Leu Met Val Gly Gly Val Val
            35                  40

<210> SEQ ID NO 51
<211> LENGTH: 15
<212> TYPE: PRT
<213> ORGANISM: Artificial sequence
<220> FEATURE:
<223> OTHER INFORMATION: Synthetic

<400> SEQUENCE: 51

Arg Gly Ala Pro Lys Arg Gly Ser Gly Lys Asp Ser His His Pro
1               5                   10                  15

<210> SEQ ID NO 52
<211> LENGTH: 6
<212> TYPE: PRT
<213> ORGANISM: Artificial sequence
<220> FEATURE:
<223> OTHER INFORMATION: Synthetic

<400> SEQUENCE: 52

Lys Asp Ser His His Pro
1               5
```